(12) United States Patent
Schwartsburd et al.

(10) Patent No.: US 12,350,314 B2
(45) Date of Patent: *Jul. 8, 2025

(54) LIQUID FORMULATIONS COMPRISING MUTANT FGF-21 PEPTIDE PEGYLATED CONJUGATES

(71) Applicant: 89bio, Inc., San Francisco, CA (US)

(72) Inventors: Boris Schwartsburd, Rehovot (IL); Shaji Joseph, Sunnyvale, CA (US)

(73) Assignee: 89bio, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/504,561

(22) Filed: Nov. 8, 2023

(65) Prior Publication Data
US 2024/0307492 A1 Sep. 19, 2024

Related U.S. Application Data

(63) Continuation of application No. 18/165,081, filed on Feb. 6, 2023, now Pat. No. 11,850,275, which is a continuation of application No. 17/692,024, filed on Mar. 10, 2022, now Pat. No. 11,596,669.

(60) Provisional application No. 63/167,148, filed on Mar. 29, 2021, provisional application No. 63/159,717, filed on Mar. 11, 2021.

(51) Int. Cl.
| | |
|---|---|
| *A61K 38/18* | (2006.01) |
| *A61K 47/54* | (2017.01) |
| *A61K 47/60* | (2017.01) |
| *A61P 3/10* | (2006.01) |
| *C07K 14/50* | (2006.01) |

(52) U.S. Cl.
CPC ........ *A61K 38/1825* (2013.01); *A61K 47/549* (2017.08); *A61K 47/60* (2017.08); *A61P 3/10* (2018.01); *C07K 14/50* (2013.01)

(58) Field of Classification Search
None
See application file for complete search history.

(56) References Cited

U.S. PATENT DOCUMENTS

| | | | |
|---|---|---|---|
| 6,525,102 | B1 | 2/2003 | Chen et al. |
| 10,407,479 | B2 * | 9/2019 | Kopec .................. A61K 47/549 |
| 11,596,669 | B2 * | 3/2023 | Schwartsburd ......... A61K 47/02 |
| 11,850,275 | B2 * | 12/2023 | Schwartsburd ...... A61K 47/183 |
| 2005/0170004 | A1 | 8/2005 | Rosenberger et al. |
| 2019/0389921 | A1 | 12/2019 | Kopec et al. |
| 2020/0016075 | A1 | 1/2020 | Badiali et al. |
| 2020/0197490 | A1 | 6/2020 | Lindhout et al. |

FOREIGN PATENT DOCUMENTS

WO WO-2019043457 A2 * 3/2019 ......... A61K 38/1825

OTHER PUBLICATIONS

PubChem "Arginine Hydrochloride" CID 66250 (2005).

* cited by examiner

*Primary Examiner* — Melissa L Fisher
*Assistant Examiner* — Zachary J Miknis
(74) *Attorney, Agent, or Firm* — Greenberg Traurig, LLP; Barry Schindler; Natalie Salem

(57) ABSTRACT

The present disclosure relates to liquid pharmaceutical compositions comprising mutant Fibroblast Growth Factor-21 (FGF-21) peptide conjugate and prefilled syringe or auto-injector comprising liquid pharmaceutical compositions comprising mutant Fibroblast Growth Factor-21 (FGF-21) peptide conjugate.

9 Claims, 19 Drawing Sheets
Specification includes a Sequence Listing.

Overlay of three sample traces obtained for the 20nm Tris,150 mM Arg-HCl pH 8.0 demonstrating acceptable polydispersity.

Overlay of three sample traces obtained for the 20 mM Tris, 150 mM Arg-HCl pH 8.0, with lines indicating Tm for each of the triplicate readings.

3D surface plot for DSF T0
Tm (°C)
Design Points:
◉ Above Surface
◎ Below Surface
37.1433 ▬▬ 47.14

X1 = B: pH
X2 = A: Concentration

Actual Factors
C: Excipients = 150 mM Arg-HCl
D: Buffer = 20 mM Tris

3D surface plot - Percentage Main Peak (MP) icIEF 5°C
%MP icIEF 5°C (%)
Design Points:

- Above Surface
- Below Surface 63.0782  91.0413

X1 = B: pH
X2 = A: Concentration

Actual Factors
C: Excipients = 150 mM Arg-Hcl
D: Buffer = 20 mM Tris 3D surface for SEC %MP 2W/25°C SEC %MP 25C (oC)
Design Points:

● Above Surface
○ Below Surface 51.1972  83.1504

X1 = A: Concentration
X2 = B: pH

Actual Factors
C: Excipients = 150 mM Arg-Hcl
D: Buffer = 20 mM Tris

SDS-PAGE Reduced Gel - 12M stability(T0)

SDS-PAGE Non-Reduced Gel -12M stability(T0)

SDS-PAGE Reduced Gel -12M stability(T12M)

SDS-PAGE Non-Reduced Gel -12M stability(T12M)

Arginine HCl influence on Dimerization

LIQUID FORMULATIONS COMPRISING MUTANT FGF-21 PEPTIDE PEGYLATED CONJUGATES

RELATED APPLICATIONS

This application is a continuation of U.S. patent application Ser. No. 18/165,081, filed Feb. 6, 2023, which is a continuation of U.S. patent application Ser. No. 17/692,024, filed Mar. 10, 2022, now U.S. Pat. No. 11,596,669, which claims the benefit of and priority to U.S. Provisional Patent Application Ser. No. 63/159,717, filed Mar. 11, 2021, and U.S. Provisional Patent Application Ser. No. 63/167,148, filed Mar. 29, 2021, the disclosure of each of which is incorporated herein by reference in their entireties.

SEQUENCE LISTING

The instant application contains a Sequence Listing, submitted herewith which includes the file 180234-011511.xml having the following size 40,018 bytes, which was created on Nov. 7, 2023, the contents of which are hereby incorporated by reference herein.

TECHNICAL FIELD

The present disclosure relates to pharmaceutical liquid formulations comprising recombinant Fibroblast Growth Factor-21 (FGF-21) peptide pegylated conjugate and prefilled syringe or autoinjector comprising liquid pharmaceutical compositions comprising mutant Fibroblast Growth Factor-21 (FGF-21) peptide conjugate.

BACKGROUND

FGF-21 is an endocrine hormone that is naturally found as a monomeric non-glycosylated protein. Together with FGF-19 and FGF-23, FGF-21 belongs to the endocrine-acting sub-family while the remaining of the 18 mammalian FGF ligands are grouped into five paracrine-acting sub-families. Endocrine-acting FGFs, in contrast to paracrine-acting FGFs, exhibit only low affinity for heparin-sulfate and are thus able to enter the blood circulation. Thereby, endocrine FGFs are able to regulate metabolic processes, such as bile acid homeostasis, hepatic glucose and protein metabolism (FGF-19), glucose and lipid metabolism (FGF-21) and vitamin D and phosphate homeostasis (FGF-23).

SUMMARY

Aspects of the disclosure relates to a prefilled syringe or autoinjector comprising a liquid pharmaceutical composition, the liquid pharmaceutical composition comprising: (a) from 10 mg/ml to 48 mg/ml of a mutant Fibroblast Growth Factor-21 (FGF-21) peptide conSEQ id jugate comprising a mutant FGF-21 peptide comprising the amino acid sequence of SEQ ID NO: 2, a glycosyl moiety, and a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG; (b) from 150 mM to 500 mM arginine; (c) from 0.01% to 0.1% (w/v) Polysorbate 80 (PS-80) or Polysorbate 20 (PS-20); (d) from 5 to 25 mM buffer, pH 7-8; and (e) a pharmaceutically acceptable carrier. In some embodiments, the liquid pharmaceutical composition in the prefilled syringe or autoinjector comprises about 28 mg/mL mutant FGF-21 peptide conjugate, about 260 mM arginine HCl, about 20 mM Tris, 0.02% (w/v) PS-80 and wherein pH is about 7.1. In some embodiments, the liquid pharmaceutical composition in the prefilled syringe or autoinjector comprises about 20 mg/mL mutant FGF-21 peptide conjugate, about 150 mM arginine HCl, about 20 mM Tris, 0.02% (w/v) PS-80 and wherein pH is about 7.5. In some embodiments, the liquid pharmaceutical composition in the prefilled syringe or autoinjector comprises about 36 mg/ml mutant FGF-21 peptide conjugate, about 200 mM arginine HCl, about 20 mM Tris, 0.02% (w/v) PS-80 and wherein pH is about 7.1. In some embodiments, the liquid pharmaceutical composition in the prefilled syringe or autoinjector comprises about 44 mg/mL mutant FGF-21 peptide conjugate, about 200 mM arginine HCl, about 20 mM Tris, 0.02% (w/v) PS-80 and wherein pH is about 7.1. In some embodiments, the liquid pharmaceutical composition in the prefilled syringe or autoinjector comprises about 44 mg/mL mutant FGF-21 peptide conjugate, about 230 mM arginine HCl, about 20 mM Tris, 0.02% (w/v) PS-80 and wherein pH is about 7.1.

Aspects of the disclosure relate to a liquid pharmaceutical composition comprising: (a) from 10 mg/ml to 48 mg/ml of a mutant Fibroblast Growth Factor-21 (FGF-21) peptide conjugate comprising a mutant FGF-21 peptide comprising the amino acid sequence of SEQ ID NO: 2, a glycosyl moiety, and a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG; (b) from 150 mM to 500 mM arginine; (c) from 0.01% to 0.1% (w/v) Polysorbate 80 (PS-80) or Polysorbate 20 (PS-20); (d) from 5 to 25 mM buffer, pH 7-8; and (e) a pharmaceutically acceptable carrier.

Other aspects of the disclosure relate to a liquid pharmaceutical composition comprising: (a) from 10 mg/ml to 48 mg/ml of a mutant Fibroblast Growth Factor-21 (FGF-21) peptide conjugate comprising a mutant FGF-21 peptide comprising the amino acid sequence of SEQ ID NO: 2, a glycosyl moiety, and a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG; (b) from 150 mM to 500 mM arginine, from 50 mM to 250 mM alanine, 50 mM to 250 mM proline, 50 mM to 250 mM glycine, 50 mM to 250 mM MgCl2, 1 to 5% (v/v) glycerol, 1 to 5% (v/v) PEG 400, or combination thereof; (c) from 0.01% to 0.1% (w/v) Polysorbate 80 (PS-80) or Polysorbate 20 (PS-20); (d) a buffer having a pH of 7-8; and (e) a pharmaceutically acceptable carrier.

In some embodiments, the liquid formulation, further comprises a surfactant. In some embodiments, the surfactant comprises cetrimonium bromide, sodium gluconate or combination thereof. In some embodiments, the liquid formulation comprises from 0.05% to 0.1% (w/v) cetrimonium bromide, from 0.05% to 0.1% (w/v) sodium gluconate or combination thereof.

In some embodiments, the buffer is Tris or phosphate buffer. In some embodiments, the liquid formulation comprises 20 mM Tris buffer. In some embodiments, the pH of the liquid formulation is from 7.0 to 7.5.

In some embodiments, the liquid pharmaceutical composition comprises from 20 to 44 mg/ml of the mutant FGF-21 peptide conjugate.

In some embodiments, the liquid pharmaceutical composition comprises from 150 mM to 275 mM arginine. In some embodiments, the arginine in the liquid pharmaceutical composition comprises arginine HCl, arginine sulfate or combination thereof. In some embodiments, the weight ratio of mutant FGF-21 peptide conjugate to arginine is from 0.6 to 0.9. In some embodiments, the molar ratio of mutant FGF-21 peptide conjugate to arginine is from about 0.006 to about 0.009.

In some embodiments, the liquid pharmaceutical composition comprises about 28 mg/mL mutant FGF-21 peptide conjugate, about 260 mM arginine HCl, about 20 mM Tris, 0.02% (w/v) PS-80 and wherein pH is about 7.1.

In some embodiments, the liquid pharmaceutical composition comprises about 20 mg/mL mutant FGF-21 peptide conjugate, about 150 mM arginine HCl, about 20 mM Tris, 0.02% (w/v) PS-80 and wherein pH is about 7.5.

In some embodiments, the liquid pharmaceutical composition comprises about 36 mg/mL mutant FGF-21 peptide conjugate, about 200 mM arginine HCl, about 20 mM Tris, 0.02% (w/v) PS-80 and wherein pH is about 7.1.

In some embodiments, the liquid pharmaceutical composition comprises about 44 mg/mL mutant FGF-21 peptide conjugate, about 200 mM arginine HCl, about 20 mM Tris, 0.02% (w/v) PS-80 and wherein pH is about 7.1.

In some embodiments, the liquid pharmaceutical composition comprises about 44 mg/mL mutant FGF-21 peptide conjugate, about 230 mM arginine HCl, about 20 mM Tris, 0.02% (w/v) PS-80 and wherein pH is about 7.1.

In some embodiments, the liquid formulation has an osmolality of about 250 mOsmol/kg to about 550 mOsmol/kg.

In some embodiments, the liquid pharmaceutical composition is stable for up to 12 months at a temperature ranging from 2° C. to 8° C. In some embodiments, the liquid pharmaceutical composition is stable at room temperature for at least 3 months.

In some embodiments, a container comprising the liquid pharmaceutical composition is provided.

In some embodiments, the container is a prefilled syringe, a vial, or an autoinjector.

In some embodiments, a kit comprising the container and a label or instructions for administration and use of the liquid pharmaceutical composition is provided.

BRIEF DESCRIPTION OF THE DRAWINGS

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive.

DETAILED DESCRIPTION

Figure 1:
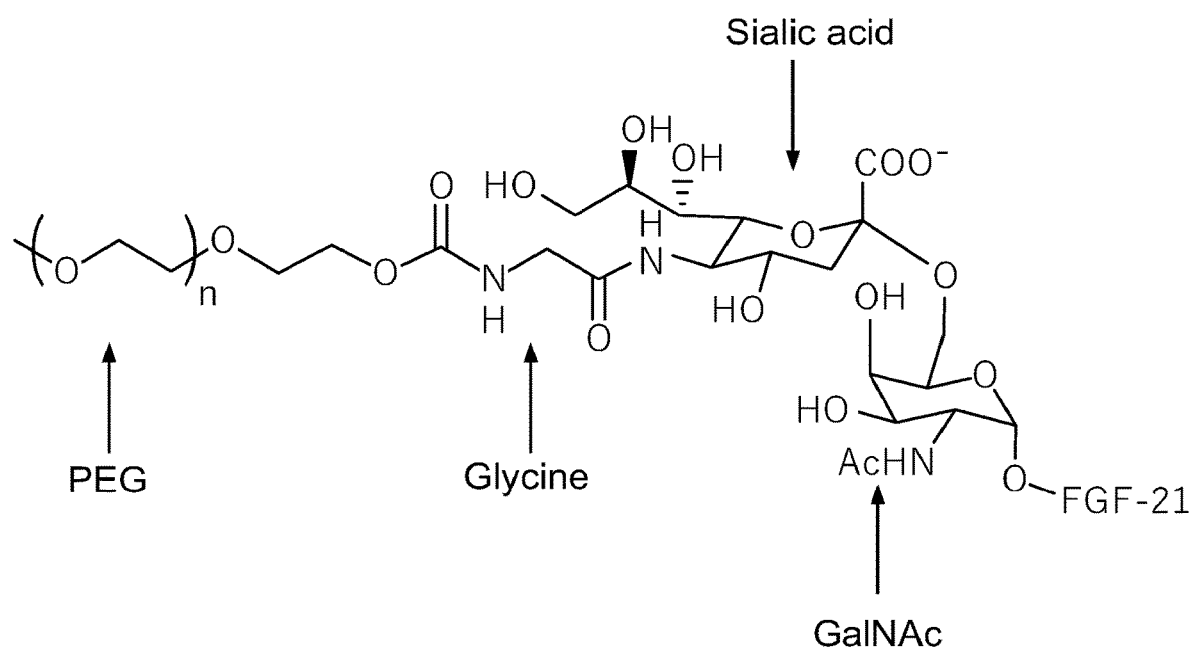
FIG. 1 shows the structure of a particular embodiment of the invention, namely of a mutant FGF-21 peptide conjugate comprising an exemplary structure of FGF-21(Thr)-GalNAc-Sia-Gly-PEG. n is chosen to give the desired molecular weight of PEG. With respect to 20 kDa PEG, n is in the range of selected from 450 to 460.

Among those benefits and improvements that have been disclosed, other objects and advantages of this disclosure will become apparent from the following description taken in conjunction with the accompanying figures. Detailed embodiments of the present disclosure are disclosed herein; however, it is to be understood that the disclosed embodiments are merely illustrative of the disclosure that may be embodied in various forms. In addition, each of the examples given regarding the various embodiments of the disclosure which are intended to be illustrative, and not restrictive.

Throughout the specification and claims, the following terms take the meanings explicitly associated herein, unless the context clearly dictates otherwise. The phrases "in one embodiment," "in an embodiment," and "in some embodiments" as used herein do not necessarily refer to the same embodiment(s), though it may. Furthermore, the phrases "in another embodiment" and "in some other embodiments" as used herein do not necessarily refer to a different embodiment, although it may. All embodiments of the disclosure are intended to be combinable without departing from the scope or spirit of the disclosure.

As used herein, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used herein, terms such as "comprising" "including," and "having" do not limit the scope of a specific claim to the materials or steps recited by the claim.

As used herein, the term "consisting essentially of" limits the scope of a specific claim to the specified materials or steps and those that do not materially affect the basic and novel characteristic or characteristics of the specific claim.

As used herein, terms such as "consisting of" and "composed of" limit the scope of a specific claim to the materials and steps recited by the claim.

All publications, patents and patent applications cited herein, whether supra or infra, are hereby incorporated by reference in their entirety.

Definitions

For the sake of clarity and readability, the following definitions are provided. Any technical feature mentioned for these definitions may be read on each and every embodiment of the invention. Additional definitions and explanations may be specifically provided in the context of these embodiments. Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well-known and commonly employed in the art. Standard techniques are used for nucleic acid and peptide synthesis. The techniques and procedures are generally performed according to conventional methods in the art and various general references (e.g., Sambrook et al., 1989, Molecular Cloning: A Laboratory Manual, 2d ed. Cold Spring Harbor Laboratory Press, Cold Spring Harbor, NY), which are provided throughout this document.

Enzyme: Enzymes are catalytically active biomolecules that perform biochemical reactions such as the transfer of glycosyl moieties or modified glycosyl moieties from the respective glycosyl donors to an amino acid of FGF-21 or to another glycosyl moiety attached to the peptide.

Protein: A protein typically comprises one or more peptides or polypeptides. A protein is typically folded into a 3-dimensional form, which may be required for the protein to exert its biological function. The sequence of a protein or peptide is typically understood to be in the order, i.e. the succession of its amino acids.

Recombinant protein: The term "recombinant protein" refers to proteins produced in a heterologous system, that is, in an organism that naturally does not produce such a protein, or a variant of such a protein, i.e. the protein or peptide is "recombinantly produced". Typically, the heterologous systems used in the art to produce recombinant proteins are bacteria (e.g., *Escherichia (E.) coli*), yeast (e.g., *Saccharomyces (S.) cerevisiae*) or certain mammalian cell culture lines.

Expression host: An expression host denotes an organism which is used for recombinant protein production. General expression hosts are bacteria, such as *E. coli*, yeasts, such as *Saccharomyces cerevisiae* or *Pichia pastoris*, or also mammal cells, such as human cells.

RNA, mRNA: RNA is the usual abbreviation for ribonucleic acid. It is a nucleic acid molecule, i.e. a polymer consisting of nucleotides. These nucleotides are usually adenosine-monophosphate, uridine-monophosphate, guanosine-monophosphate and cytidine-monophosphate monomers which are connected to each other along a so-called backbone. The backbone is formed by phosphodiester bonds between the sugar, i.e. ribose, of a first and a phosphate moiety of a second, adjacent monomer. The specific succession of the monomers is called the RNA sequence.

DNA: DNA is the usual abbreviation for deoxyribonucleic acid. It is a nucleic acid molecule, i.e. a polymer consisting of nucleotide monomers. These nucleotides are usually deoxy-adenosine-monophosphate, deoxy-thymidine-monophosphate, deoxy-guanosine-monophosphate and deoxy-cytidine-monophosphate monomers which are—by themselves—composed of a sugar moiety (deoxyribose), a base moiety and a phosphate moiety, and polymerized by a characteristic backbone structure. The backbone structure is, typically, formed by phosphodiester bonds between the sugar moiety of the nucleotide, i.e. deoxyribose, of a first and a phosphate moiety of a second, adjacent monomer. The specific order of the monomers, i.e. the order of the bases linked to the sugar/phosphate-backbone, is called the DNA-sequence. DNA may be single-stranded or double-stranded. In the double stranded form, the nucleotides of the first strand typically hybridize with the nucleotides of the second strand, e.g. by A/T-base-pairing and G/C-base-pairing.

Sequence of a nucleic acid molecule/nucleic acid sequence: The sequence of a nucleic acid molecule is typically understood to be in the particular and individual order, i.e. the succession of its nucleotides.

Sequence of amino acid molecules/amino acid sequence: The sequence of a protein or peptide is typically understood to be in the order, i.e. the succession of its amino acids.

Sequence identity: Two or more sequences are identical if they exhibit the same length and order of nucleotides or amino acids. The percentage of identity typically describes the extent, to which two sequences are identical, i.e. it typically describes the percentage of nucleotides that correspond in their sequence position to identical nucleotides of a reference sequence, such as a native or wild type sequence. For the determination of the degree of identity, the sequences to be compared are considered to exhibit the same length, i.e. the length of the longest sequence of the sequences to be compared. This means that a first sequence consisting of 8 nucleotides/amino acids is 80% identical to a second sequence consisting of 10 nucleotides/amino acids comprising the first sequence. In other words, in the context of the present disclosure, identity of sequences particularly relates to the percentage of nucleotides/amino acids of a sequence, which have the same position in two or more sequences having the same length. Gaps are usually regarded as non-identical positions, irrespective of their actual position in an alignment.

Newly introduced amino acids: "Newly introduced amino acids" denote amino acids which are newly introduced into an amino acid sequence in comparison to a native/wild type amino acid sequence. Usually by mutagenesis, the native amino acid sequence is changed in order to have a certain amino acid side chain at a desired position within the amino acid sequence. In the present disclosure, in particular the amino acid threonine is newly introduced into the amino acid sequence on the C-terminal side adjacent to a proline residue.

Functional group: The term is to be understood according to the skilled person's general understanding in the art and denotes a chemical moiety which is present on a molecule, in particular on the peptide or amino acid of the peptide or glycosyl residue attached to the peptide, and which may participate in a covalent or non-covalent bond to another chemical molecule, i.e. which allows e.g. the attachment of a glycosyl residue or PEG.

Native amino acid sequence: The term is to be understood according to the skilled person's general understanding in the art and denotes the amino acid sequence in the form of its occurrence in nature without any mutation or amino acid amendment by man. It is also called "wild-type sequence". "Native FGF-21" or "wild-type FGF-21" denotes FGF-21 having the amino acid sequence as it occurs in nature, such as the (not mutated) amino acid sequence of human FGF-21 as depicted in SEQ ID NO: 1. The presence or absence of an N-terminal methionine, which depends on the used expression host, usually does not change the status of a protein being considered as having its natural or native/wild-type sequence.

Mutated: The term is to be understood according to the skilled person's general understanding in the art. An amino acid sequence is called "mutated" if it contains at least one additional, deleted or exchanged amino acid in its amino acid sequence in comparison to its natural or native amino acid sequence, i.e. if it contains an amino acid mutation. Mutated proteins are also called mutants.

In the present disclosure, a mutated FGF-21 peptide is particularly a peptide having an amino acid exchange adjacent to a proline residue on the C-terminal side of the proline residue. Thereby a consensus sequence for O-linked glycosylation is introduced into FGF-21 such that the mutant FGF-21 peptide comprises a newly introduced O-linked glycosylation side. Amino acid exchanges are typically denoted as follows: $S^{172}T$ which means that the amino acid serine at position 172, such as in the amino acid sequence of SEQ ID NO: 1, is exchanged by the amino acid threonine.

Pharmaceutically effective amount: A pharmaceutically effective amount in the context of the disclosure is typically understood to be an amount that is sufficient to induce a pharmaceutical effect.

Therapy/treatment: The term "therapy" refers to "treating" or "treatment" of a disease or condition, inhibiting the disease (slowing or arresting its development), providing relief from the symptoms or side-effects of the disease (including palliative treatment), and relieving the disease (causing regression of the disease).

Therapeutically effective amount: is an amount of a compound that is sufficient to treat a disease or condition, inhibit the disease or condition, provide relief from symptoms or side-effects of the disease, and/or cause regression of the disease or condition.

Half-life: The term "half-life", as used herein in the context of administering a mutant FGF-21 peptide and/or conjugate thereof, is defined as the time required for the plasma concentration of a drug, i.e. of the mutant FGF-21 peptide and/or conjugate, in a subject to be reduced by one half.

O-linked glycosylation: "O-linked glycosylation" takes place at serine or threonine residues (Tanner et al., Biochim. Biophys. Acta. 906:81-91 (1987); and Hounsell et al, Glycoconj. J. 13:19-26 (1996)). In the present disclosure, O-linked glycosylation sites, which are amino acid motifs in the amino acid sequence of a peptide which are recognized by glycosyl transferases as attachment points for glycosyl residues, include the amino acid motif proline-threonine (PT) not present in the native/wild-type amino acid sequence. In particular, the threonine residue is newly introduced adjacent to a proline and on the C-terminal side of a proline residue. The glycosyl moiety is then attached to the —OH group of the threonine residue by the glycosyl transferase.

Newly introduced O-linked glycosylation side: "Newly introduced O-linked glycosylation side" denotes an O-linked glycosylation side which did not exist in the native or wild-type FGF-21 before introducing a threonine adjacent to and on the C-terminal side of a proline residue as described herein.

Adjacent: Adjacent denotes the amino acid immediately next to another amino acid in the amino acid sequence, either on the N-terminal or on the C-terminal side of the respective amino acid. In the present disclosure, e.g. the newly introduced threonine residue is adjacent to a proline residue on the C-terminal side of a proline residue.

Glycosyl moiety: A glycosyl moiety is a moiety consisting of one or more, identical or different glycosyl residues which links the mutant FGF-21 peptide to a polyethylene glycol (PEG), thereby forming a conjugate comprising a peptide, glycosyl moiety and PEG. The glycosyl moiety can be a mono-, di-, tri-, or oligoglycosyl moiety. The glycosyl moiety may comprise one or more sialic acid residues, one or more N-acetylgalactosamine (GalNAc) residues, one or more galactose (Gal) residues and others. The glycosyl moiety may be modified, such as with a PEG or methoxy-PEG (m-PEG), an alkyl derivative of PEG.

Glycoconjugation: "Glycoconjugation", as used herein, refers to the enzymatically mediated conjugation of a PEG-modified glycosyl moiety to an amino acid or glycosyl residue of a (poly)peptide, e.g. a mutant FGF-21 of the present disclosure. A subgenus of "glycoconjugation" is "glyco-PEGylation" in which the modifying group of the modified glycosyl moiety is PEG or m-PEG. The PEG may be linear or branched. Typically, a branched PEG has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched PEG can be represented in general form as R(-PEG-OX)$_m$ in which R represents the core moiety, such as glycerol or pentaerythritol, X represents a capping group or an end group, and m represents the number of arms. The terms "glyco-PEG" and "glycosyl-PEG" are used interchangeably and denote a chemical moiety consisting of PEG or methoxy-PEG (mPEG or m-PEG), one or more glycosyl residues (or glycosyl moieties), and optionally a linker between PEG/methoxy-PEG and the glycosyl moieties, such as an amino acid, e.g. glycine. An example of a glycosyl- PEG/glyco-PEG moiety is PEG-sialic acid (PEG-Sia). It should be noted that the terms "glyco-PEG" and "glycosyl-PEG" as well as "PEG-sialic acid" and "PEG-Sia" as well as similar terms for glyco-PEG moieties may or may not include a linker between PEG and the glycosyl moiety or moieties, i.e. "PEG-sialic acid" encompasses e.g. PEG-sialic acid as well as PEG-Gly-sialic acid as well as mPEG-Gly-sialic acid.

Sequence motif: A sequence motif denotes a short amino acid sequence, such as that comprising only two amino acids, which is present at any possible position in a longer amino acid sequence, such as in the amino acid sequence of human FGF-21. Sequence motifs are e.g. denoted as $P^{172}T$ which means that the proline at position 172 is followed C-terminally immediately by a threonine residue.

Sialic acid: The term "sialic acid" or "Sia" refers to any member of a family of nine-carbon carboxylated sugars. The most common member of the sialic acid family is N-acetyl-neuraminic acid (2-keto-5-acetamido-3,5-dideoxy-D-glyc-ero-D-galactononulopyranos-1-onic acid (often abbreviated as Neu5Ac, NeuAc, or NANA). A second member of the family is N-glycolylneuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) J. Biol. Chem. 261:11550-11557). Also included are 9-substituted sialic acids such as a 9-0-$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see e.g. Varki, Glycobiology 2:25-40 (1992)).

Pharmaceutically acceptable excipient: "Pharmaceutically acceptable" excipient includes any material, which when combined with the mutant FGF-21 peptide conjugate of the disclosure retains the conjugates' activity and is non-reactive with a subject's immune systems. Examples include, but are not limited to, any of the standard pharmaceutical excipients such as a phosphate buffered saline solution, Tris buffered solutions, water, salts, emulsions such as oil/water emulsion, and various types of wetting agents.

Pharmaceutical container: A "pharmaceutical container" is a container which is suitable for carrying a liquid pharmaceutical composition and typically made of an inert material and sterile.

Administering: The term "administering" means oral administration, inhalation, administration as a suppository, topical contact, intravenous, intraperitoneal, intramuscular, intralesional, intranasal or subcutaneous administration, or the implantation of a slow-release device e.g., a mini-osmotic pump, to the subject. Administration is by any route including parenteral, and transmucosal (e.g. oral, nasal, vaginal, rectal, or transdermal). Parenteral administration includes e.g. intravenous, intramuscular, intraarteriole, intradermal, subcutaneous, intraperitoneal, intraventricular and intracranial. Other modes of delivery include, but are not limited to, the use of liposomal formulations, intravenous infusion, transdermal patches, etc. In some embodiments, administration is subcutaneous injection.

Diabetes and diabetes related diseases: "Diabetes" is a well-known and well-characterized disease often referred to as diabetes mellitus. The term describes a group of metabolic diseases in which the person has high blood glucose levels (blood sugar), either because insulin production is inadequate, or because the body's cells do not respond properly to insulin, or both. Patients with high blood sugar will typically experience polyuria (frequent urination), they will become increasingly thirsty (polydipsia) and hungry (polyphagia). "Diabetes related diseases" are diseases characterized by the same symptoms such as obesity, polyuria, polydipsia and polyphagia.

Diabetes type 2: "Diabetes type 2" is the most common form of diabetes/diabetes mellitus. Diabetes type 2 most commonly develops in adulthood and is more likely to occur in people who are overweight and physically inactive. Unlike type 1 diabetes, which currently cannot be prevented, many of the risk factors for type 2 diabetes can be modified. The International Diabetes Foundation lists four symptoms that signal the need for diabetes testing: a) frequent urination, b) weight loss, c) lack of energy and d) excessive thirst. Insulin resistance is usually the precursor to diabetes type 2 a condition in which more insulin than usual is needed for glucose to enter the cells. Insulin resistance in the liver results in more glucose production while resistance in peripheral tissues means glucose uptake is impaired.

Non-alcoholic steatohepatitis (NASH): a condition where fat is deposited in the liver with subsequent liver damage and inflammation.

Metabolic syndrome: a defined cluster of risk factors (biochemical and physiological changes) that are associated with the development of type 2 diabetes and cardiovascular disease.

As used herein, "about" and "approximately" generally mean an acceptable degree of error for the quantity measured given the nature or precision of the measurements. Exemplary degrees of error are within 20 percent (%), typically, within 10%, and more typically, within 5% of a given range of values. The term "substantially" means more than 50%, more than 80%, or more than 90% or 95%.

FGF-21 Peptide Conjugate

Recombinant FGF-21 has been shown to influence plasma glucose and insulin levels, to reduce hepatic and circulating triglycerides and cholesterol levels, and to improve insulin sensitivity, energy expenditure, hepatic steatosis and obesity in a range of insulin-resistant animal models. For this reason, FGF-21 is an interesting target for the treatment of human Type 2 diabetes, Nonalcoholic Steatohepatitis (NASH) and associated metabolic diseases.

Natural FGF-21 has a comparatively short half-life in vivo, with a reported circulating half-life ranging from 0.5 to 4 hours in rodents and non-human primates, which limits its clinical applicability. The half-life of recombinant human FGF-21 is 1-2 hours. To improve pharmacokinetic properties of FGF-21, various half-life extension strategies have been developed. Abbreviations used herein include: PEG, poly(ethyleneglycol); PPG, poly(propyleneglycol); Ara, arabinosyl; Fru, fructosyl; Fuc, fucosyl; Gal, galactosyl; GalNAc, N-acetylgalactosaminyl; Glc, glucosyl; GlcNAc, N-acetylglucosaminyl; Man, mannosyl; ManAc, mannosaminyl acetate; Xyl, xylosyl; NeuAc, sialyl or N-acetylneuraminyl; Sia, sialyl or N-acetylneuraminyl; and derivatives and analogues thereof.

PEGylation

One method to prolong a protein's half-life is the attachment of one or more PEG moieties to the protein, which attachment increases the protein's biophysical solubility and stability in general. This approach has proven to be of particular value with respect to increasing the therapeutic half-life of proteins having properties suitable for treating subjects in need thereof. Native FGF-21, however, lacks a specific protein PEGylation site. Chemical PEGylation absent a specific protein PEGylation site is not site-specific and typically results in the generation of an inhomogeneous product population requiring extensive purification to achieve a homogeneous and high purity product—a prerequisite for market approval as a pharmaceutical composition. Accordingly, site-specific PEGylation of FGF-21 is desirable for generating site-specific PEGylated FGF-21 peptides having improved half-life and good biological activity.

Enzyme-based syntheses have the advantages of regioselectivity and stereoselectivity. Moreover, enzymatic syntheses may be performed with unprotected substrates. One possible method to attach PEG residues site-specifically to a protein is glycoPEGylation. In glycoPEGylation, a PEG moiety may be transferred to an amino acid or glycosyl residue attached to an amino acid of the protein or peptide using a glycosyltransferase. The general final structure is protein—glycosyl moiety—optional further linker—PEG. A more particular final structure is protein—(N-, C- or internal) amino acid of the protein—one or more glycosyl residues-optional linker (e.g., amino acid linker)—linear or branched PEG moiety of various lengths, wherein the glycosyl moiety may comprise one or more glycosyl residues. The one or more glycosyl residues comprising at least part of the structure linking the protein to the PEG moiety may be any possible glycosyl residue. A diverse array of methods for glycoPEGylating proteins are known in the art and are described in detail herein below.

In protein PEGylation, the larger the conjugated PEG moiety, the longer the expected half-life of a PEG-conjugated protein. This is due to the relatively enhanced ability of larger PEG moieties to protect conjugated proteins from proteases present in the blood stream. Large PEG moieties confer a larger effective radius to a PEG-conjugated protein than smaller PEG moieties. Larger proteins are also degraded in and removed from the blood stream more slowly than smaller proteins because they enter the kidney more slowly or are prevented from entering the kidney completely.

Accordingly, skilled persons favor PEGylation processes that call for attaching a longer PEG residue of higher molecular weight (e.g., ≥30 kDa PEG), a higher number of PEG residues in total, and/or more highly branched PEG residues to a protein in order to create a PEGylated protein having superior properties relative to the same protein conjugated to a shorter/smaller PEG moiety.

A considerable disadvantage associated with pegylation is, however, the potential for steric hindrance whereby a conjugated PEG moiety physically blocks an active site of the protein that is important or essential for protein activity. For example, a PEG moiety may specifically block a receptor binding site of a protein for its receptor, which in turn, leads to a significant and detrimental loss in protein activity. To avoid such potential inhibitory effects of pegylation, persons skilled in the art avoid attaching PEG near amino acids involved in receptor binding.

With respect to FGF-21, the C-terminus is critical for β-Klotho binding and the N-terminus is important for FGFR activation. Moreover, in silico modeling of FGF-21 based on the crystal structures of other FGF-21 family proteins and in vitro potency assays demonstrated that PEGylation of amino acid residues located in the putative receptor binding domains were inactive, while PEGylation at distal sites produced the most active analogs. Furthermore, greater than 100-fold loss of potency was observed in a cell-based potency assay when a PEG moiety was placed at position 180 in FGF-21. Fusion of FGF-21 to the Fc portion of an antibody was also examined, and fusion at the C-terminus of FGF-21 produced a much weaker analog than fusion at the N-terminus. In contrast, N-terminally PEGylated FGF-21 has been generated and shown to be biologically active. Based on knowledge in the field, therefore, a skilled person would avoid PEGylation close to the C-terminus of FGF-21 in light of the role this region of the protein plays in binding and signaling.

Generation of a plurality of mutant Fibroblast Growth Factor-21 (FGF-21) peptide conjugates is provided, each comprising
  i) a mutant FGF-21 peptide comprising at least one threonine (T) residue adjacent to at least one proline (P) residue on the C-terminal side of said at least one proline residue, thereby forming at least one O-linked glycosylation site which does not exist in the corresponding native FGF-21, wherein the corresponding native FGF-21 has an amino acid sequence that is at least 95% identical to SEQ ID NO: 1, and
  ii) a 20 kDa polyethylene glycol (PEG), wherein said 20 kDa PEG is covalently attached to said mutant FGF-21 peptide at said at least one threonine residue via at least one glycosyl moiety. In a particular embodiment, the mutant FGF-21 peptide conjugate comprises a mutant FGF-21 peptide comprising the amino acid sequence PT. In particular embodiments thereof, the mutant FGF-21 peptide comprises at least one amino acid sequence selected from the group consisting of P172T, P156T, P5T, P3T, P9T, P50T, P61T, P79T, P91T, P116T, P129T, P131T, P134T, P139T, P141T, P144T, P145T, P148T, P150T, P151T, P158T, P159T, P166T, P178T and combinations thereof, wherein the positions of proline and threonine are based on the amino acid sequence as depicted in SEQ ID NO: 1. In a more particular embodiment, the mutant FGF-21 peptide comprises at least one amino acid sequence selected from the group consisting of P172T, P156T, P5T and combinations thereof, particularly consisting of P172T, P156T and combinations thereof, wherein the positions of proline and threonine are based on the amino acid sequence as depicted in SEQ ID NO: 1. In a still more particular embodiment, the proline residue is located between amino acid 145 and the C-terminus of the mutant FGF-21 peptide, wherein the position of amino acid 145 is based on the amino acid sequence as depicted in SEQ ID NO: 1.

In another particular embodiment, the mutant FGF-21 peptide comprises the amino acid sequence P172T, wherein the positions of proline and threonine are based on the amino acid sequence as depicted in SEQ ID NO: 1.

In another particular embodiment, the mutant FGF-21 peptide comprises the mutations S173T and R176A, wherein the positions of the amino acids S and R are based on the amino acid sequence as depicted in SEQ ID NO: 1, particularly the mutant FGF-21 peptide comprises the amino acid sequence as depicted in SEQ ID NO: 2.

In another particular embodiment, the mutant FGF-21 peptide comprises the mutation Q157T, wherein the position of the amino acid Q is based on the amino acid sequence as depicted in SEQ ID NO: 1, particularly the mutant FGF-21 peptide comprises the amino acid sequence as depicted in SEQ ID NO: 4.

In another particular embodiment, the mutant FGF-21 peptide comprises the mutation D6T, wherein the position of the amino acid D is based on the amino acid sequence as depicted in SEQ ID NO: 1, particularly the mutant FGF-21 peptide comprises the amino acid sequence as depicted in SEQ ID NO: 5.

In other particular embodiments, the mutant FGF-21 peptide comprises an amino acid sequence selected from the group consisting of SEQ ID NOs: 2 to 28. In some embodiments, the mutant FGF-21 peptide comprises an amino acid sequence selected from the group consisting of SEQ ID NOs: 2 to 5. In some embodiments, the mutant FGF-21 peptide comprises an amino acid sequence selected from the group consisting of SEQ ID NOs: 2 to 4. In some embodiments, the mutant FGF-21 peptide comprises an amino acid sequence as depicted in SEQ ID NO: 2.

In other particular embodiments, the mutant FGF-21 peptide conjugate comprises at least one glycosyl moiety comprising N-acetylgalactosamine (GalNAc), galactose (Gal) and/or sialic acid (Sia). In a particular embodiment thereof, the at least one glycosyl moiety comprises the structure -GalNAc-Sia-.

In other particular embodiments, the mutant FGF-21 peptide conjugate comprises a 20 kDa PEG moiety which is attached to the at least one glycosyl moiety via an amino acid residue, particularly glycine (Gly). In an even more particular embodiment, the mutant FGF-21 peptide conjugate comprises the structure -GalNAc-Sia-Gly-PEG(20 kDa). Still more particularly, the mutant FGF-21 peptide conjugate comprises the structure:

mg/ml, 48 mg/ml. Aspects of the disclosure relate to a liquid pharmaceutical composition comprising or consisting of from about 10 mg/ml to about 48 mg/ml of a mutant Fibroblast Growth Factor-21 (FGF-21) peptide conjugate, from about 150 mM to about 500 mM arginine; from about 0.01 to about 0.1% (w/v) Polysorbate 80 (PS-80) or Polysorbate 20 (PS-20); about 20 mM buffer, pH 7-8; and a pharmaceutically acceptable carrier. In some embodiments, the formulation has an osmolality between about 250 mOsmol/kg to about 510 mOsmol/kg. In some embodiments, the liquid formulation comprises or consists of from 10 mg/ml to 48 mg/ml of a mutant Fibroblast Growth Factor-21 (FGF-21) peptide conjugate comprising a mutant FGF-21 peptide comprising the amino acid sequence of SEQ ID NO: 2, a glycosyl moiety, and a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG; from 150 mM to 500 mM Arginine; from 0.01 to 0.1% (w/v) Polysorbate 80 (PS-80) or Polysorbate 20 (PS-20); 20 mM buffer, pH 7-8; and a pharmaceutically acceptable carrier. In

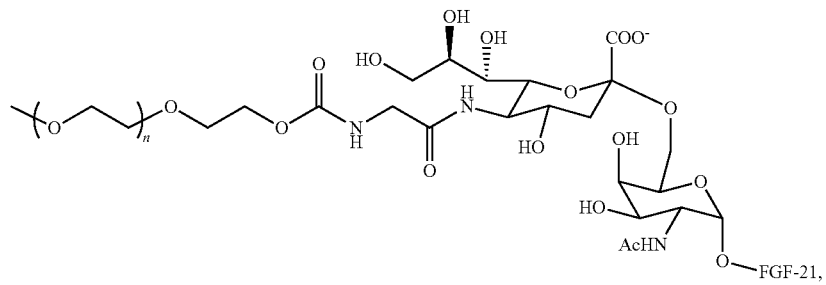

wherein n is an integer selected from 450 to 460.

In other particular embodiments, the mutant FGF-21 peptide conjugate comprises a 20 kDa PEG which is a linear or branched PEG, particularly a linear PEG. Still more particularly, the 20 kDa PEG is a 20 kDa methoxy-PEG (see U.S. Pat. No. 10,407,479 which is incorporated by reference in its entirety)

Liquid Pharmaceutical Composition

Encompassed herein is a liquid pharmaceutical composition comprising at least one mutant FGF-21 peptide conjugate and a pharmaceutically acceptable carrier.

In some embodiments, the mutant FGF-21 peptide conjugate is present in a concentration in the range from 0.1 mg/mL to 50 mg/mL. In some embodiments, the mutant FGF-21 peptide conjugate is present in a concentration in the range from 10 mg/mL to 48 mg/mL. In some embodiments the mutant FGF-21 peptide conjugate is present in a concentration of 26±4 mg/mL. For example, the FGF-21 peptide conjugate is present at a concentration of about 22, 26, 28, 30, 32, 36 mg/mL. In some embodiments, the mutant FGF-21 peptide conjugate is present in a 36±6 mg/mL. For example, the FGF-21 peptide conjugate is present at a concentration of about 30, 32, 34, 36, 38, 40, 42 mg/mL.

In some embodiments, the liquid pharmaceutical composition comprises 10-48 mg/ml FGF-21 peptide conjugate, for example 18 mg/ml, 20 mg/ml, 28 mg/ml, 36 mg/ml, 42 some embodiments, the formulation has an osmolality between about 250 mOsmol/kg to about 550 mOsmol/kg. In some embodiments, the liquid pharmaceutical composition comprising or consisting of from about 10 mg/ml to about 48 mg/ml of a mutant Fibroblast Growth Factor-21 (FGF-21) peptide conjugate comprising a mutant FGF-21 peptide comprising the amino acid sequence of SEQ ID NO: 2, a glycosyl moiety, and a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG; from about 150 mM to about 500 mM arginine, from about 50 mM to about 250 mM alanine, about 50 mM to about 250 mM proline, about 50 mM to about 250 mM glycine, about 50 mM to about 250 mM MgCl2, about 1% to about 5% (v/v) glycerol, about 1% to 5% (v/v) PEG 400, or combination thereof; from about 0.01 to about 0.1% (w/v) Polysorbate 80 (PS-80) or Polysorbate 20 (PS-20); about 20 mM buffer at pH 7-8; and a pharmaceutically acceptable carrier. In some embodiments, the weight ratio of mutant FGF-21 to arginine is from about 0.6 to about 0.7, from about 0.6 to about 0.8, about 0.6 to about 0.9, from about 0.6 to about 1, e.g. about 0.6, 0.7, 0.8, 0.9, 1. In some embodiments, the molar ratio of mutant FGF-21 to arginine is from about from about 0.006 to about 0.008, 0.006 to about 0.009, 0.006 to about 0.010, from about 0.007 to about 0.008, from about 0.007 to about 0.009, from about 0.007 to about 0.010, e.g about 0.006, 0.007, 0.008, 0.009. In some embodiments, the liquid formulation has an osmolality of about 250 mOsmol/kg to about 550 mOsmol/kg.

Liquid pharmaceutical compositions in some embodiments comprise 20 mg/mL PEG-FGF21 in 20 mM Tris, 150 mM Arginine, 0.02% (w/v) PS-80, pH 7.5. Liquid pharmaceutical formulations in some embodiments comprise 20 mg/mL PEG-FGF21 in 20 mM Phosphate, 150 mM Arginine, 0.02% (w/v) PS-80, pH 7.5. In some embodiments, the composition has an osmolality between about 250 mOsm/kg to about 380 mOsm/kg. In some embodiments, the composition has an osmolality of about 300 mOsm/kg. Liquid pharmaceutical compositions in some embodiments comprise 28 mg/mL PEG-FGF21 in 20 mM Tris, 275 mM Arginine, 0.02% (w/v) PS-80, pH 7-8. In some embodiments, the composition has an osmolality of about 505 mOsm/kg. Liquid pharmaceutical formulations in some embodiments comprise 18-44 mg/mL PEG-FGF21 in 20 mM Tris, 200-350 mM Arginine, 0.02% (w/v) PS-80, pH 7.0-pH 7.5. In some embodiments, the liquid pharmaceutical composition comprises about 20 mg/mL PEG-FGF21, about 150 mM arginine HCl, about 20 mM Tris, 0.02% (w/v) PS-80, wherein pH is about 7.5 and has an osmolality is about 300 mOsm/kg. In some embodiments, the liquid pharmaceutical composition comprises about 28 mg/mL PEG-FGF21, about 260 mM Arginine HCl, about 20 mM Tris, about 0.02% (w/v) PS80, wherein pH is about 7.1. In some embodiments, the liquid pharmaceutical composition comprises about 28 mg/mL PEG-FGF21, about 260 mM Arginine HCl, about 20 mM Tris, about 0.02% (w/v) PS80, wherein pH is about 7.1 and has an osmolality of about 505 mOsm/kg. In some embodiments, the liquid pharmaceutical composition comprises about 36 mg/mL PEG-FGF21, about 270 mM Arginine HCl, about 20 mM Tris, about 0.02% (w/v) PS80, wherein pH is about 7.1. In some embodiments, the liquid pharmaceutical composition comprises about 36 mg/mL PEG-FGF21, about 270 mM Arginine HCl, about 20 mM Tris, about 0.02% (w/v) PS80, wherein pH is about 7.1 and has a osmolality is about 530 mOsm/kg. In some embodiments, the liquid pharmaceutical composition comprises 36 mg/mL PEG-FGF21, 200 mM Arginine HCl, 20 mM Tris, 0.02% (w/v) PS80, wherein pH is about 7.1. In some embodiments, the liquid pharmaceutical composition comprises 36 mg/mL PEG-FGF21, 200 mM Arginine HCl, 20 mM Tris, 0.02% (w/v) PS80, wherein pH is about 7.1 and has an osmolality is about 421 mOsm/kg. In some embodiments, the liquid pharmaceutical composition comprises about 42 mg/mL PEG-FGF21, about 270 mM Arginine HCl, about 20 mM Tris, about 0.02% (w/v) PS80, wherein pH is about 7.1. In some embodiments, the liquid pharmaceutical composition comprises about 42 mg/mL PEG-FGF21, about 270 mM Arginine HCl, about 20 mM Tris, about 0.02% (w/v) PS80, wherein pH is about 7.1 and has an osmolality is about 528 mOsm/kg. In some embodiments, the liquid pharmaceutical composition comprises 44 mg/mL mutant FGF21, 200 mM Arginine HCl, 20 mM Tris, 0.02% (w/v) PS80, wherein pH is 7.1. In some embodiments, the liquid pharmaceutical composition comprises 44 mg/mL PEG-FGF21, 200 mM Arginine HCl, 20 mM Tris, 0.02% (w/v) PS80, wherein pH is 7.1 and has an osmolality is about 455 mOsm/kg. In some embodiments, the liquid pharmaceutical composition comprises 44 mg/mL PEG-FGF21, 230 mM Arginine HCl, 20 mM Tris, 0.02% (w/v) PS80, wherein pHis 7.1. In some embodiments, the liquid pharmaceutical composition comprises 44 mg/mL PEG-FGF21, 230 mM Arginine HCl, 20 mM Tris, 0.02% (w/v) PS80, wherein pH is 7.1 and has an osmolality is about 485 mOsm/kg.

Figure 22A:
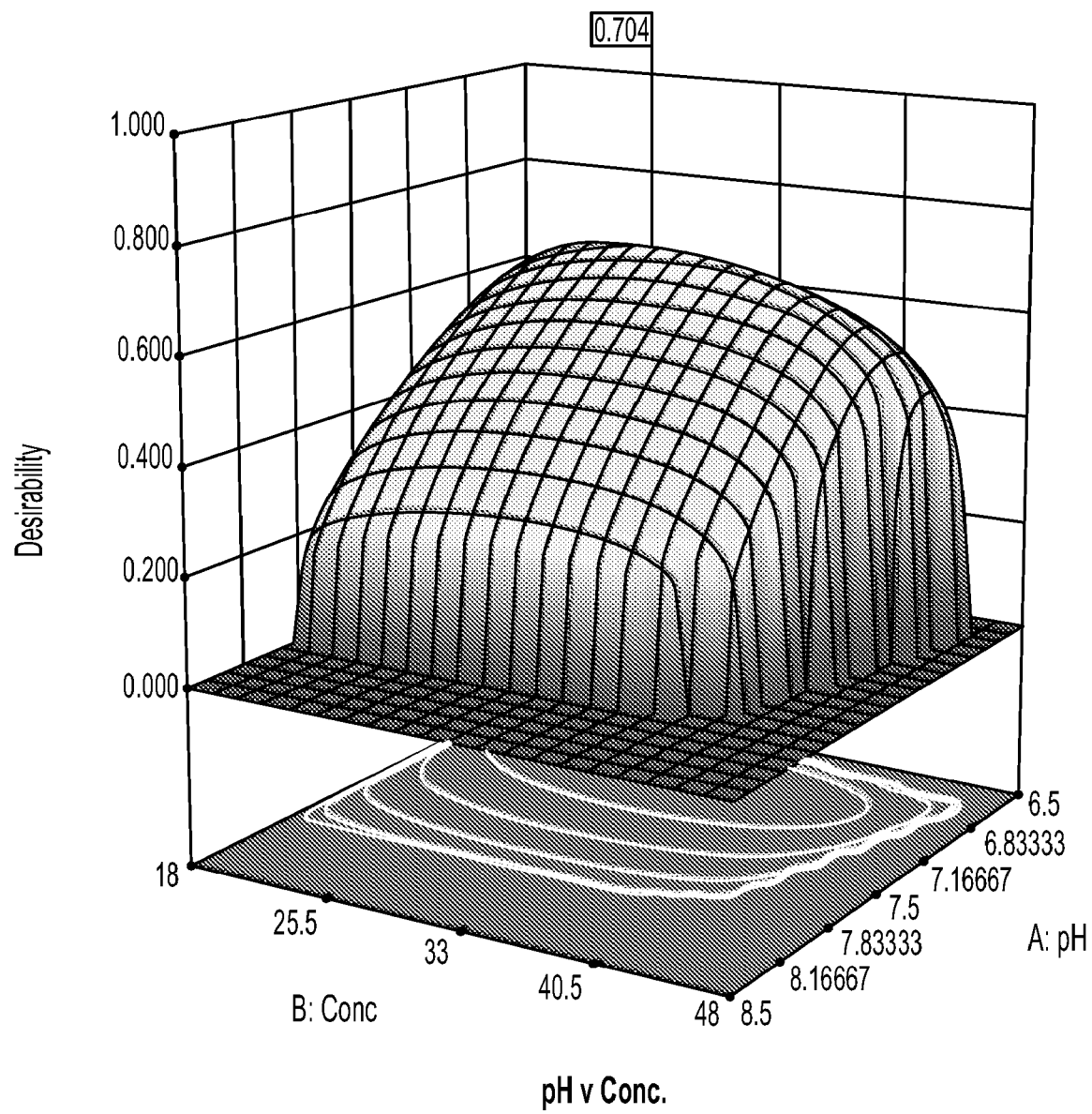
FIGS. 22A-22C show a response surface maps from DOE study for optimization of PEG-FGF21 formulation according to some embodiments.
Figure 22B:
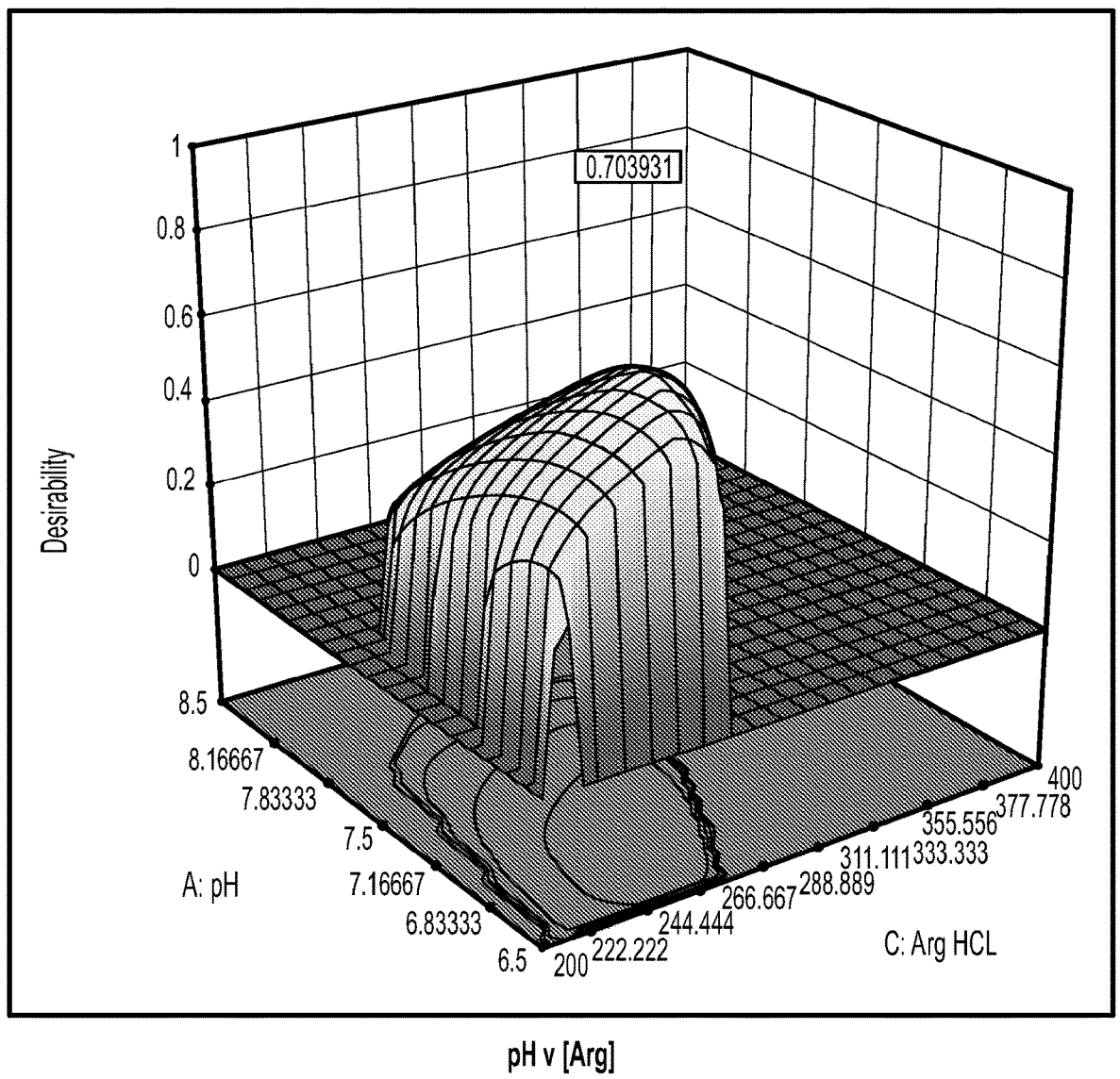
Figure 22C:
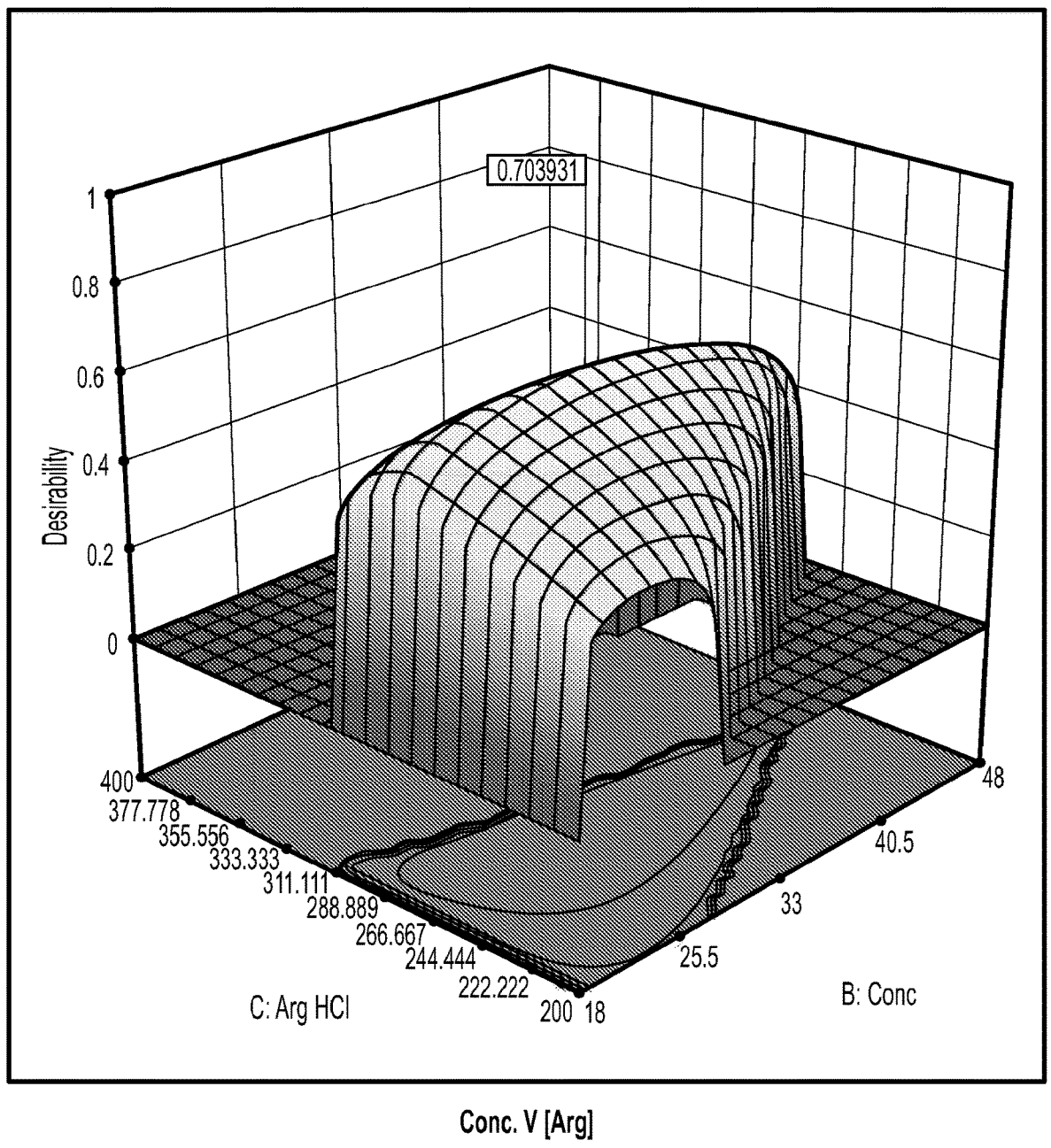

In some embodiments, a response surface analysis can be executed in which arginine concentration, pH and protein concentration can be evaluated to optimize the liquid pharmaceutical composition (see FIGS. 22A-22C).

In some embodiments, the liquid composition further comprises a surfactant. In some embodiments, the surfactant comprises cetrimonium bromide, sodium gluconate or combination thereof. In some embodiments, the liquid formulation comprises from about 0.05% to about 0.1% (w/v) cetrimonium bromide, from about 0.05% to about 0.1% (w/v) sodium gluconate or combination thereof.

In some embodiments, the liquid pharmaceutical composition further comprising one or more active agent. In some embodiments, the PEG-FGF21 is co-formulated with one or more active agent. In some embodiments, the one or more active agent can comprise a peptide, a small molecule or combinations thereof. In some embodiments, the one or more active agent can comprise an hormone. For example, the one or more agents can comprise oxyntomodulin, insulin, leptin, glucagon. eroxisome proliferator-activated receptor (PPAR) agonists, FXR (Farnesoid X receptor) agonists, Thyroid Hormone Receptor-Beta (TRβ) Agonists, Sodium glucose co-transporter 2 (SGLT2) Inhibitors, analogs thereof, or combinations thereof. As used herein an "analog" is a molecule having a modification including one or more amino acid substitutions, deletions, inversions or additions when compared with wild type peptide sequence.

The buffering agent may be present in a concentration from 1 mM to 100 mM. In some embodiments, the buffering agent is present at a concentration ranging from 2 mM to 75 mM, 5 mM to 50 mM, 10 mM to 25 mM, 14 to 22 mM. In some embodiments, the buffering agent is present at a concentration of about 14, 16, 18, 20, 22, 24, 26, 30, 32, 34, 36, 38, 40 mM or more. For example, the buffering agent is present at a concentration of about 20 mM. The pH may be in the range from 6.0 to 8.5, from 6.5 to 8.0, from 6.75 to 8.0, from 7.1 to 8. The buffering agent may be a Tris phosphate buffer. For example, the buffering agent can have a pH of 7, 7.1, 7.2, 7.3, 7.4, 7.5, 7.6, 7.7, 7.8, 7.9 or 8.

The liquid pharmaceutical composition may further comprise a tonicity modifying agent. Suitable tonicity modifying agents include glycerol, amino acids, sodium chloride, proteins, or sugars and sugar alcohols. For example, the modifying agent comprise arginine, such as arginine HCl or arginine sulfate. The tonicity modifying agent is present in a concentration of 50 mM to 500 mM. For example, the modifying agent (e.g. arginine HCL) comprises from 150 mM to 500 mM arginine, 150 to 275 mM or 245 to 275 mM. In some embodiments, modifying agent comprise arginine, such as arginine HCl or arginine sulfate is present at a concentration between 31.6 mg/ml (150 mM) and 54.8 mg/ml (260 mM).

The liquid pharmaceutical composition may further comprise a surfactant, particularly a non-ionic surfactant. The surfactant or non-ionic surfactant may be a polysorbate-based non-ionic surfactant, particularly polysorbate 20 or polysorbate 80, and more particularly polysorbate 80. The surfactant or non-ionic surfactant may be present in a concentration of 0.01% (w/v) to 1% (w/v). For example, the surfactant or non-ionic surfactant may be present in a concentration of 0.01%, 0.02%. 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, or 1% (w/v).

In some embodiments, the liquid pharmaceutical composition may further comprise cetrimonium bromide, sodium gluconate or combination thereof. For example, the composition may comprise from 0.05% to 0.1% (w/v) cetrimonium bromide, from 0.05% to 0.1% (w/v) sodium gluconate or combination thereof.

In an embodiment, the liquid pharmaceutical composition comprises 10 mg/mL to 50 mg/ml of mutant FGF-21 peptide conjugate, 1 mM to 100 mM buffering agent, for example Tris buffer, 150 mM to 500 mM tonicity arginine, and 0.02% to 1% (w/v) polysorbate-based non-ionic surfactant, particularly polysorbate 80, and has a pH of 7.0 to 8.0.

In some embodiments, the liquid formulation comprises 0.02% (w/v) PS80 (0.2 mg/ml). In some embodiments, the buffer is Tris or phosphate buffer. In some embodiments, the liquid formulation comprises 20 mM Tris buffer. In some embodiments, the liquid formulation comprises 28 mg/ml of mutant FGF-21. In some embodiments, the liquid formulation comprises 36 mg/ml of mutant FGF-21. In some embodiments, the liquid formulation comprises 44 mg/ml of mutant FGF-21. In some embodiments, the liquid formulation comprises from 150 mM to 275 mM arginine. In some embodiments, arginine is arginine HCl or arginine sulfate. In some embodiments, the pH is 7.1.

In some embodiments, the liquid pharmaceutical composition comprises about 20 mg/mL mutant FGF21, about 150 mM arginine HCl, about 20 mM Tris, 0.02% (w/v) PS-80 and wherein pH is about 7.5. In some embodiments, the liquid pharmaceutical composition comprises about 28 mg/mL mutant FGF21, about 260 mM arginine HCl, about 20 mM Tris, about 0.02% (w/v) PS80 and wherein pH is about 7.1. In some embodiments, the liquid pharmaceutical composition comprises about 36 mg/mL mutant FGF21, about 270 mM arginine HCl, about 20 mM Tris, about 0.02% (w/v) PS80 and wherein pH is about 7.1. In some embodiments, the liquid pharmaceutical composition comprises 36 mg/mL mutant FGF21, 200 mM arginine HCl, 20 mM Tris, 0.02% (w/v) PS80 and wherein pH is about 7.1 In some embodiments, the liquid pharmaceutical composition comprises about 42 mg/mL mutant FGF21, about 270 mM arginine HCl, about 20 mM Tris, about 0.02% (w/v) PS80 and wherein pH is about 7.1. In some embodiments, the liquid pharmaceutical composition comprises 44 mg/mL mutant FGF21, 200 mM arginine HCl, 20 mM Tris, 0.02% (w/v) PS80 and wherein pH is 7.1. In some embodiments, the liquid pharmaceutical composition comprises 44 mg/mL mutant FGF21, 230 mM arginine HCl, 20 mM Tris, 0.02% (w/v) PS80 and wherein pH is 7.1.

In some embodiments, the mutant Fibroblast Growth Factor-21 (FGF-21) peptide conjugate comprises a mutant FGF-21 peptide comprising the amino acid sequence of SEQ ID NO: 2, a glycosyl moiety, and a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG. In some embodiments, the mutant FGF-21 peptide conjugate comprises the structure:

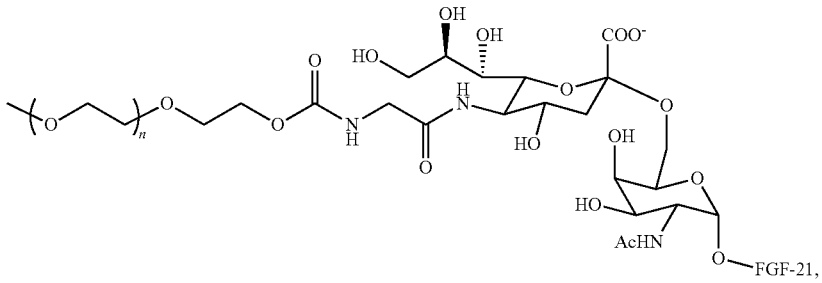

wherein n is an integer selected from 450 to 460.

In some embodiments, the liquid pharmaceutical composition is stable at a temperature ranging from 2-8° C. for 12 months or more. In an embodiment, the liquid pharmaceutical composition is stable at a temperature ranging from 2-8° C. for up to 12 months. In an embodiment, the pharmaceutical composition is stable at room temperature for at least 3 months. In an embodiment, the pharmaceutical composition is stable at a temperature of 25° C. for at least 3 months. In an embodiment, the liquid pharmaceutical composition is stable at a temperature of about −20° C. for 3 months, 6 months, 12 months or more.

A pharmaceutical container comprising a liquid pharmaceutical composition comprising same are also encompassed herein. Suitable pharmaceutical containers include, without limitation, a syringe, an autoinjector, vial, infusion bottle, ampoule, carpoule, a syringe equipped with a needle protection system, and a carpoule within an injection pen.

In some embodiments, the container comprising the liquid pharmaceutical composition is a prefilled syringe, a vial, or an autoinjector or the like.

Kits comprising one or more container comprising the liquid pharmaceutical composition also encompassed herein. Associated with the kits can be instructions customarily included in commercial packages of therapeutic, prophylactic or diagnostic products, that contain information about, for example, the indications, usage, dosage, manufacture, administration, contra-indications, and/or warnings concerning the use of such therapeutic, prophylactic or diagnostic products. The kit can also be associated with a label that can be any kind of data carrier (e.g., a leaflet, sticker, chip, print or bar code) comprising information. In certain embodiments, the instructions etc. as listed above can be comprised in or on the label. The kit can further comprise a device for administration of the formulation, and particularly a device that contains the formulation, i.e., a pre-filled device such as, but not limited to, a pre-filled syringe or a pre-filled autoinjector. The kit can also comprise a container comprising the formulation, i.e., a pre-filled container, such as a pre-filled vial, cartouche, sachet, or ampoule.

Also encompassed herein is a method of producing the mutant FGF-21 peptide conjugate, comprising the steps of:
(1) recombinantly producing the mutant FGF-21 peptide in an expression host; and (2) enzymatically attaching to the mutant FGF-21 peptide of step (1) a PEG-glycosyl moiety, wherein the PEG has 20 kDa, thereby forming the mutant FGF-21 peptide conjugate. In a particular embodiment, the expression host is *Escherichia coli*. In a more particular embodiment, step (2) comprises a step (2a) of contacting the mutant FGF-21 peptide with a GalNAc donor and a GalNAc transferase under conditions suitable to transfer GalNAc from the GalNAc donor to the at least one threonine residue of the mutant FGF-21 peptide. In a still more particular embodiment, the GalNAc donor is UDP-GalNAc. In another particular embodiment, the GalNAc transferase is MBP-GalNAcT2. In another particular embodiment, step (2) further comprises a step (2b) of contacting the product of step (1) or of step (2a), if present, with a 20 kDa PEG-Sia donor and a sialyltransferase under conditions suitable to transfer 20 kDa PEG-Sia from the 20 kDa PEG-Sia donor to the at least one threonine residue of the mutant FGF-21 peptide or to the GalNAc at the mutant FGF-21 peptide if step (2a) is present. In a more particular embodiment, the 20 kDa PEG-Sia donor is 20 kDa PEG-Sia-CMP. In a still more particular embodiment, the sialyltransferase is ST6GalNAcI. In a still further particular embodiment, the 20 kDa PEG-Sia donor comprises the structure through a saccharyl moiety, which moiety can be a portion of an O-linked or N-linked glycan structure on the peptide.

In accordance with the above, conjugates of glycosylated mutant FGF-21, which have glycosylation sites that do not exist in the corresponding wild-type FGF-21 sequence are provided (see U.S. Pat. No. 10,407,479 incorporated by reference in its entirety). Such conjugates were formed by the enzymatic attachment of a modified sugar to the glycosylated FGF-21 peptide. The modified sugar, when interposed between the peptide and the modifying group on the sugar may be referred to herein as "a glycosyl linking group." Taking advantage of the exquisite selectivity of enzymes, such as glycosyltransferases, mutant FGF-21 peptides having a desired group at one or more specific locations were generated. More particularly, glycosyltransferases were used to attach modified sugars to carbohydrate moieties on mutant FGF-21 glycopeptides.

FGF-21 Conjugates

In another aspect, exemplary conjugates of a modified sugar and a mutant FGF-21 peptide are presented. More particularly, mutant FGF-21 peptide conjugates were made comprising a mutant FGF peptide and at least one modified sugar, wherein a first of the at least one modified sugars is linked to an amino acid of the peptide through a glycosyl

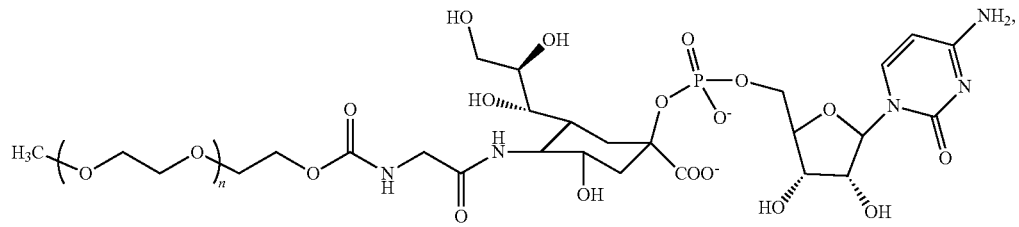

wherein n is an integer selected from 450 to 460.

Methods for Glycosylation and Glycoconjugation of FGF-21 Peptides

Post-expression in vitro modification of peptides and proteins is commonly used to produce glycopeptides and glycoproteins. A diverse array of enzymes that transfer saccharide donor moieties is available, thereby making in vitro enzymatic synthesis of glycoconjugates with custom designed glycosylation patterns and glycosyl structures possible. See, for example, U.S. Pat. Nos. 5,876,980; 6,030,815; 5,728,554; 5,922,577; and published patent applications WO 98/31826; WO 01/88117; WO 03/031464; WO 03/046150; WO 03/045980; WO 03/093448; WO 04/009838; WO 05/089102; WO 06/050247; WO 12/016984; US2002/142370; US2003/040037; US2003/180835; US2004/063911; US2003/207406; and US2003/124645, each of which is incorporated herein by reference.

Due to the versatility of the enzymes and methods available for adding and/or modifying glycosyl residues on a peptide, the glycosyl linking groups can have substantially any structure.

Accordingly, glycosyl linking groups can comprise virtually any mono- or oligo-saccharide. The glycosyl linking groups can be attached to an amino acid either through the side chain or through the peptide backbone. Alternatively, the glycosyl linking groups can be attached to the peptide linking group. As described herein, the amino acid to which the glycosyl linking group is attached is mutated to create a site recognized by the glycosyltransferase.

In another exemplary embodiment, a mutant FGF-21 peptide conjugate can comprise a mutant FGF-21 peptide and a glycosyl group attached to the mutated amino acid residue of the mutant FGF-21 peptide.

In an exemplary embodiment, the glycosyl group is an intact glycosyl linking group. In another exemplary embodiment, the glycosyl group further comprises a modifying group. In another exemplary embodiment, the modifying group is a non-glycosidic modifying group. In another exemplary embodiment, the modifying group does not include a naturally occurring saccharide moiety.

Modified Sugars

In an exemplary embodiment, mutant FGF-21 peptides are reacted with a modified sugar, thus forming a peptide conjugate. A modified sugar comprises a "sugar donor moiety" as well as a "sugar transfer moiety". The sugar donor moiety is any portion of the modified sugar that will be attached to the peptide, either through a glycosyl moiety or amino acid moiety, as a conjugate described herein. The sugar donor moiety includes those atoms that are chemically altered during their conversion from the modified sugar to the glycosyl linking group of the mutant FGF-21 peptide conjugate. The sugar transfer moiety is any portion of the modified sugar that will be not be attached to the peptide as a conjugate described herein.

For modified sugars described herein, the saccharyl moiety may be a saccharide, a deoxy-saccharide, an aminosaccharide, or an N-acyl saccharide. The term "saccharide" and its equivalents, "saccharyl," "sugar," and "glycosyl" refer to monomers, dimers, oligomers and polymers. The sugar moiety is also functionalized with a modifying group. The modifying group is conjugated to the saccharyl moiety, typically, through conjugation with an amine, sulfhydryl or hydroxyl, e.g., primary hydroxyl, moiety on the sugar. In an exemplary embodiment, the modifying group is attached through an amine moiety on the sugar, e.g., through an amide, a urethane or a urea that is formed through the reaction of the amine with a reactive derivative of the modifying group.

Any saccharyl moiety can be utilized as the sugar donor moiety of the modified sugar. The saccharyl moiety can be a known sugar, such as mannose, galactose or glucose, or a species having the stereochemistry of a known sugar. The general formulae of these modified sugars are:

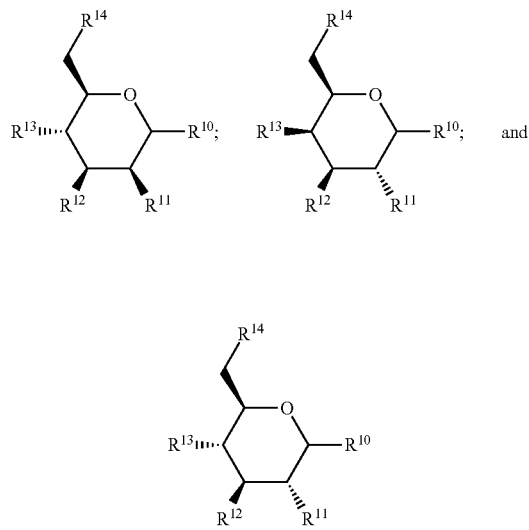

Other saccharyl moieties that are useful in methods described herein include, but are not limited to fucose and sialic acid, as well as amino sugars such as glucosamine, galactosamine, mannosamine, the 5-amine analogue of sialic acid and the like. The saccharyl moiety can be a structure found in nature or it can be modified to provide a site for conjugating the modifying group. For example, in one embodiment, the modified sugar provides a sialic acid derivative in which the 9-hydroxy moiety is replaced with an amine. The amine is readily derivatized with an activated analogue of a selected modifying group. Examples of modified sugars useful in methods described herein are presented in PCT Patent Application No. PCT/US05/002522, which is incorporated herein by reference in its entirety.

A further exemplary embodiment utilizes modified sugars in which the 6-hydroxyl position is converted to the corresponding amine moiety, which bears a linker-modifying group cassette such as those set forth above. Exemplary glycosyl groups that can be used as the core of these modified sugars include Gal, GalNAc, Glc, GlcNAc, Fuc, Xyl, Man, and the like. A representative modified sugar according to this embodiment is set forth below:

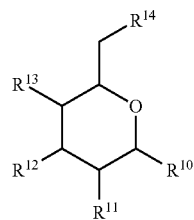

in which $R^{11}$-$R^{14}$ are members independently selected from H, OH, C(O)CH$_3$, NH, and NH C(O)CH$_3$. $R^{10}$ is a link to, e.g., another glycosyl residue (—O-glycosyl). $R^{14}$ is OR$^1$, NHR$^1$ or NH-L-R$^1$. $R^1$ and NH-L-R$^1$ are as described herein.

In a still further exemplary embodiment, the glycosyl groups used as the core of modified sugars in which the 6-hydroxyl position is converted to the corresponding amine moiety include Gal and/or GalNAc.

Glycosyl Linking Groups

In an exemplary embodiment, mutant FGF-21 peptide conjugates comprising a modified sugar described herein and a mutant FGF peptide are presented. In this embodiment, the sugar donor moiety (such as the saccharyl moiety and the modifying group) of the modified sugar becomes a "glycosyl linking group". The "glycosyl linking group" can alternatively refer to the glycosyl moiety which is interposed between the peptide and the modifying group.

In the exemplary embodiments that follow, the disclosure is illustrated by reference to the use of selected derivatives of furanose and pyranose. Those of skill in the art will appreciate that the structures and compositions set forth are generally applicable across the genus of glycosyl linking groups and modified sugars. The glycosyl linking group can, therefore, comprise virtually any mono- or oligo-saccharide.

In an exemplary embodiment, methods described herein utilize a glycosyl linking group that has the formula:

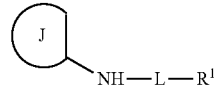

in which J is a glycosyl moiety, L is a bond or a linker and $R^1$ is a modifying group, e.g., a polymeric modifying group. Exemplary bonds are those that are formed between an NH$_2$ moiety on the glycosyl moiety and a group of complementary reactivity on the modifying group. For example, when $R^1$ includes a carboxylic acid moiety, this moiety may be activated and coupled with the NH$_2$ moiety on the glycosyl residue affording a bond having the structure NHC(O)R$^1$. J can be a glycosyl moiety that is "intact", not having been degraded by exposure to conditions that cleave the pyranose or furanose structure, e.g. oxidative conditions, e.g., sodium periodate.

Exemplary linkers include alkyl and heteroalkyl moieties. The linkers include linking groups, for example acyl-based linking groups, e.g., —C(O)NH—, —OC(O)NH—, and the like. The linking groups are bonds formed between components of the conjugates, e.g., between the glycosyl moiety and the linker (L), or between the linker and the modifying group ($R^1$). Other exemplary linking groups are ethers, thioethers and amines. For example, in one embodiment, the linker is an amino acid residue, such as a glycine residue. The carboxylic acid moiety of the glycine is converted to the corresponding amide by reaction with an amine on the glycosyl residue, and the amine of the glycine is converted to the corresponding amide or urethane by reaction with an activated carboxylic acid or carbonate of the modifying group.

An exemplary species of NH-L-R$^1$ has the formula: —NH{C(O)(CH$_2$)$_a$NH}$_s${C(O)(CH$_2$)$_b$(OCH$_2$CH$_2$)$_c$O(CH$_2$)$_d$NH}$_t$R$^1$, in which the indices s and t are independently 0 or 1. The indices a, b and d are independently integers from 0 to 20, and c is an integer from 1 to 2500. Other similar linkers are based on species in which an —NH moiety is replaced by another group, for example, —S, —O or —CH$_2$. As is understood in the art, one or more of the bracketed moieties corresponding to indices s and t can be replaced with a substituted or unsubstituted alkyl or heteroalkyl moiety.

More particularly, compounds described herein may comprise NH-L-R', wherein NH-L-R' is: NHC(O)(CH$_2$)$_a$NHC(O)(CH$_2$)$_b$(OCH$_2$CH$_2$)$_c$O(CH$_2$)$_d$NHR$^1$, NHC(O)(CH$_2$)$_b$(OCH$_2$CH$_2$)$_c$O(CH$_2$)$_d$NHR$^1$, NHC(O)O(CH$_2$)$_b$(OCH$_2$CH$_2$)$_c$O(CH$_2$)$_d$NHR$^1$, NH(CH$_2$)$_a$NHC(O)(CH$_2$)$_b$(OCH$_2$CH$_2$)$_c$O(CH$_2$)$_d$NHR$^1$, NHC(O)(CH$_2$)$_a$NHR$^1$, NH(CH$_2$)$_a$NHR$^1$, and NHR$^1$. In these formulae, the indices a, b and d are independently selected from the integers from 0 to 20, for example from 1 to 5. The index c is an integer from 1 to about 2500. In an exemplary embodiment, c is selected such that the PEG moiety is approximately 1 kD, 5 kD, 10, kD, 15 kD, 20 kD, 25 kD, 30 kD, 35 kD, 40 kD, 45 kD, 50 kD, 55 kD, 60 kD or 65 kD.

In a more particular embodiment, the c is selected such that the PEG moiety ranges from 15-25 kD, 16-25 kD, 17-25 kD, 18-25 kD, 19-25 kD, 20-25 kD, 21-25 kD, 22-25 kD, 23-25 kD, 24-25 kD, 15-20 kD, 16-20 kD, 17-20 kD, 18-20 kD, 19-20 kD, 20-30 kD, 21-30 kD, 22-30 kD, 23-30 kD, 24-30 kD, 25-30 kD, 26-30 kD, 27-30 kD, 28-30 kD, 29-30 kD. In a still more particular embodiment, the c is selected such that the PEG moiety is 20 kD, 22 kD, 23 kD, 24 kD, 25 kD, 26 kD, 27 kD, 28 kD, 29 kD, or 30 kD.

For the purposes of clarity, the glycosyl linking groups in the remainder of this section are based on a sialyl moiety. However, one of skill in the art will recognize that another glycosyl moiety, such as mannosyl, galactosyl, glucosyl, or fucosyl, could be used in place of the sialyl moiety.

In an exemplary embodiment, the glycosyl linking group is an intact glycosyl linking group, in which the glycosyl moiety or moieties forming the linking group are not degraded by chemical (e.g., sodium metaperiodate) or enzymatic (e.g., oxidase) processes. Selected conjugates of the disclosure include a modifying group that is attached to the amine moiety of an amino-saccharide, e.g., mannosamine, glucosamine, galactosamine, sialic acid etc. In an exemplary embodiment, the disclosure provides a peptide conjugate comprising an intact glycosyl linking group having a formula that is selected from:

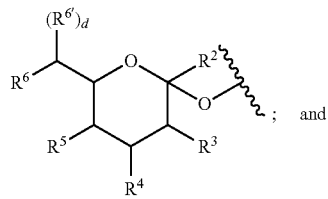
; and

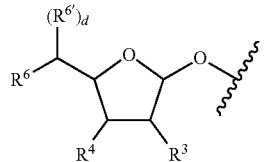

In Formulae I R$^2$ is H, CH$_2$OR$^7$, COOR$^7$ or OR$^7$, in which R$^7$ represents H, substituted or unsubstituted alkyl or substituted or unsubstituted heteroalkyl. When COOR$^7$ is a carboxylic acid or carboxylate, both forms are represented by the designation of the single structure COO$^-$ or COOH. In Formulae I and II, the symbols R$^3$, R$^4$, R$^5$, R$^6$ and R$^{6'}$ independently represent H, substituted or unsubstituted alkyl, OR$^8$, NHC(O)R$^9$. The index d is 0 or 1. R$^8$ and R$^9$ are independently selected from H, substituted or unsubstituted alkyl, substituted or unsubstituted heteroalkyl, sialic acid or polysialic acid. At least one of R$^3$, R$^4$, R$^5$, R$^6$ or R$^{6'}$ includes a modifying group. This modifying group can be a polymeric modifying moiety e.g., PEG, linked through a bond or a linking group. In an exemplary embodiment, R$^6$ and R$^{6'}$, together with the carbon to which they are attached are components of the pyruvyl side chain of sialic acid. In a further exemplary embodiment, the pyruvyl side chain is functionalized with the polymeric modifying group. In another exemplary embodiment, R$^6$ and R$^{6'}$, together with the carbon to which they are attached are components of the side chain of sialic acid and the polymeric modifying group is a component of R$^5$.

Exemplary modifying group-intact glycosyl linking group cassettes according to this motif are based on a sialic acid structure, such as those having the formulae:

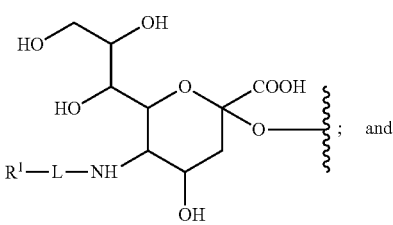
; and

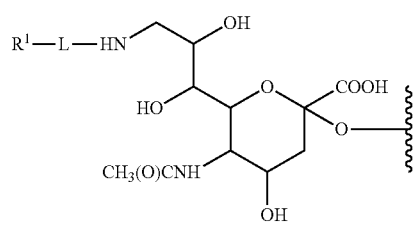

In the formulae above, R$^1$ and L are as described above. Further detail about the structure of exemplary R$^1$ groups is provided below.

In still a further exemplary embodiment, the conjugate is formed between a peptide and a modified sugar in which the modifying group is attached through a linker at the 6-carbon position of the modified sugar. Thus, illustrative glycosyl linking groups according to this embodiment have the formula:

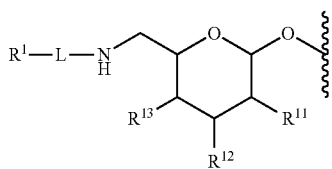

in which the radicals are as discussed above. Glycosyl linking groups include, without limitation, glucose, glucosamine, N-acetyl-glucosamine, galactose, galactosamine, N-acetylgalactosamine, mannose, mannosamine, N-acetyl-mannosamine, and the like.

In one embodiment, the present disclosure provides a mutant FGF-21 peptide conjugate comprising the following glycosyl linking group:

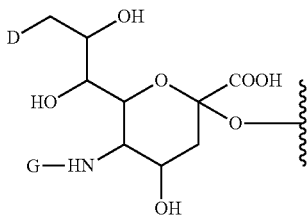

wherein D is a member selected from —OH and $R^1$-L-HN—; G is a member selected from H and $R^1$-L- and —C(O)($C_1$-$C_6$)alkyl; $R^1$ is a moiety comprising a straight-chain or branched poly(ethylene glycol) residue; and L is a linker, e.g., a bond ("zero order"), substituted or unsubstituted alkyl and substituted or unsubstituted heteroalkyl. In exemplary embodiments, when D is OH, G is and when G is —C(O)($C_1$-$C_6$) alkyl, D is $R^1$-L-NH—.

The disclosure provides a peptide conjugate that includes a glycosyl linking group having the formula:

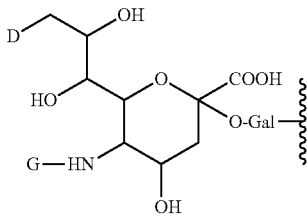

In other embodiments, the glycosyl linking group has the formula:

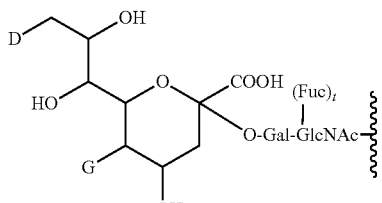

in which the index t is 0 or 1.

In a still further exemplary embodiment, the glycosyl linking group has the formula:

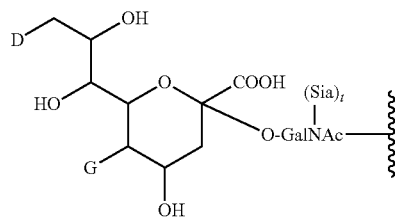

in which the index t is 0 or 1.

In yet another embodiment, the glycosyl linking group has the formula:

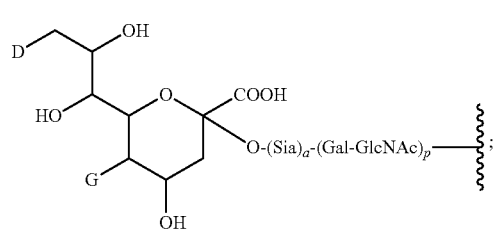

in which the index p represents and integer from 1 to 10; and a is either 0 or 1.

In an exemplary embodiment, a glycoPEGylated peptide conjugate is selected from the formulae set forth below:

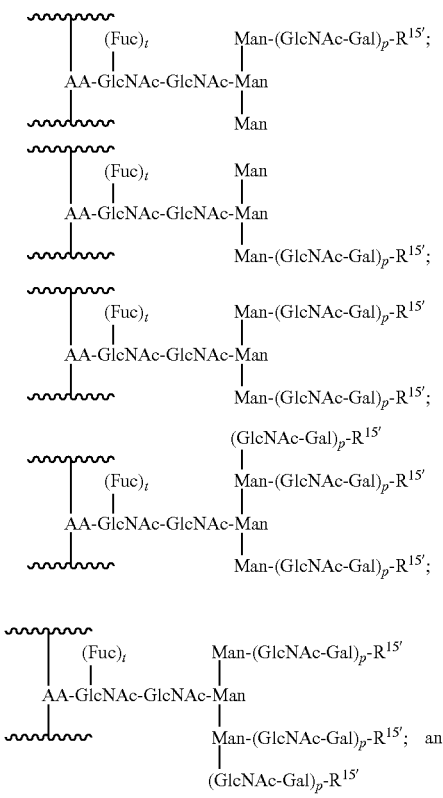

-continued

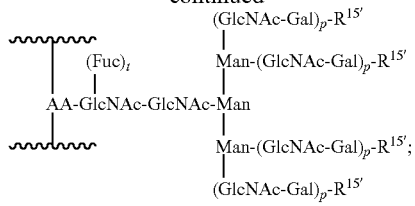

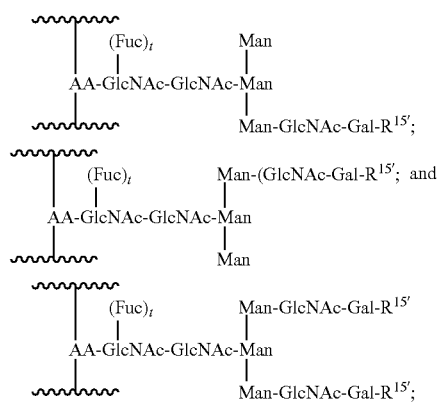

and combinations thereof.

In the formulae above, the index t is an integer from 0 to 1 and the index p is an integer from 1 to 10. The symbol $R^{15'}$ represents H, OH (e.g., Gal-OH), a sialyl moiety, a sialyl linking group (i.e., sialyl linking group-polymeric modifying group (Sia-L-$R^1$), or a sialyl moiety to which is bound a polymer modified sialyl moiety (e.g., Sia-Sia-L-$R^1$) ("Sia-$Sia^P$")). Exemplary polymer modified saccharyl moieties have a structure according to Formulae I and II. An exemplary peptide conjugate of the disclosure will include at least one glycan having a $R^{15'}$ that includes a structure according to Formulae I or II. The oxygen, with the open valence, of Formulae I and II can be attached through a glycosidic linkage to a carbon of a Gal or GalNAc moiety. In a further exemplary embodiment, the oxygen is attached to the carbon at position 3 of a galactose residue.

In an exemplary embodiment, the modified sialic acid is linked α2,3-to the galactose residue. In another exemplary embodiment, the sialic acid is linked α2,6-to the galactose residue.

In an exemplary embodiment, the sialyl linking group is a sialyl moiety to which is bound a polymer modified sialyl moiety (e.g., Sia-Sia-L-$R^1$) ("Sia-$Sia^P$"). Here, the glycosyl linking group is linked to a galactosyl moiety through a sialyl moiety:

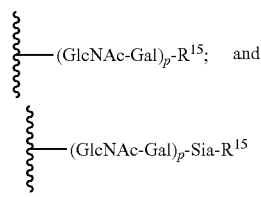

An exemplary species according to this motif is prepared by conjugating Sia-L-$R^1$ to a terminal sialic acid of a glycan using an enzyme that forms Sia-Sia bonds, e.g., CST-11, ST8Sia-II, ST8Sia-III and ST8Sia-IV.

In another exemplary embodiment, the glycans on the peptide conjugates have a formula that is selected from the group:

In each of the formulae above, $R^{15'}$ is as discussed above. Moreover, an exemplary mutant FGF-21 peptide conjugate described herein will include at least one glycan with an $R^{15}$ moiety having a structure according to Formulae I or II.

In another exemplary embodiment, the glycosyl linking group comprises at least one glycosyl linking group having the formula:

$$\begin{array}{l}\xi\!\!-\!(GlcNAc\text{-}Gal)_p\text{-}R^{15}; \quad \text{and} \\ \\ \xi\!\!-\!(GlcNAc\text{-}Gal)_p\text{-}Sia\text{-}R^{15}\end{array}$$

wherein $R^{15}$ is said sialyl linking group; and the index p is an integer selected from 1 to 10.

In an exemplary embodiment, the glycosyl linking moiety has the formula:

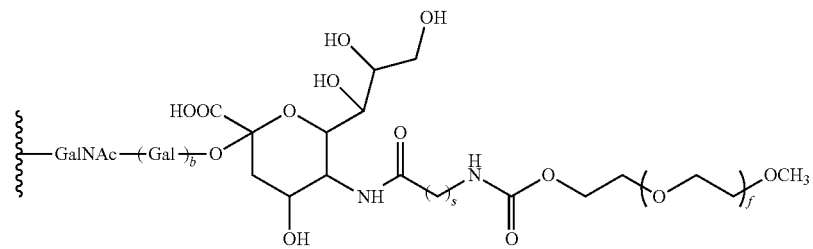

in which b is an integer from 0 to 1. The index s represents an integer from 1 to 10; and the index f represents an integer from 1 to 2500.

In an exemplary embodiment, the polymeric modifying group is PEG. In another exemplary embodiment, the PEG moiety has a molecular weight of 20-30 kDa. In exemplary embodiments, the PEG moiety has a molecular weight of 17 kDa, 18 kDa, 19 kDa, 20 kDa, 21 kDa, 22 kDa, 23 kDa, 24 kDa, 25 kDa, 26 kDa, 27 kDa, 28 kDa, 29 kDa, 30 kDa, 31 kDa, 32 kDa, or 33 kDa. In another exemplary embodiment, the PEG moiety has a molecular weight of 20 kDa. In another exemplary embodiment, the PEG moiety has a molecular weight of 30 kDa. In another exemplary embodiment, the PEG moiety has a molecular weight of about 5 kDa. In another exemplary embodiment, the PEG moiety has a molecular weight of about 10 kDa. In another exemplary embodiment, the PEG moiety has a molecular weight of about 40 kDa.

In an exemplary embodiment, the glycosyl linking group is a linear 10 kDa-PEG-sialyl, and one or two of these glycosyl linking groups are covalently attached to the peptide.

In an exemplary embodiment, the glycosyl linking group is a linear 20 kDa-PEG-sialyl, and one or two of these glycosyl linking groups are covalently attached to the peptide. In an exemplary embodiment, the glycosyl linking group is a linear 30 kDa-PEG-sialyl, and one or two of these glycosyl linking groups are covalently attached to the peptide. In an exemplary embodiment, the glycosyl linking group is a linear 5 kDa-PEG-sialyl, and one, two or three of these glycosyl linking groups are covalently attached to the peptide. In an exemplary embodiment, the glycosyl linking group is a linear 40 kDa-PEG-sialyl, and one or two of these glycosyl linking groups are covalently attached to the peptide.

In a still further exemplary embodiment, a mutant FGF-21 peptide is pegylated in accordance with methods described herein. In a particular embodiment, the mutant FGF-21 peptide comprises the mutations $S^{172}T$ and $R^{176}A$, wherein the positions of the amino acids S and R are based on the amino acid sequence as depicted in SEQ ID NO: 1. More particularly, the mutant FGF-21 peptide comprises the amino acid sequence as depicted in SEQ ID NO: 2. As detailed herein above, the at least one glycosyl moiety attached to the threonine residue and linking the newly introduced threonine residue to the PEG moiety may virtually be any possible glycosyl moiety. The only limitation is that it should be able to attach to threonine and that it should be able to be attached to PEG or m-PEG, more particularly via a linker, e.g. an amino acid residue, particularly glycine. In particular embodiment, the at least one glycosyl moiety comprises N-acetylgalactosamine (GalNAc), galactose (Gal) and/or sialic acid (Sia). In a more particular embodiment, the at least one glycosyl moiety comprises the structure -GalNAc-Sia-, i.e. two glycosyl moieties, namely GalNAc and Sia, wherein the PEG residue may be attached to GalNAc or Sia, particularly to Sia.

The glycosyl moiety which is not attached to the PEG moiety may be attached to the newly introduced threonine residue.

In another particular embodiment, the 20 kDa PEG moiety is attached to the at least one glycosyl linker via a linker, e.g. an amino acid residue, particularly a small amino acid, such as alanine or glycine, more particularly via glycine (Gly). Hence, the PEG or m-PEG moiety is attached to the amino acid and the amino acid is attached to a glycosyl moiety, such as Sia. The glycosyl moiety is attached to the amino acid linker, if present, and to the newly introduced threonine residue in the mutant FGF-21 amino acid sequence. The amino acid residue is attached to PEG and the glycosyl residue via a method described in WO 03/031464 which is incorporated herein by reference.

In a particular embodiment, the mutant FGF-21 peptide (e.g., SEQ ID NO: 2) conjugate comprises the structure -GalNAc-Sia-Gly-PEG(20 kDa), wherein GalNAc is attached, e.g. to a newly introduced threonine residue and to Sia. Sia is further attached via a glycine residue to a PEG of 17 kDa, 18 kDa, 19 kDa, 20 kDa, 21 kDa, 22 kDa, 23 kDa, 24 kDa, 25 kDa, 26 kDa, 27 kDa, 28 kDa, 29 kDa, 30 kDa, 31 kDa, 32 kDa, or 33 kDa.

In a more particular embodiment, the mutant FGF-21 peptide (e.g., SEQ ID NO: 2) conjugate comprises the structure -GalNAc-Sia-Gly-PEG(20 kDa), wherein GalNAc is attached, e.g. to a newly introduced threonine residue and to Sia. Sia is further attached via a glycine residue to a PEG of 20 kDa, 21 kDa, 22 kDa, 23 kDa, 24 kDa, 25 kDa, 26 kDa, 27 kDa, 28 kDa, 29 kDa, or 30 kDa.

In a still more particular embodiment, the mutant FGF-21 peptide (e.g., SEQ ID NO: 2) conjugate comprises the structure -GalNAc-Sia-Gly-PEG(20 kDa), wherein GalNAc is attached, e.g. to a newly introduced threonine residue and to Sia. Sia is further attached via a glycine residue to a PEG of 20 kDa, 25 kDa, or 30 kDa.

In a further particular embodiment, the mutant FGF-21 peptide (e.g., SEQ ID NO: 2) conjugate comprises the structure -GalNAc-Sia-Gly-PEG(20 kDa), wherein GalNAc is attached, e.g. to a newly introduced threonine residue and to Sia. Sia is further attached via a glycine residue to a PEG of 20 kDa or 30 kDa.

In a still further particular embodiment, the mutant FGF-21 peptide (e.g., SEQ ID NO: 2) conjugate comprises the structure -GalNAc-Sia-Gly-PEG(20 kDa), wherein GalNAc is attached, e.g. to a newly introduced threonine residue and to Sia. Sia is further attached via a glycine residue to a PEG of 20 kDa.

In a very particular embodiment, the mutant FGF-21 peptide conjugate comprises the structure:

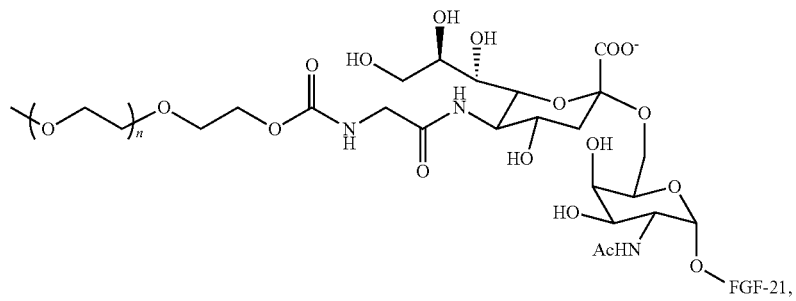

wherein n is an integer selected from 450 to 460 as also depicted in FIG. 1.

The 20 kDa PEG may be linear or branched, more particularly the 20 kDa PEG, is a linear 20 kDa PEG. Further, the 20 kDa PEG is particularly a 20 kDa methoxy-PEG (mPEG, m-PEG). PEG and mPEG of different molecular weight can be obtained from various suppliers, such as from JenKem Technology USA, Plano, TX, USA, or Merckle Biotec, Ulm, Germany. It is understood in the art that PEG 20 kDa means that the size of the PEG residues is 20 kDa in average and that the majority of the PEG residues are 20 kDa in size.

Mutant FGF-21 Peptides and Conjugates Thereof

Variants of Fibroblast Growth Factor-21 (FGF-21) having surprising properties, including variants having exceptionally long half-lives, are provided which variants are peptide conjugates comprising
i) a mutant FGF-21 peptide comprising at least one threonine (T) residue adjacent to at least one proline (P) residue on the C-terminal side of the at least one proline residue, thereby forming at least one O-linked glycosylation site which does not exist in the corresponding native FGF-21, wherein the corresponding native FGF-21 has an amino acid sequence that is at least 95% identical to SEQ ID NO: 1, and
ii) a 20-30 kDa polyethylene glycol (PEG), wherein said 20-30 kDa PEG is covalently attached to said mutant FGF-21 peptide at the at least one threonine residue via at least one glycosyl moiety.

For the attachment of the 20-30 kDa PEG residue, a threonine residue is introduced into the amino acid sequence of native FGF-21 adjacent to and on the C-terminal side of a proline residue which is already present in the amino acid sequence of native FGF-21, i.e. is a native proline residue. For this purpose, either (i) an additional threonine may be introduced immediately next to the native proline residue or (ii) the native amino acid which is present in the native amino acid sequence of FGF-21 adjacent to and located on the C-terminal side of a native proline residue is exchanged for a threonine residue. In the present disclosure, option (ii) is an exemplary embodiment. As described herein, more than one threonine residue may be introduced adjacent and C-terminal to a proline residue which is already present. A mutant FGF-21 of the present disclosure may thus comprise both threonine residues which have been additionally introduced and threonine residues which have been introduced instead of a native amino acid.

By the introduction of a new threonine residue on the C-terminal side and adjacent to a proline residue, a consensus sequence for O-glycosylation enzyme is formed. Because proline residues are typically found on the surface of proteins (in, e.g., turns, kinks, and/or loops), a design that calls for O-glycosylation and PEGylation thereto using a PEG-glycosyl moiety in close proximity to a proline residue benefits from the relative accessibility of the target attachment site for the glycosyl transferase that transfers the glycosyl or glycol-PEG moiety and the potential to accommodate the conjugated glycosyl and/or PEG structure without disruption of protein structure.

For introduction of the threonine residues into the native amino acid sequence of FGF-21, routine techniques in the field of recombinant genetics are used. Basic texts disclosing the general methods of use in this disclosure include Sambrook and Russell, Molecular Cloning, A Laboratory Manual (3rd ed. 2001); Kriegler, Gene Transfer and Expression: A Laboratory Manual (1990); and Ausubel et al., eds., Current Protocols in Molecular Biology (1994).

In a particular embodiment, the native FGF-21 amino acid sequence corresponds to the native amino acid sequence of human FGF-21 depicted in SEQ ID NO: 1.

In a particular embodiment, the mutant FGF-21 peptide comprises the amino acid sequence PT, i.e. a threonine residue C-terminally adjacent to a proline residue. The sequence PT is not present in the native FGF-21 amino acid sequence.

Optionally, the mutant FGF-21 peptide comprises at least one amino acid sequence selected from the group consisting of $P^{172}T$ (e.g. SEQ ID NO: 2 or 3), $P^{156}T$ (e.g. SEQ ID NO: 4), PST (e.g. SEQ ID NO: 5), $P^{3}T$ (e.g. SEQ ID NO: 6), $P^{9}T$ (e.g. SEQ ID NO: 7), $P^{50}T$ (e.g. SEQ ID NO: 8), $P^{61}T$ (e.g. SEQ ID NO: 9), $P^{79}T$ (e.g. SEQ ID NO: 10), $P^{91}T$ (e.g. SEQ ID NO: 11), $P^{116}T$ (e.g. SEQ ID NO: 12), $P^{120}T$ (e.g. SEQ ID NO: 13), $P^{125}T$ (e.g. SEQ ID NO: 14), $P^{129}T$ (e.g. SEQ ID NO: 15), $P^{131}T$ (e.g. SEQ ID NO: 16), $P^{134}T$ (e.g. SEQ ID NO: 17), $P^{139}T$ (e.g. SEQ ID NO: 18), $P^{141}T$ (e.g. SEQ ID NO: 19), $P^{144}T$ (e.g. SEQ ID NO: 20), $P^{145}T$ (e.g. SEQ ID NO: 21), $P^{148}T$ (e.g. SEQ ID NO: 22), $P^{150}T$ (e.g. SEQ ID NO: 23), $P^{151}T$ (e.g. SEQ ID NO: 24), $P^{158}T$ (e.g. SEQ ID NO: 25), $P^{159}T$ (e.g. SEQ ID NO: 26), $P^{166}T$ (e.g. SEQ ID NO: 27), $P^{178}T$ (e.g. SEQ ID NO: 28), and combinations thereof, wherein the positions of proline and threonine are based on the native amino acid sequence of FGF-21 as depicted in SEQ ID NO: 1, particularly the mutant FGF-21 peptide comprises at least one amino acid sequence selected from the group consisting of $P^{172}T$, $P^{156}T$, $P^{5}T$ and combinations thereof, more particularly consisting of $P^{172}T$, $P^{156}T$ and combinations thereof, and even more particularly the mutant FGF-21 peptide comprises the sequence motif $P^{172}T$, based on the amino acid sequence as depicted in SEQ ID NO: 1, wherein the positions of proline and threonine are based on the amino acid sequence as depicted in SEQ ID NO: 1.

In a particular embodiment, the proline residue is located between amino acid 145 and the C-terminus of the mutant FGF-21 peptide, wherein the position of amino acid 145 is based on the amino acid sequence as depicted in SEQ ID NO: 1. As demonstrated by results presented herein, the C-terminus of FGF-21 surprisingly tolerates attachment of PEG and in particular of glycosyl-PEG moieties. This was unexpected since the literature reports that the intact C-terminus is necessary for β-Klotho binding of FGF-21.

In a particular embodiment, the mutant FGF-21 peptide comprises the mutations $S^{172}T$ and $R^{176}A$, wherein the positions of the amino acids S and R are based on the amino acid sequence as depicted in SEQ ID NO: 1, particularly the mutant FGF-21 peptide comprises the amino acid sequence as depicted in SEQ ID NO: 2. The mutation $R^{176}A$ has been found beneficial to the protein's overall stability after introducing the O-linked glycosylation site at threonine 173. By this mutation, the relatively large arginine side chain was removed and replaced by the small side chain of alanine. It is assumed that the smaller side chain of alanine interferes less with the voluminous glycosyl-PEG moiety to be attached to thindicae mutated FGF-21 peptide.

In an alternative embodiment, the mutant FGF-21 peptide comprises the mutation $Q^{157}T$, wherein the position of the amino acid Q is based on the amino acid sequence as depicted in SEQ ID NO: 1, particularly the mutant FGF-21 peptide comprises the amino acid sequence as depicted in SEQ ID NO: 4, or the mutation D6T, wherein the position of the amino acid D is based on the amino acid sequence as depicted in SEQ ID NO: 1, particularly the mutant FGF-21 peptide comprises the amino acid sequence as depicted in SEQ ID NO: 5.

In a particular embodiment, the mutant FGF-21 peptide conjugate comprises an amino acid sequence selected from the group consisting of SEQ ID NOs: 2 to 28. In some embodiments, the mutant FGF-21 peptide comprises an amino acid sequence selected from the group consisting of SEQ ID NOs: 2 to 5. In some embodiments, the mutant FGF-21 peptide comprises an amino acid sequence selected from the group consisting of SEQ ID NOs: 2 to 4. In some embodiments, the mutant FGF-21 peptide comprises an amino acid sequence as depicted in SEQ ID NO: 2.

Further provided is a liquid pharmaceutical composition comprising the mutant FGF-21 peptide conjugate and a pharmaceutically acceptable carrier, such as water or a physiologically compatible buffer. The liquid pharmaceutical composition typically comprises a therapeutically effective or pharmaceutically active amount of the mutant FGF-21 peptide conjugate as active agent.

In some embodiments, the liquid pharmaceutical composition further comprising one or more active agent. In some embodiments, the one or more agent can comprise a peptide, a small molecule or combinations thereof. In some embodiments, the one or more agent can comprise an hormone. For example, the one or more agents can comprise oxyntomodulin, insulin, leptin, glucagon. eroxisome proliferator-activated receptor (PPAR) agonists, FXR (Farnesoid X receptor) agonists, Thyroid Hormone Receptor-Beta (TRβ) Agonists, Sodium glucose co-transporter 2 (SGLT2) Inhibitors, analogs thereof, or combinations thereof.

Liquid pharmaceutical compositions of the disclosure are suitable for use in a variety of drug delivery systems. Suitable formulations for use in the present disclosure are found in Remington's Pharmaceutical Sciences, Mack Publishing Company, Philadelphia, PA, 17$^{th}$ ed. (1985). For a brief review of methods for drug delivery, see, Langer, Science 249: 1527-1533 (1990). The pharmaceutical compositions are intended for parenteral, intranasal, topical, oral, or local administration, such as by subcutaneous injection, aerosol inhalation, or transdermal adsorption, for prophylactic and/or therapeutic treatment. In some embodiments, the liquid pharmaceutical compositions are administered by injection. In some embodiments, the liquid pharmaceutical compositions are administered parenterally, e.g., subcutaneously or intravenously. According to aspects of the disclosure, the liquid pharmaceutical compositions are administered by subcutaneous injection. Thus, aspects of the disclosure provide compositions for parenteral administration (e.g. subcutaneous injection) which comprise the mutant FGF-21 peptide conjugate dissolved or suspended in an acceptable carrier. The carrier can be an aqueous carrier, e.g., water, buffered water, saline, phosphate buffered saline (PBS) and the like. The compositions may also contain detergents such as Tween 20 and Tween 80; stabilizers such as mannitol, sorbitol, sucrose, and trehalose; and preservatives such as EDTA and m-cresol. The compositions may contain pharmaceutically acceptable auxiliary substances as required to approximate physiological conditions, such as pH adjusting and buffering agents, tonicity adjusting agents, wetting agents, detergents and the like.

The liquid pharmaceutical compositions of the disclosure may be sterilized by conventional sterilization techniques, or may be sterile filtered. The resulting aqueous solutions may be packaged for use as is, or lyophilized, the lyophilized preparation being combined with a sterile aqueous carrier prior to administration. The compositions containing the FGF peptide conjugates can be administered for prophylactic and/or therapeutic treatments, in particular for the treatment of diabetes or diabetes related diseases, particularly for the treatment of diabetes type 2, NASH and metabolic syndrome. In therapeutic applications, compositions are administered to a subject already suffering from a disease or condition related to diabetes, in an amount sufficient to cure or at least partially arrest the symptoms of the disease and its complications. An amount adequate to accomplish this is defined as a "therapeutically effective amount" and usually depends on the patient's state of health and weight.

The present disclosure provides methods for treating a disease and/or a disorder or symptoms thereof which comprise administering a liquid pharmaceutical composition comprising same to a subject (e.g., a mammal such as a human). Thus, one embodiment is a method for treating a subject suffering from diabetes or a diabetes related disease (e.g., diabetes type 2, NASH or metabolic syndrome) or a symptom thereof. The method includes the step of administering to the mammal an amount of a compound described herein in an amount sufficient to treat the disease or disorder or symptom thereof or a composition comprising same, under conditions such that the disease or disorder is treated.

Single or multiple administrations of the liquid compositions can be carried out with dose levels and pattern being selected by the treating physician. In any event, the liquid pharmaceutical compositions should provide a quantity of the mutant FGF-21 peptide conjugate of this disclosure sufficient for an effective treatment of the subject in need of such treatment.

In another aspect, a method for treating diabetes and related diseases, particularly diabetes type 2, non-alcoholic steatohepatitis (NASH) and/or metabolic syndrome is presented, the method comprising administering to a subject in need thereof a liquid pharmaceutical composition comprising at least one of the mutant FGF-21 peptide conjugates described herein. In a particular embodiment, the subject in need thereof is a human subject.

In the liquid pharmaceutical composition, the mutant FGF-21 peptide conjugate is typically present in a concentration in the range from about 0.1 mg/mL to about 50 mg/mL, for example about 10 mg/mL to about 48 mg/mL, about 20 mg/mL to about 44 mg/mL, for example about 20 mg/mL, about 28 mg/mL, about 36 mg/mL, about 44 mg/mL.

All components of the liquid pharmaceutical composition as well as the specific concentrations of the components have carefully selected after testing very many different conditions, compounds and concentrations thereof. Hence, the pharmaceutical composition disclosed herein is not an arbitrary selection of compounds and compound concentrations but a specific and rational selection of conditions which have been found to be most optimal for an aqueous pharmaceutical composition containing the mutant FGF-21 peptide conjugate or mutant FGF-21 peptide according to the disclosure for use as a medicament.

In some embodiments, the liquid pharmaceutical composition comprises a buffering agent, particularly a phosphate or Tris buffer, e.g. Tris(hydroxymethyl)aminomethane (THAM). Optionally, the buffering agent is present in a concentration from 1 mM to 100 mM, from 2 mM to 75 mM, from 5 mM to 50 mM, from 10 mM to 25 mM. from 5 to 25 mM Tris buffer was selected since solubility of the protein was found to be better than for other buffer systems and it is suitable to keep the pH at 7-8, for example pH 7.5+/−0.4 (e.g. 7.0, 7.1, 7.2, 7.3, 7.4, 7.5, 7.6, 7.7, 7.8 or 7.9.) In some embodiments, the liquid pharmaceutical composition comprises a about 20 mM Tris buffer. This pH seems the most optimal one for prolonged storage of the PEGylated mutant FGF-21 peptide conjugate. Moreover, probability of Tris crystallization at lower temperatures is lower than that of phosphate based buffering agents.

In some embodiments, the pH of the pharmaceutical composition is in the range from 6.0 to 8.5, from 6.5 to 8.0, from 6.75 to 8.0, from 7.0 to 8.0, from 7.0 to 8.0 for example 7.5±0.5 as lowest fragmentation in SDS-PAGE and least aggregation in SEC was observed if the pH is in the range of 7-8. This pH has also been identified to be optional with respect to viscosity. As the pH of a solution may depend on the temperature of the solution, the pH should particularly be adapted and measured at 25±2° C. The pH may be adjusted with HCl.

The pharmaceutical composition may further comprise a tonicity modifying agent. The tonicity modifying agent may be selected from the group consisting of glycerol, amino acids, sodium chloride, proteins, sugars and sugar alcohols. A tonicity modifying agent, in particular arginine, was found to have an advantageous effect on the pharmaceutical composition as it reduces aggregation of the active agent, namely the mutant FGF-21 peptide (conjugate).

The tonicity modifying agent, for example arginine, may be present in a concentration of about 150 mM to about 500 mM, about 150 mM to about 275 mM, about 220 mM to about 270 mM, 2 about 00 mM to about 260 mM, about 200 mM to about 230 mM. For example, arginine HCl can be present at a concentration of about 150, 160, 170, 180, 190, 200, 210, 220, 230, 240, 250, 260, or 270 mM Further, the pharmaceutical composition may comprise a surfactant, particularly a non-ionic surfactant. The surfactant or non-ionic surfactant particularly is a polysorbate-based non-ionic surfactant. In some embodiments, the surfactant is polysorbate 20 or polysorbate 80. The surfactant or non-ionic surfactant, for example polysorbate 20 or 80 is optionally present in a concentration of 0.01 mg/mL to 1 mg/mL, 0.05 to 0.5 mg/mL, or 0.2±0.02 mg/mL. In some embodiments, the surfactant is polysorbate 80. In some embodiments, the surfactant is present in a concentration of 0.2±0.02 mg/mL. For example, the surfactant can be present in a concentration of about 0.18, 0.19, 0.2, 0.21, 0.22 mg/mL. In some embodiments, the surfactant, such as the polysorbate-based non-ionic surfactant protect from shear forces that can cause aggregation.

Also provided herein is a pharmaceutical container comprising the liquid pharmaceutical composition of the disclosure. In some embodiments, the pharmaceutical container is a syringe, autoinjector, vial, infusion bottle, ampoule, carpoule, a syringe equipped with a needle protection system, or a carpoule within an injection pen.

Manufacture

In some embodiments, the method is as follows: First the mutation which introduces the threonine adjacent to and on the C-terminal side of a proline residue and optionally one or more further mutations are introduced into a nucleic acid sequence encoding for native or mutated FGF-21, such as of human FGF-21 as in SEQ ID NO: 1. The nucleic acid sequence encoding the mutated FGF-21 peptide is the introduced into an expression vector suitable for protein expression in an expression host. Methods for introducing mutations into nucleic acid sequences, such as site-directed mutagenesis, and the incorporation of the mutated nucleic acid sequence into an expression vector are well known to the skilled person (cf. e.g., "A Guide to Methods in the Biomedical Sciences" by R.B. Corley, Springer Science & Business Media, 2006).

After protein expression, optional purification, the PEG residue is attached to the mutant FGF-21 peptide, specifically at the newly introduced threonine residue via at least one glycosyl moiety and optionally via at least one amino acid residue which is present between the PEG and the glycosyl residue.

To obtain high yield expression of a nucleic acid encoding a mutant FGF-21 of the present disclosure, one typically subclones a polynucleotide encoding the mutant Fibroblast Growth Factor into an expression vector that contains a strong promoter to direct transcription, a transcription/translation terminator and a ribosome binding site for translational initiation. Suitable bacterial promoters are well known in the art and described, e.g., in Sambrook and Russell, supra, and Ausubel et al, supra. Bacterial expression systems for expressing the native or mutant FGF-21 are available in, e.g., *Escherichia coli* (*E. coli*), *Bacillus* sp., *Salmonella*, and *Caulobacter*. Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector. In some embodiments, the mutant FGF-21 peptide is recombinantly produced in *E. coli* cells, i.e. the expression host is *E. coli*.

An exemplary method of production is described in this paragraph: The mutant FGF-21 peptide is expressed in *E. coli* as inclusion bodies. Cells are recovered from the harvest by centrifugation, disrupted, and inclusion bodies are washed and recovered by centrifugation. Purification of the non-PEGylated mutant FGF-21 peptide begins with solubilizing the mutant FGF-21 peptide from the inclusion bodies and refolding of the peptide. The refolded mutant FGF-21 peptide is filtered and purified by two anion exchange chromatography operations, both utilizing Eshmuno Q chromatography resin and operated in bind and elute mode. If necessary, the purified mutant FGF-21 peptide may be concentrated by ultrafiltration using Pellicon 2 (5 kD MWCO) membranes. The purified mutant FGF-21 peptide is dispensed into sterile PETG bottles and may be stored at ≤−70° C. See FIG. 2 and FIG. 3.

Figure 2:
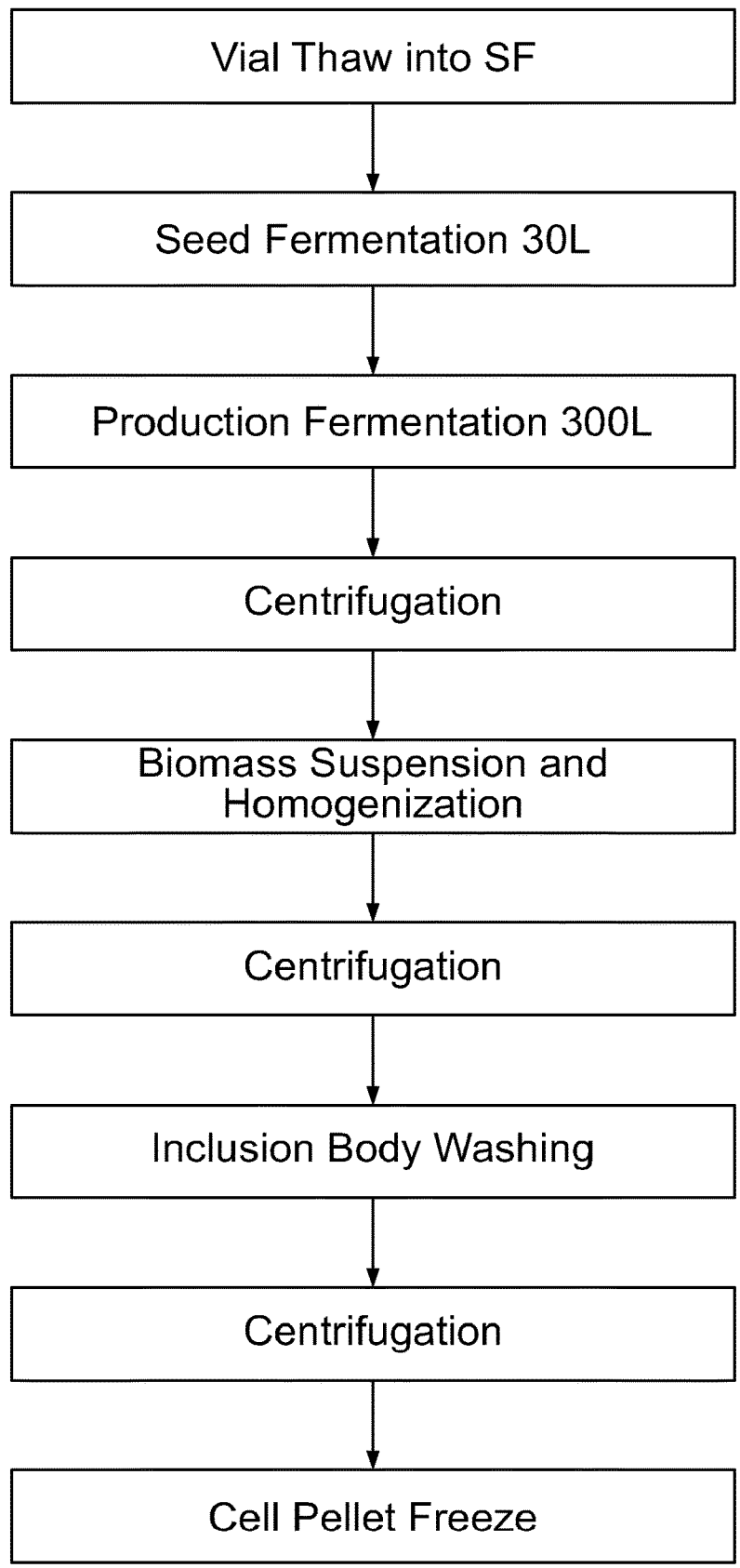
FIG. 2 shows a non-limiting exemplary cell expansion, production, and harvest process flow diagram according to some embodiments.
Figure 3:
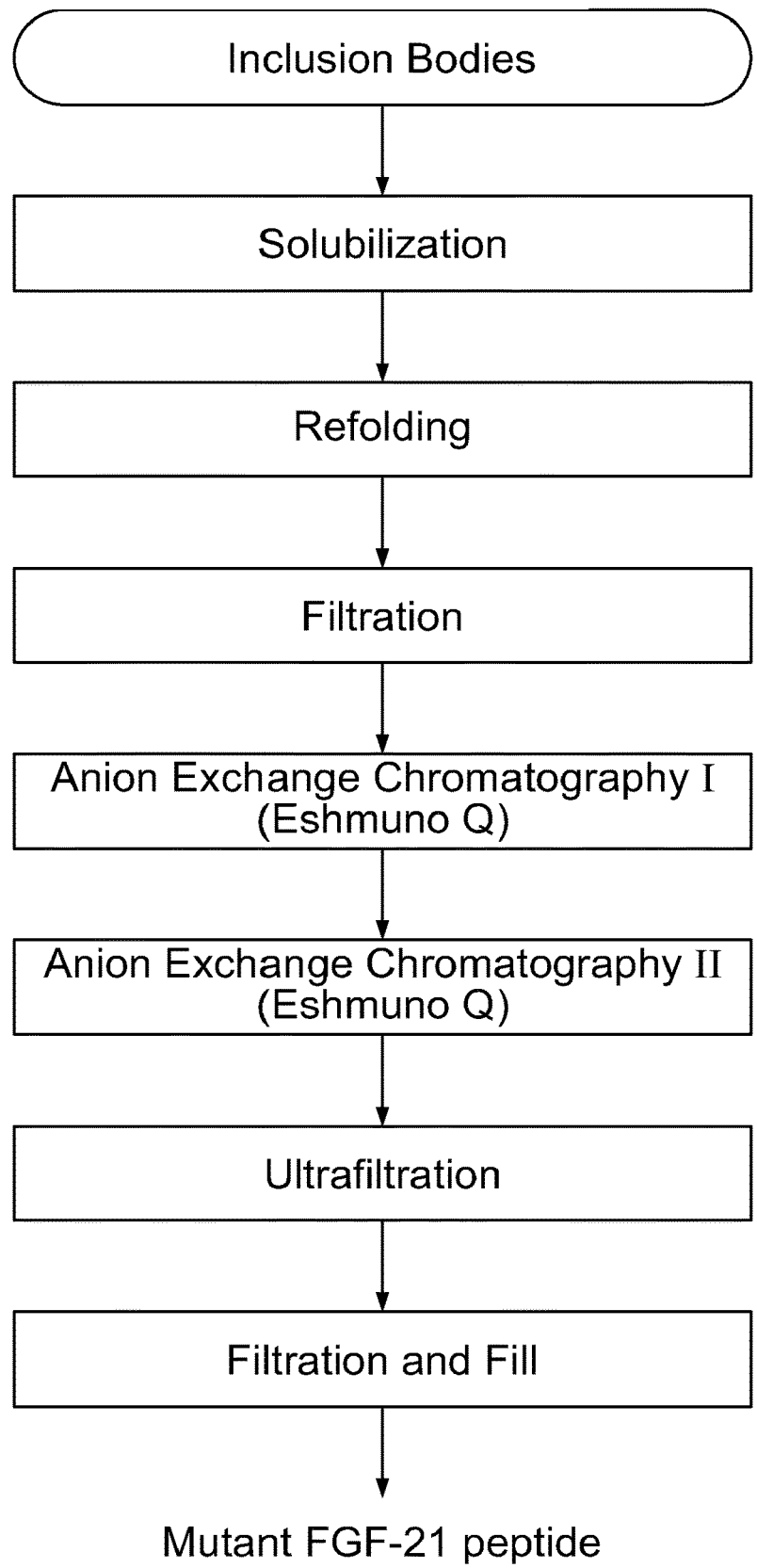
FIG. 3 shows a non-limiting exemplary refolding and mutant FGF-21 peptide purification process flow diagram according to some embodiments.
Figure 4:
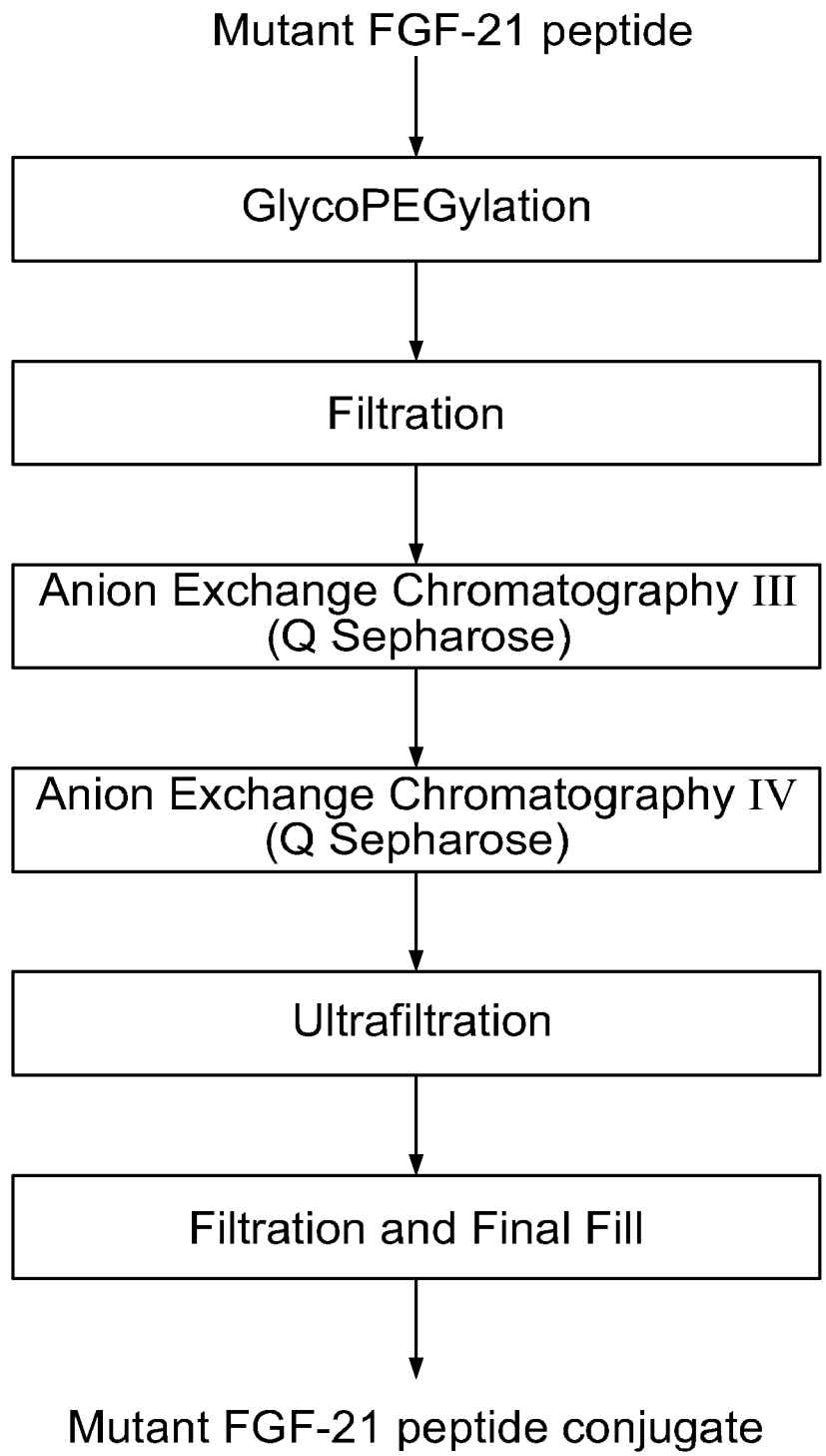
FIG. 4 shows a non-limiting exemplary GlycoPEGylation and final purification process flow diagram according to some embodiments.
Figure 5:
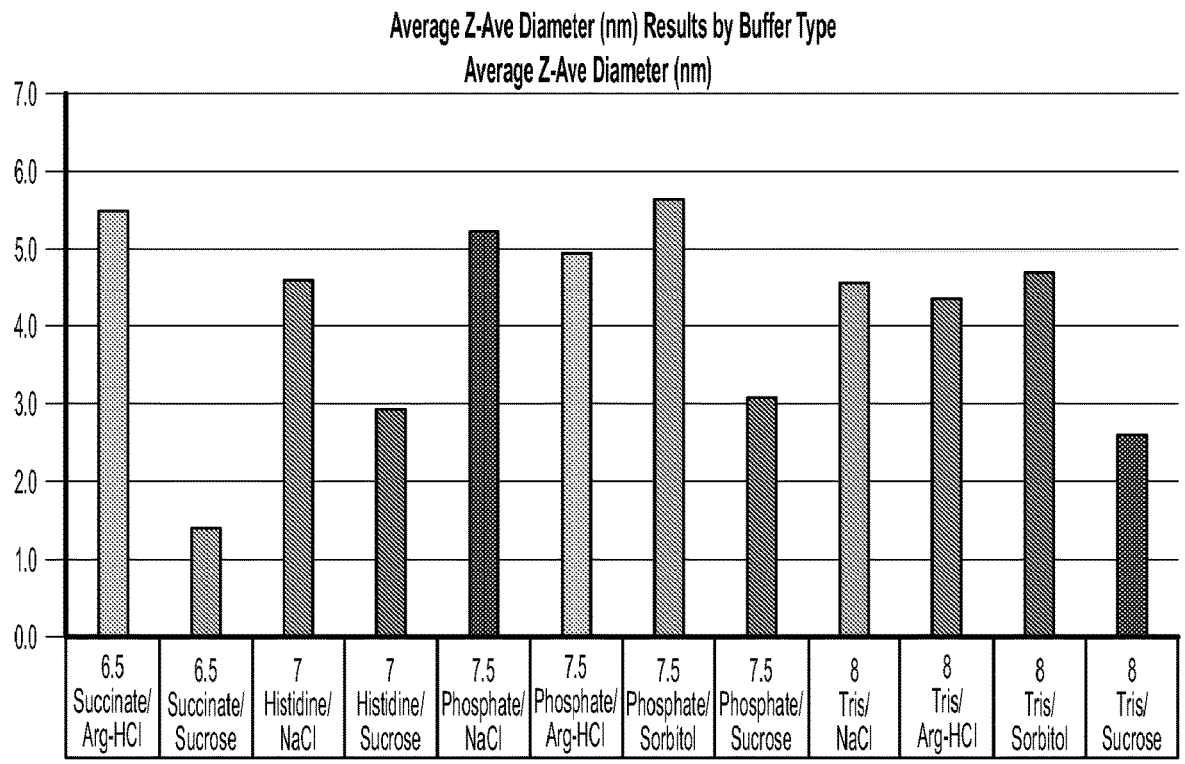
FIG. 5 shows the average Z-Ave Diameter (nm) Results by buffer type according to some embodiments.
Figure 6:
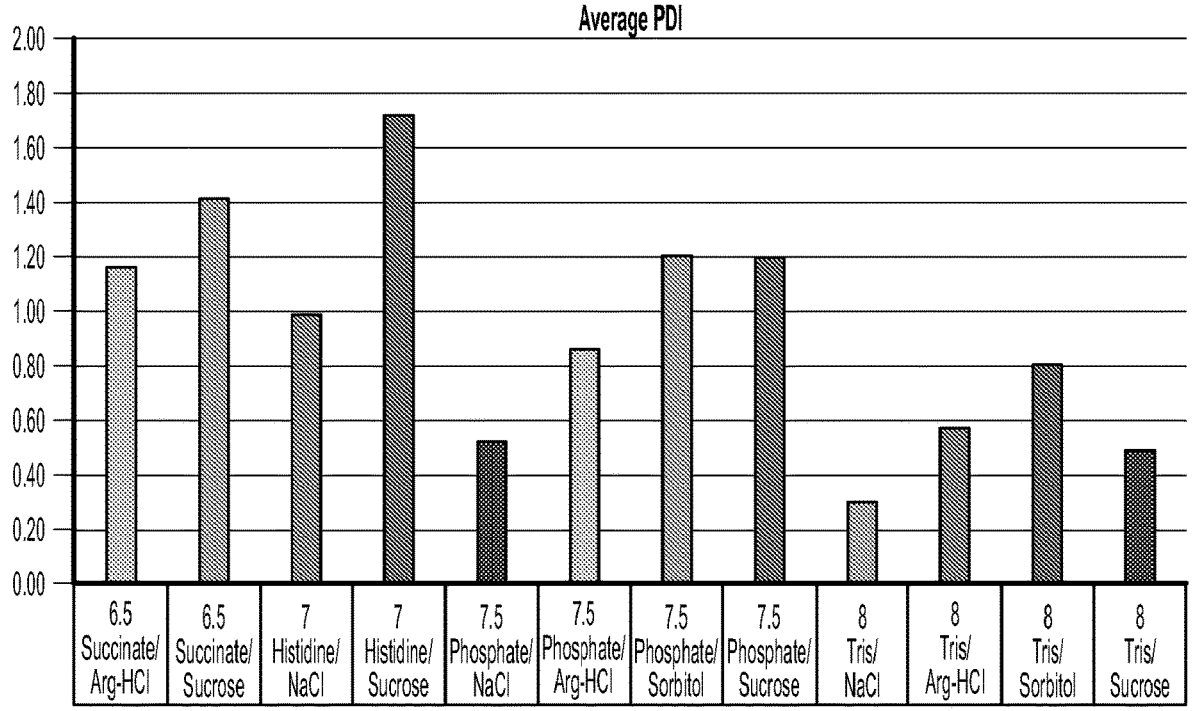
FIG. 6 shows average Polydispersity Index (PDI) Results by buffer according to some embodiments.
Figure 7:
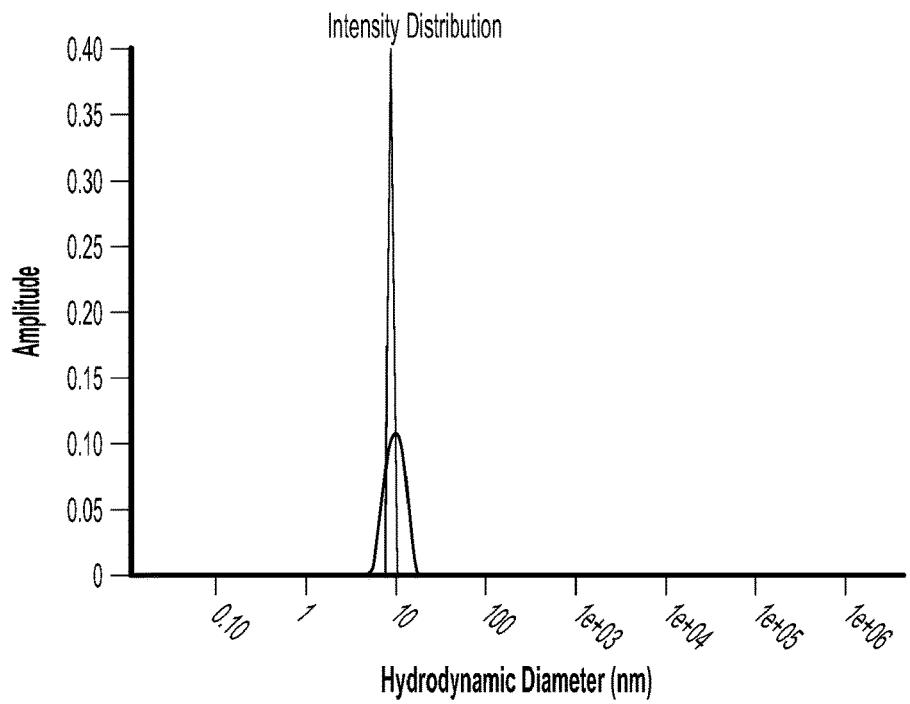
FIG. 7 shows the overlay of three sample traces obtained for the 20 mM Tris, 150 mM Arg-HCl pH 8.0 demonstrating acceptable polydispersity according to some embodiments.
Figure 8:
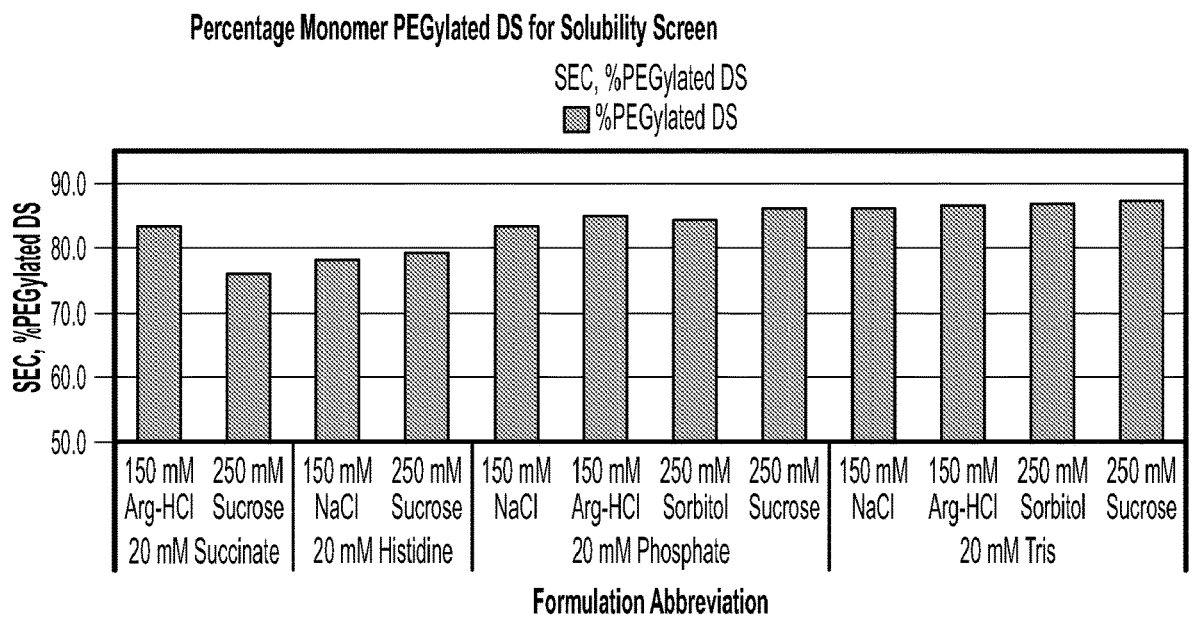
FIG. 8 shows the percentage monomer PEGylated DS for solubility screen according to some embodiments.
Figure 9:
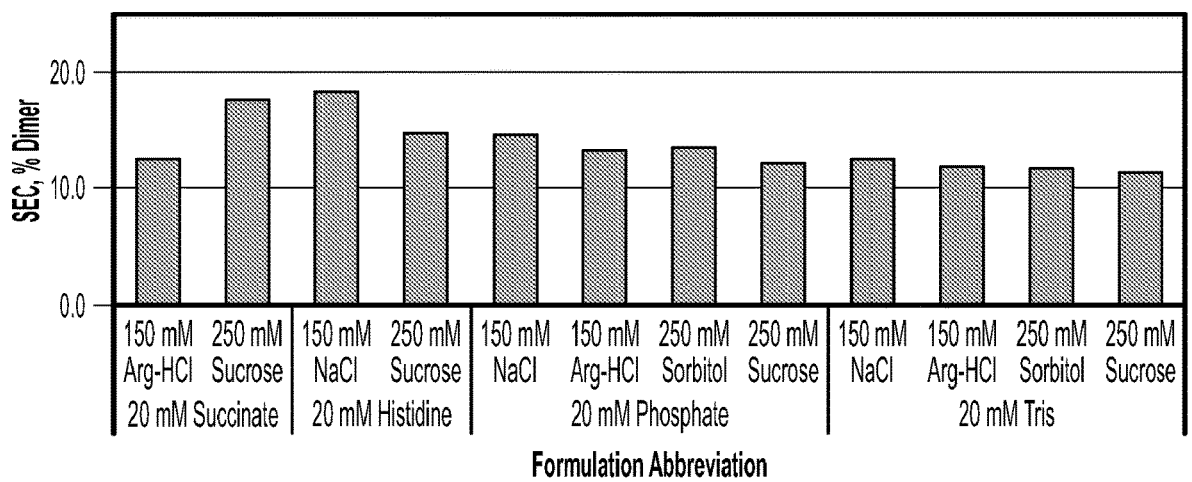
FIG. 9 shows the percentage dimers PEGylated DS for solubility screen according to some embodiments.
Figure 10:
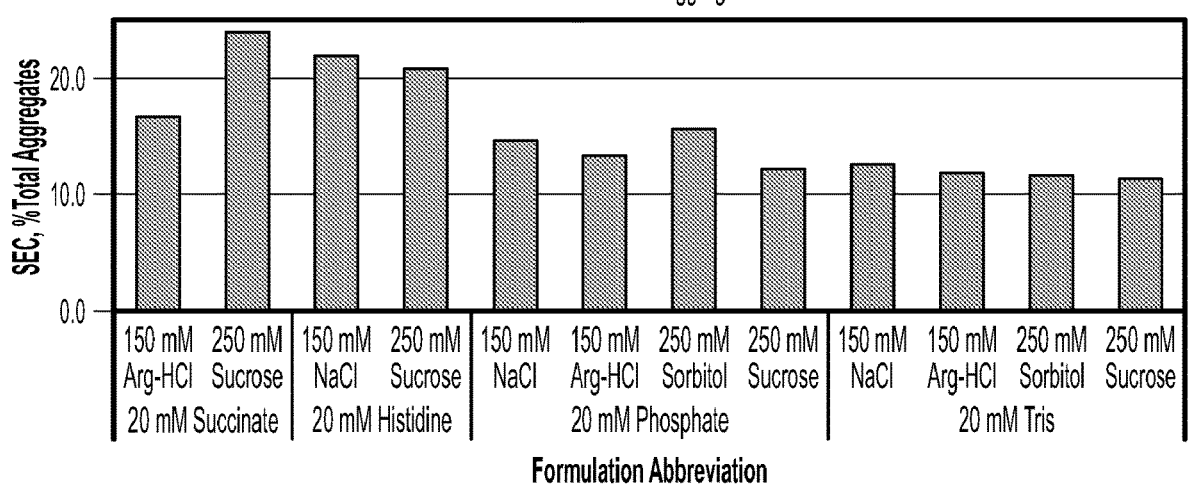
FIG. 10 shows the percentage total aggregates PEGylated DS for solubility screen according to some embodiments.
Figure 11:
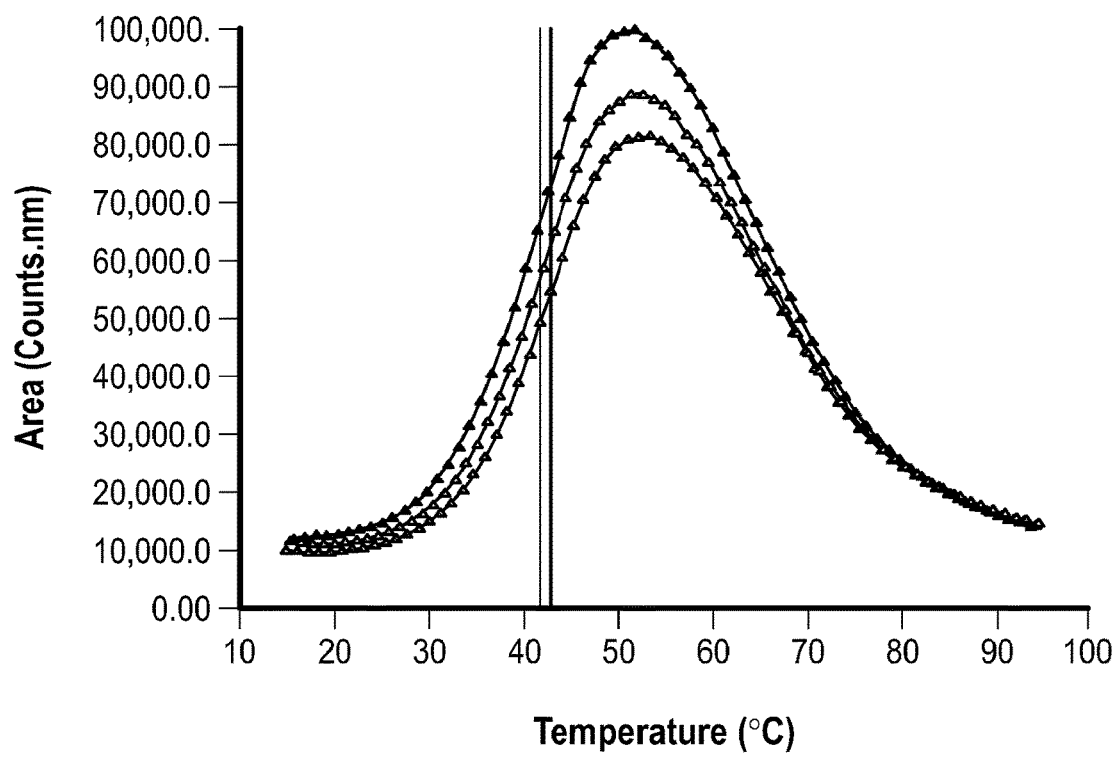
FIG. 11 shows the overlay of three sample traces obtained for the 20 mM Tris, 150 mM Arg-HCl pH 8.0, with lines indicating Tm for each of the triplicate readings according to some embodiments.
Figure 12:
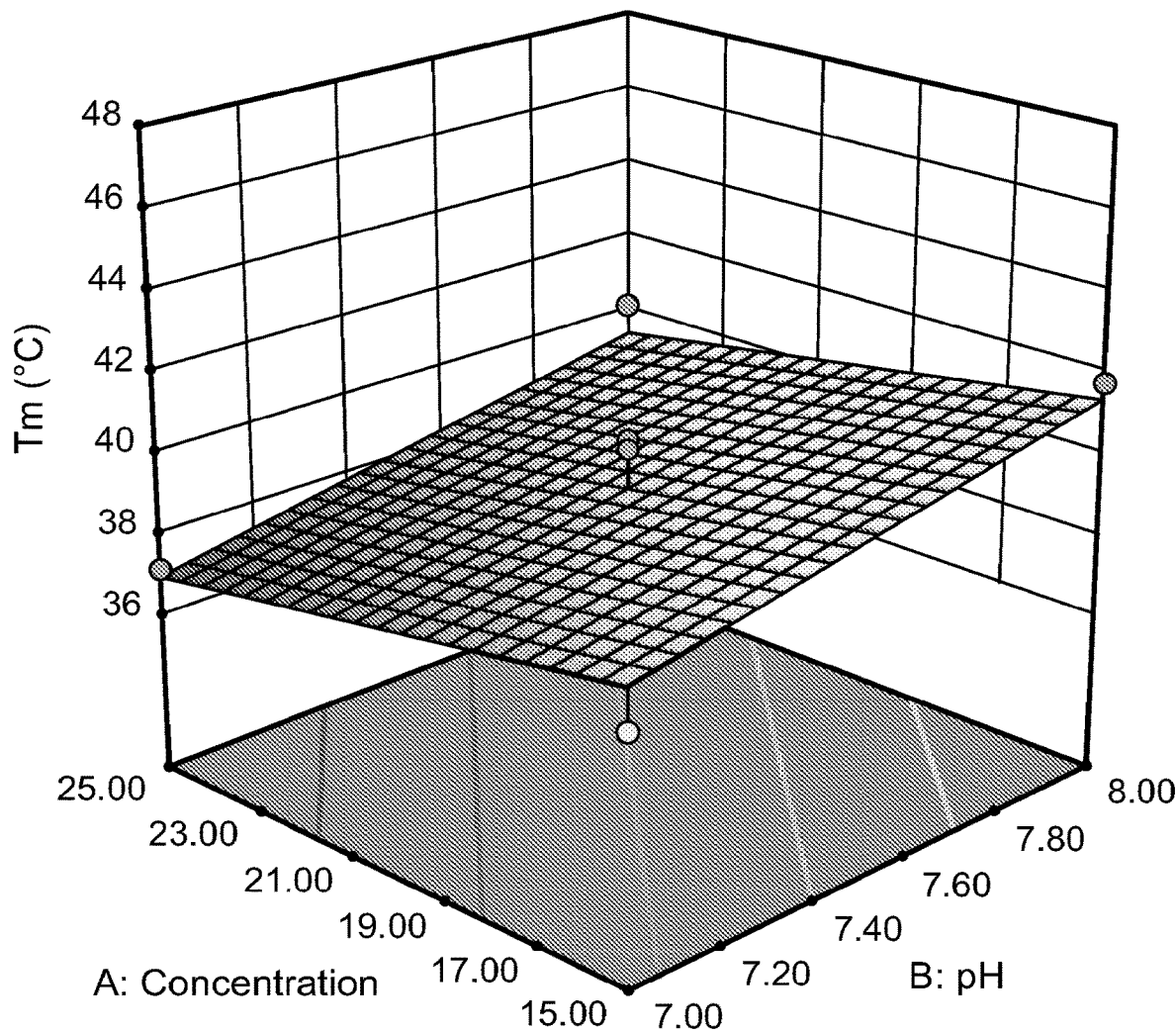
FIG. 12 shows a 3D surface plot for Differential scanning fluorimetry (DSF) T0 according to some embodiments.
Figure 13:
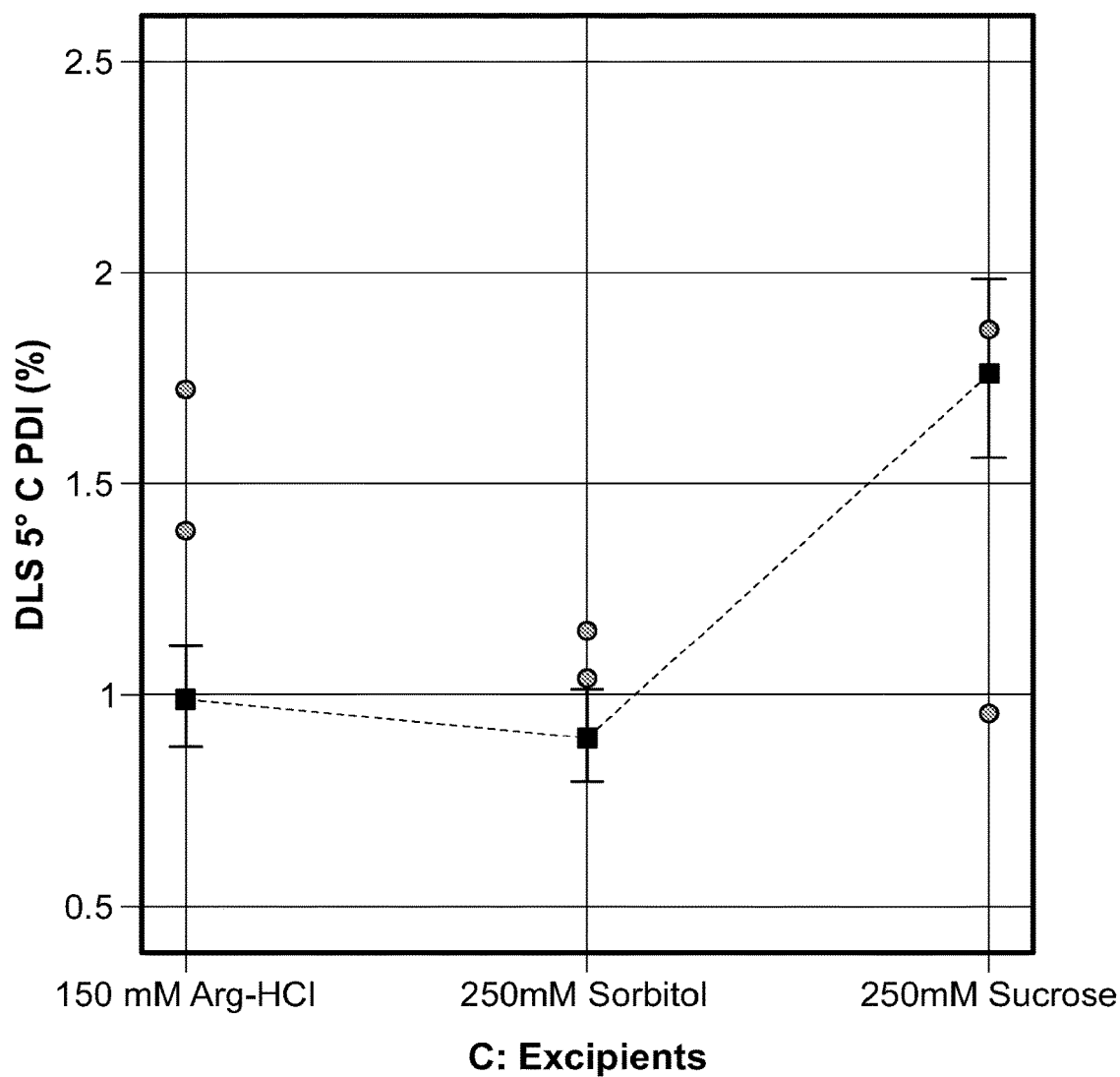
FIG. 13 shows dynamic light scattering (DLS) 2 W/5° C. Overall PDI according to some embodiments.
Figure 14A:
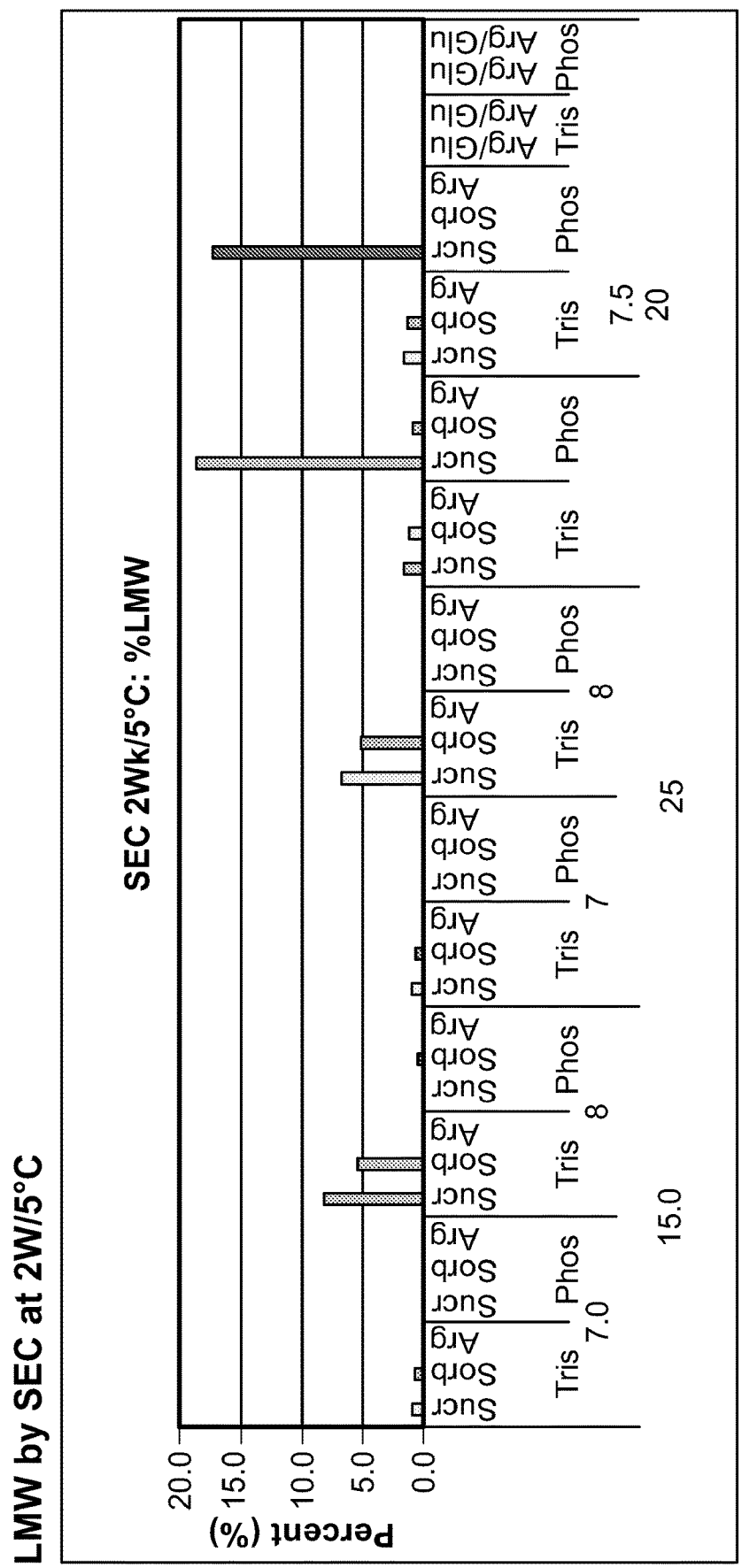
FIG. 14A shows low molecular weight (LMW) by size exclusion chromatography (SEC) at 2 W/5° C. according to some embodiments.
Figure 14B:
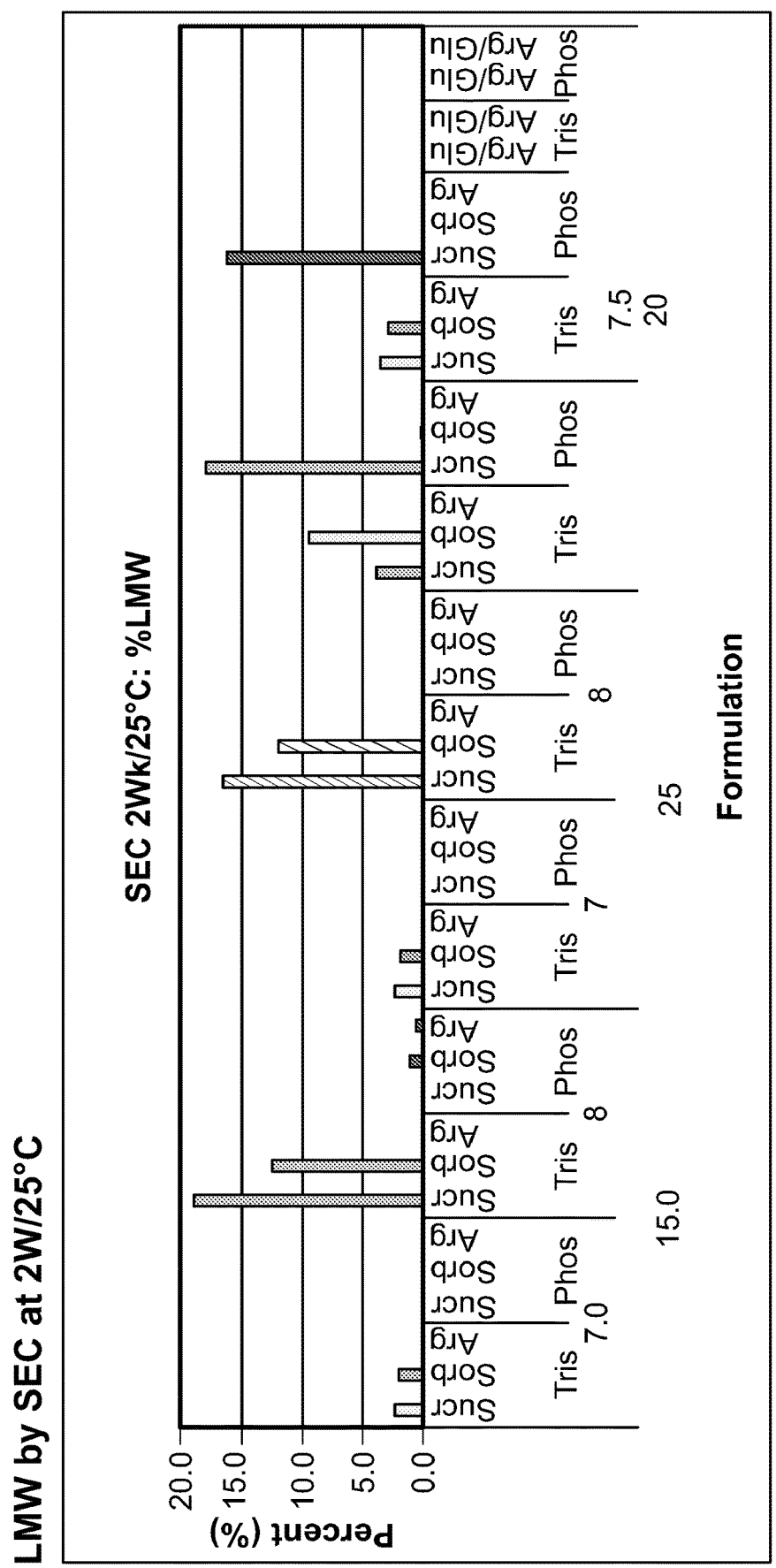
FIG. 14B shows LMW by SEC at 2 W/25° C. according to some embodiments.
Figure 15:
FIG. 15 shows 3D surface plot—Percentage Main Peak (MP) imaged capillary isoelectric focusing (icIEF) 5° C. according to some embodiments.
Figure 15:
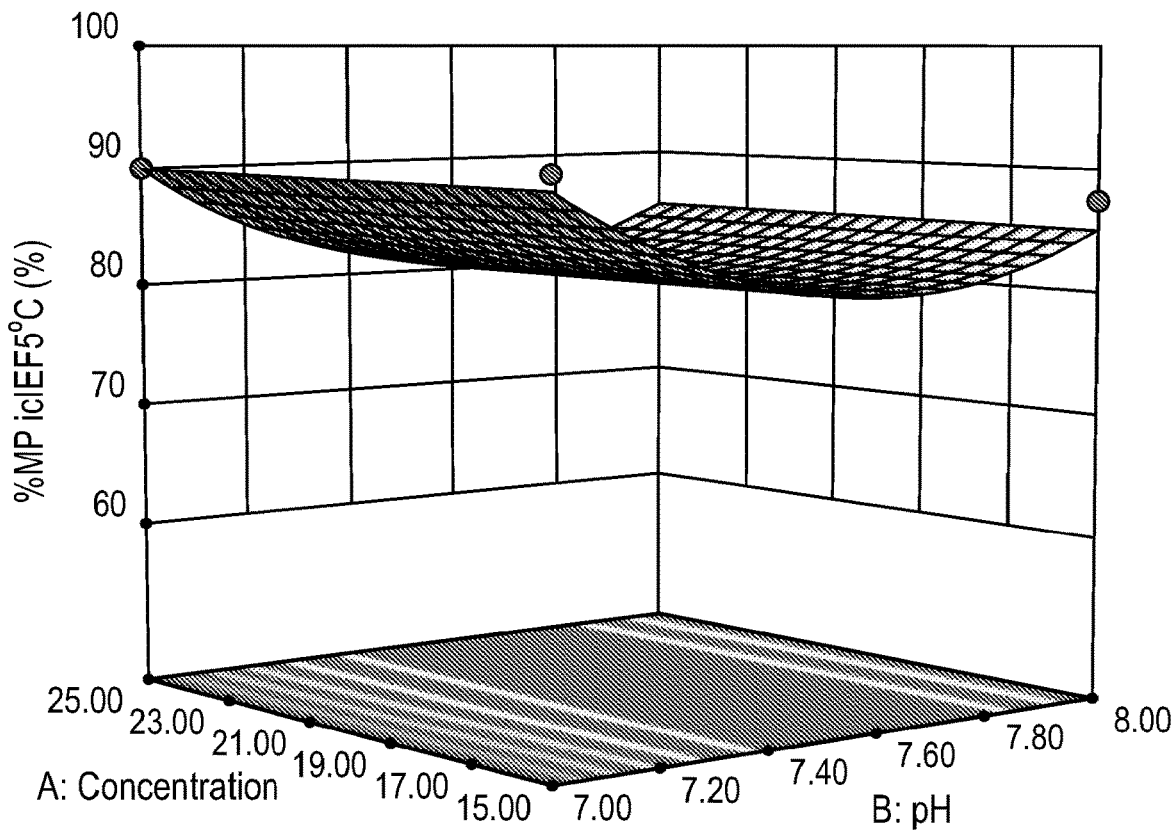
Figure 16:
FIG. 16 shows 3D surface for SEC % MP 2 W/25° C. according to some embodiments.
Figure 16:
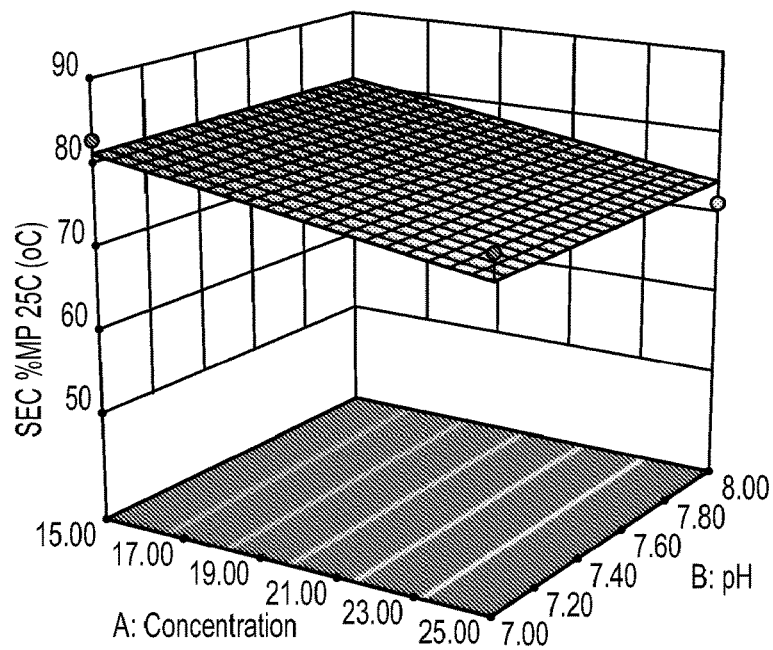
Figure 17:
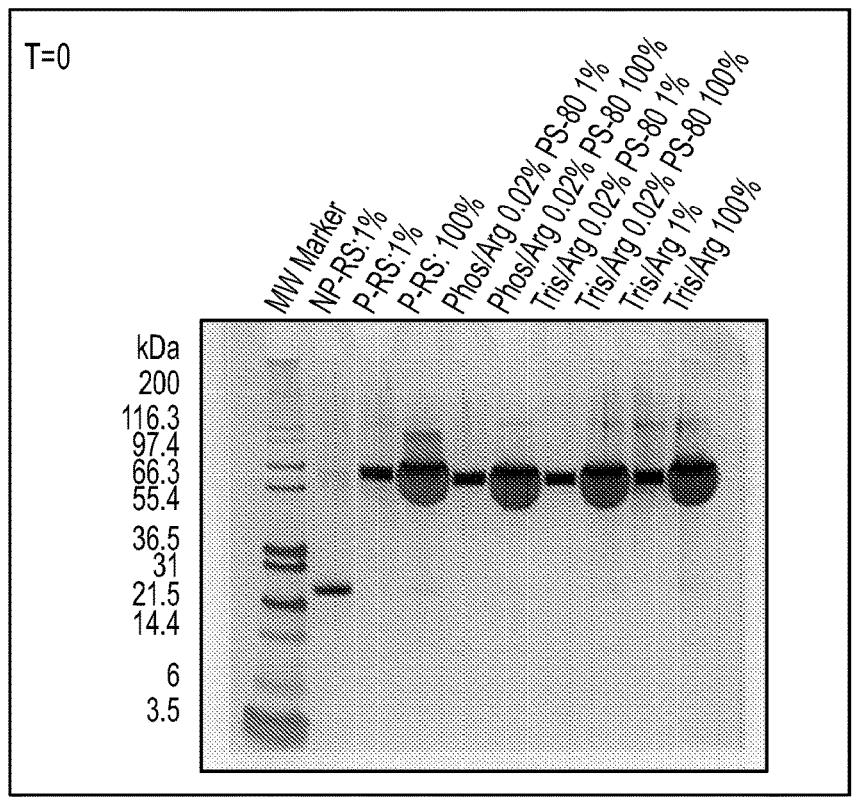
FIG. 17 shows SDS-PAGE Reduced Gel-12M stability (T0) according to some embodiments.
Figure 18:
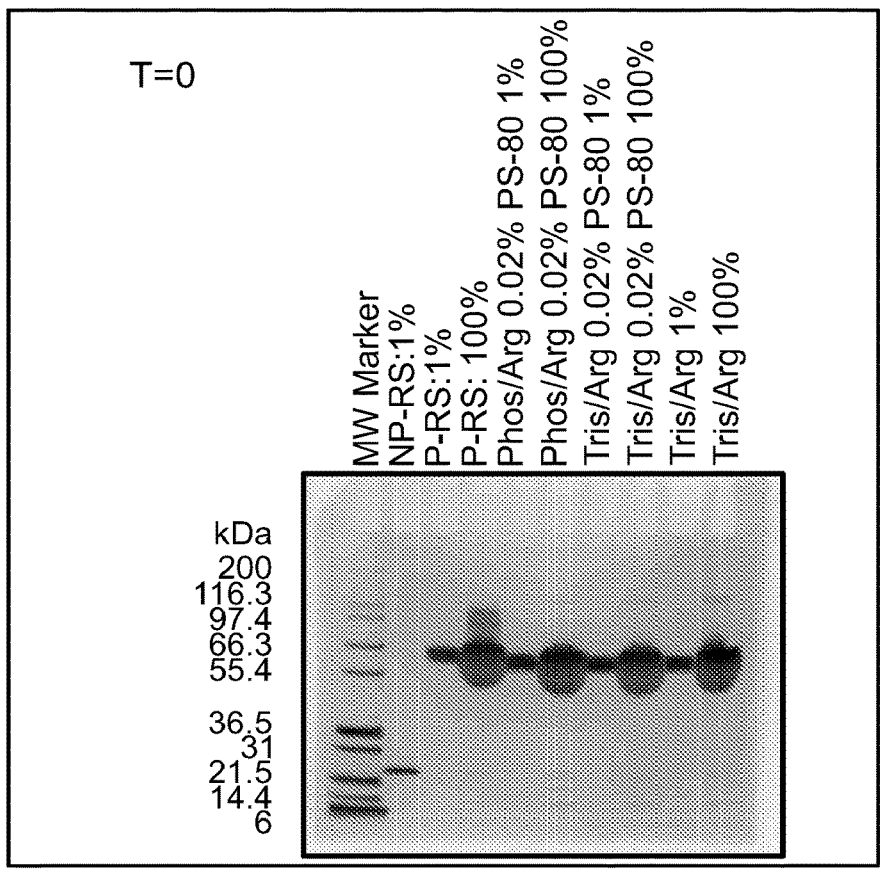
FIG. 18 shows SDS-PAGE Non-Reduced Gel-12M stability (T0) according to some embodiments.
Figure 19:
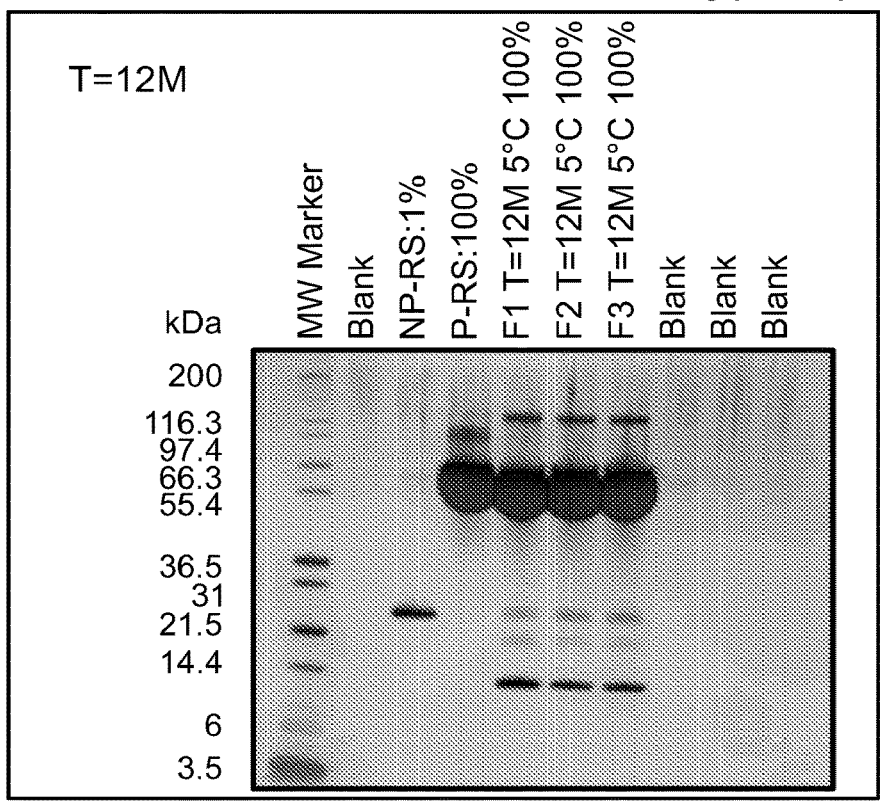
FIG. 19 shows SDS-PAGE Reduced Gel-12M stability (T12M) according to some embodiments.
Figure 20:
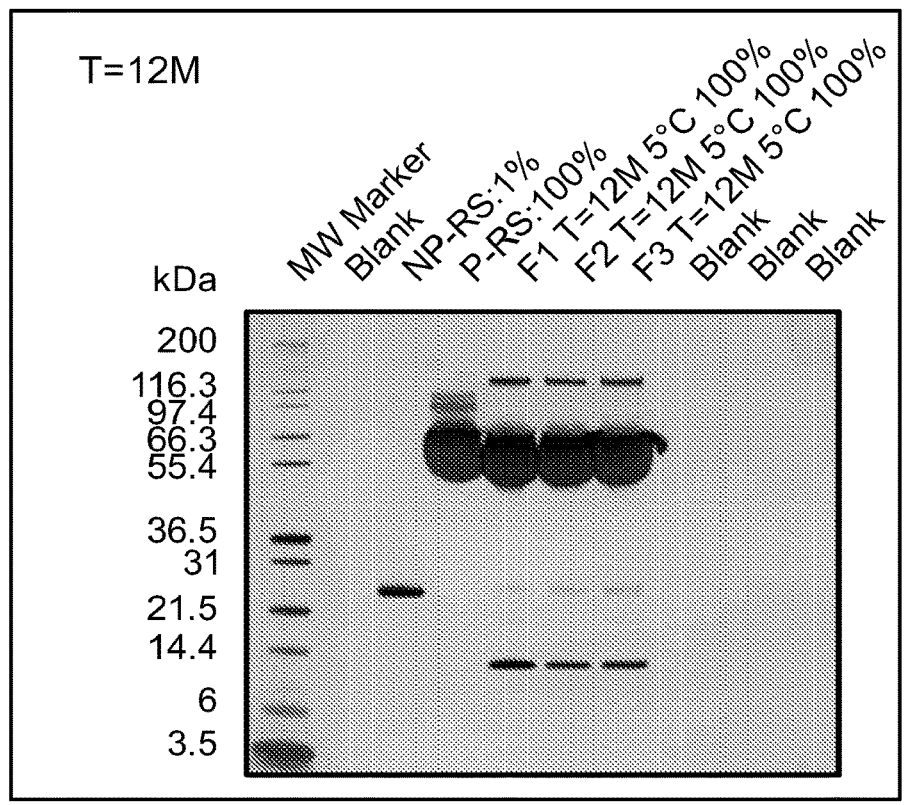
FIG. 20 shows SDS-PAGE Non-Reduced Gel-12M stability (T12M) according to some embodiments.

GlycoPEGylation of mutant FGF-21 peptide may be performed by two enzymatic reactions performed in series or at the same time. In the process where enzymatic steps are in series, there an anion exchange chromatography step (e.g. one anion exchange chromatography step) can be performed between the two sequential enzymatic steps. This step may be followed by 0.2 μm filtration and two anion exchange chromatography operations, both utilizing Q Sepharose Fast Flow chromatography resin and operated in bind and elute mode. A final concentration step may be performed by ultrafiltration using Pellicon XL Biomax (10 kDa MWCO). FIGS. 2 to 4 illustrate a non limiting exemplary method of production. See FIG. 4.

Two principal classes of enzymes are used in the synthesis of carbohydrates, glycosyltransferases (e.g., sialyltransferases, oligosaccharyltransferases, N-acetylglucosaminyltransferases), and glycosidases. The glycosidases are further classified as exoglycosidases (e.g., β-mannosidase, β-glucosidase), and endoglycosidases (e.g., Endo-A, Endo-M). Each of these classes of enzymes has been successfully used synthetically to prepare carbohydrates. For a general review, see, Crout et al., Curr. Opin. Chem. Biol. 2: 98-111 (1998). See also PCT Publication Nos: WO 2003/031464; WO 2005/089102; WO 2006/050247; and WO 2012/016984, the entire content of each of which is incorporated herein by reference.

In some embodiments, the 20 kDa PEG-Sia donor comprises the structure

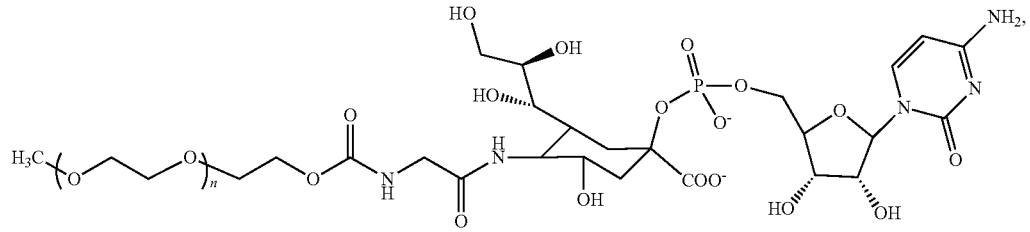

wherein n is an integer selected from 450 to 460, which results in a molecular weight of 20 kDa.

This structure includes a Gly linker. The skilled person understands that any methods for producing the same can be used, for example methods described in PCT Publication No. WO 2003/031464, the entire content of which is incorporated herein by reference.

In some embodiment, the FGF-21 peptide conjugate is filtered using 0.22 micron filter. Further, the mutant FGF-21 peptide conjugate may be sterile filtered.

Also provided are the mutant FGF-21 peptide conjugates obtainable by the method of the disclosure.

In some embodiments, the concentrated protein solution (PEG FGF-21) is thawed from −80 C until liquid. In some embodiments, buffer exchange is performed by diafiltration process with approximately 7 volumes exchanged with formulation buffer, 20 mM Tris, 150 mM Arg-HCl, pH 7.5. In some embodiments, the protein concentration is adjusted to approximately 20 mg/mL, using diafiltration buffer. In some embodiments, polysorbate 80 (PS80) is then added to 0.02%. In some embodiments, the solution is sterile filtered using 0.22 μm filters and filled into sterile vials.

Use

The present disclosure provides a liquid pharmaceutical composition for use as a medicament and for use in the treatment of diabetes and related diseases, particularly diabetes type 2, non-alcoholic steatohepatitis (NASH) and/or metabolic syndrome. The disclosure also provides the use of the liquid pharmaceutical composition for the treatment of diabetes and related diseases, particularly diabetes type 2, NASH and/or metabolic syndrome.

Further provided is a method of treating diabetes and related diseases, particularly diabetes type 2, NASH, non-alcoholic fatty liver disease (NAFLD), and/or metabolic syndrome comprising administering to a subject in need thereof the liquid pharmaceutical composition according to the disclosure. In a particular embodiment, the subject is a human subject.

NAFLD is a common chronic liver disease in Western countries, which can progress to cirrhosis and is associated with an increased mortality risk in general and an increased cardiovascular disease mortality risk in particular. Current pharmacological treatment of NAFLD has limited efficacy and therefore, there is a pressing need to develop more effective and safe agents for this common and life-threatening disease. Obeticholic acid (OCA), a selective agonist of the farnesoid X receptors, appears to have promise as a therapeutic agent for the management of NAFLD. The Farnesoid X Receptor Ligand Obeticholic Acid in NASH Treatment (FLINT) trial in patients with NASH, revealed that OCA administration is associated with improvements in liver histology, as well as weight loss and reduction in blood pressure. Although its adverse effects on lipid profile and insulin sensitivity are noteworthy, OCA might be considered in selected patients with NAFLD/NASH, particularly those with adequately controlled glucose and lipid levels.

With respect to indicators demonstrating clinical efficacy of compounds and compositions described herein, a variety of exemplary indicators are known in the art and described herein including, without limitation, a reduction in HbA1c, glucose and Insulin, body weight, serum lipids (total cholesterol, LDL, Triglycerides), liver enzymes (ALT, AST), liver weight, relative liver weight (% body weight), NAFLD Activity Score (NAS), fibrosis score (e.g., liver fibrosis), pro-inflammatory cytokines (e.g., IL1β, MCP-1), fibrosis biomarkers (αSMA, Collagen 1 alpha), hepatic cholesterol, hepatic triglycerides, and hepatic fatty acids. Increases in at least one of high molecular weight (HMW) adiponectin or HDL are also indicators of clinical efficacy of compounds and compositions described herein. Accordingly, a change (as indicated above) in at least one of the indicators reflects clinical efficacy of a compound or composition described herein. In some embodiments, the therapeutic efficacy of a compound or composition described herein is determined based on a reduction in at least one of serum triglyceride levels or serum insulin levels. HOMA-IR is, for example, is an indicator of the presence and extent of insulin resistance in a subject. It is an accurate indicator of the dynamic between baseline (fasting) blood sugar and insulin levels responsive thereto. It is referred to as an insulin resistance calculator. For humans, a healthy range is 1.0 (0.5-1.4). Less than 1.0 indicates that a subject is insulin-sensitive, which is ideal; above 1.9 indicates that a subject is exhibiting early insulin resistance; above 2.9 indicates that a subject is exhibiting significant insulin resistance. HOMA-IR blood code calculation is determined as follows: insulin uIU/mL (mU/L)×glucose (mg/dL)=HOMA-IR. The calculation requires U.S. standard units. To convert from international SI units: for insulin: pmol/L to uIU/mL, divide (÷) by 6; for glucose: mmol/L to mg/dL, multiply (×) by 8.

Also presented herein are therapeutic regimen, whereby a liquid pharmaceutical composition comprising a therapeutically effective amount of a mutant FGF-21 peptide conjugate is administered twice per day, once per day, every two days, three times per week, once per week, once every two weeks, once every three weeks, or once per month. For example, the liquid pharmaceutical composition comprising from about 10 mg up to 45 mg from about 20 mg to about 44 mg, from about 28 mg to about 44 g, from about 36 mg to about 44 mg, from about 20 mg to about 36 mg, from about 28 mg to about 36 mg, from about 20 mg to about 28 mg of a mutant FGF-21 peptide conjugate (e.g. about 10 mg, 18 mg, 20 mg, 25 mg, 28 mg, 30 mg, 36 mg, 42 mg or 44 mg) can be administered to a subject in need thereof twice per day, once per day, every two days, three times per week, once per week, once every two weeks, once every three weeks, or once per month. In some embodiments, the liquid pharmaceutical composition comprising up to 44 mg/ml of a mutant FGF-21 peptide conjugate is administered to a subject in need thereof once every week or once every two weeks. Long duration efficacy of mutant FGF-21 peptide conjugates described herein is evidenced by the surprisingly long half-life determined for these conjugates in animal model systems. Long duration efficacy of mutant FGF-21 peptide conjugates described herein, in turn, makes it possible to administer the mutant FGF-21 peptide conjugates less frequently. Accordingly, in some embodiments, a mutant FGF-21 peptide conjugate described herein or a composition comprising same is administered to a subject in need thereof at a frequency of equal to or greater than once per week. For example, the mutant FGF-21 peptide conjugate described herein or a composition comprising same may be administered to a subject in need thereof once every 7 days, once every 8 days, once every 9 days, once every 10 days, once every 11 days, once every 12 days, once every 13 days, once every 14 days, once every 15 days, once every 16 days, once every 17 days, once every 18 days, once every 19 days, once every 20 days, once every 21 days, once every 22 days, once every 22 days, once every 23 days, once every 24 days, once every 25 days, once every 26 days, once every 27 days, once every 28 days, once every 29 days, once every 30 days, or once every 31 days.

In another exemplary therapeutic regimen, compounds described herein and compositions comprising same are following a course of "induction" therapy, which calls for more frequent administration such as twice a week or weekly at the onset of the treatment regimen followed by maintenance therapy, which may involve bi-weekly or once a month administration. Such regimen are effective in that the initial induction therapy improves the subject's condition to a manageable level that is acceptable with regard to achieving a clinical state that is acceptable for maintenance of the disease/condition. Thereafter, the maintenance therapy is used to preserve the level of wellness at the maintenance level.

Therapeutic efficacy of a compound and/or composition for treating diabetes and related diseases, particularly diabetes type 2, non-alcoholic steatohepatitis (NASH) and/or metabolic syndrome may be evaluated using a variety of parameters and assays known by persons of skill in the art and described herein. Measuring hemoglobin A1c (HbA1C) is considered a standard assay for measuring glycemic index of a subject over a long duration. It is, therefore, a stable indicator of glycemic index, reflecting glucose levels over the course of approximately the last 3-4 months.

Accordingly, a subject who has diabetes (e.g., diabetes type 2) may be defined by the percent HbA1C determined in a suitable assay.

For a healthy person without diabetes, the normal range for the hemoglobin A1c level is between 4% and 5.6%. Hemoglobin A1c levels between 5.7% and 6.4% indicate that a person has a higher chance of developing diabetes. Levels of 6.5% or higher indicate that a person has diabetes.

In some embodiments, HbA1C is measured with HPLC by using the Glycated hemoglobin test system (BIO-RAD, Hercules, CA, USA). Blood samples (e.g., 1.0 mL/per time) may be collected from the cephalic or saphenous vein into BD Vacutainer® K2-EDTA tubes. Samples may be stored immediately at 4 degrees C. or maintained on wet ice and analyzed on the same day the blood was collected. HbA1c levels in the blood may be measured by persons skilled in the art with HPLC by using the Glycated hemoglobin test system (BIO-RAD, Hercules, CA, USA).

With regard to NASH, this condition is currently diagnosed only by biopsy. There are some surrrogate biomarkers however, that are considered predictive of NASH, such as liver fat (determined by MRI), liver enzymes (ALT and ALT/AST ratio), and fibrosis biomarkers, such as pro-C3.

EXAMPLES

The following Examples illustrate specific embodiments of the disclosure. They are set forth for explanatory purposes only and are not to be taken as limiting the disclosure.

Liquid Formulation

A liquid formulation for GlycoPEGylated FGF-21 mutants (PEG-FGF21, also referred herein as mutant FGF-21 peptide conjugate) was developed. The formulation was supported by stability data up to 12 months at 2-8° C. storage and is suitable for in clinic or at home administration. Additional optimization was performed leading to improved formulation with higher PEG-FGF21 concentrations.

Pre formulation development studies for PEG-FGF21 were performed to establish a formulation composition that would provide optimized physical, chemical and structural stability to the protein. Various buffers, excipients, surfactants, and pH were screened to optimize protein stability at a target concentration of approximately 20 mg/mL.

Based on Baseline Biophysical Screening I (BBSI), a list of buffers with different pH were screened to test sixteen (16) unique formulations to identify suitable pH/buffer combination by testing PEGylated and non-PEG-FGF21s at 2 mg/mL. The samples were tested by static light scattering (SLS) and dynamic light scattering (DLS). DSF results for the non-PEG-FGF21s and DLS and SLS results for both PEGylated and non-PEGylated material suggested pH range of 6.5 to 8.5 to be suitable for protein solubility. In the second study, Baseline Biophysical Screening II (BBSII), effect of 150 mM NaCl, 150 mM Arg-HCl, 250 mM sucrose and 250 mM sorbitol as excipients in buffers with pH ranging from 6.5 to 8.0 were evaluated. SLS, DLS and DSF were performed on the PEGylated and non-PEG-FGF21 at 2 mg/mL. Tris at pH 8.0, and phosphate at pH 7.5 with arginine, sucrose and sorbitol provided most suitable for stability of PEG-FGF21 and non-PEG-FGF21 (FIGS. 5-11).

In the third study—solubility study optimal combinations of pH, buffer, and excipients established in BBSII were used to determine formulations that provide stability to PEG-FGF21 at high concentration (~50 mg/mL). DLS and SEC testing was performed on the samples and it was determined that Phosphate/Arg-HCl and Phosphate/Sucrose formulations as low aggregate generating formulations per SEC analysis and also exhibited DLS plots with lower intensities for large aggregates. Tris/Sucrose was selected because it had the lowest percentage of total aggregates by SEC, and Tris/Sorbitol and Tris/Arg-HCl were selected due to having low aggregates as indicated by SEC and DLS. A fourth study determined the effect of surfactants on the stability of the product and found to be not detrimental to the product.

Results obtained from the first four studies were used to select the design space from a Design of Experiments study (DOE). A randomized response surface design with two numerical factors (pH and protein concentration), two categorical factors (buffer and excipient types) was used to develop a design with six center points. A total of 36 formulations (Tables 1 and 2) were selected to screen PEG-FGF21 and additional four off-DOE formulations were added to screen a combination of Arginine and Gluconate and cetrimonium bromide.

Figure 21:
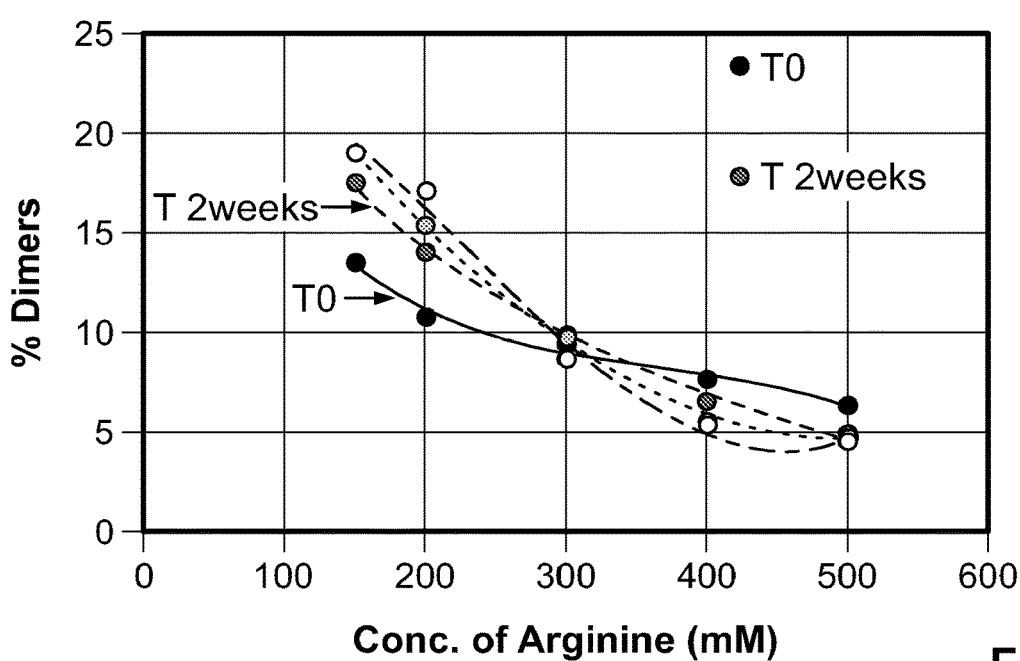
FIG. 21 shows arginine HCl influence on dimerization according to some embodiments.

The resulting samples were stored at 5° C. for 8 weeks, and 25° C. for two weeks and tested by UV, SEC, RP-HPLC, and DLS. Viscosity. Mirco-flow imaging (MFI), DSF and pH testing was performed only at initial time point (T=0). DLS testing was only performed at 2 Week (2 W). Data showed that the dimers were effectively controlled by increase in arginine concentrations (FIG. 21). Key results from DOE is presented in FIGS. 11-16. The results provided a formulation at pH 7.5, comprising 150 mM Arginine wherein 20 mg/mL PEG-FGF21 can maintain all the quality attributes related to dimers, aggregation and degradation.

Formulations with or without PS80 were monitored under long term stability for a period of 12 months. See FIGS. 17-20. The long-term stability demonstrated that PEG-FGF21 maintained all quality attributes by controlling acid variants, dimers, particulates etc. while maintaining activity thereby demonstrating suitability for storage as a liquid formulation.

TABLE 1

Selected Formulations (DS Design of Experiment Study)
Solution from Round 1 and Round 2 Optimization

| Optimization | Number | Conc. | pH | Excipient | Buffer | SEC % dimer 5° C. | SEC % dimer 25° C. | Desirability |
|---|---|---|---|---|---|---|---|---|
| 1 | 1 | 24.1 | 7.0 | 150 mM Arg-HCl | 20 mM Tris | 22.121 | 23.335 | 0.836 |
| | 2 | 24.0 | 7.0 | 150 mM Arg-HCl | 20 mM Tris | 22.111 | 23.298 | 0.836 |
| | 3 | 23.9 | 7.0 | 150 mM Arg-HCl | 20 mM Tris | 22.099 | 23.254 | 0.836 |
| | 4 | 24.1 | 7.0 | 150 mM Arg-HCl | 20 mM Tris | 22.128 | 23.361 | 0.836 |
| | 5 | 23.6 | 7.0 | 150 mM Arg-HCl | 20 mM Tris | 22.035 | 23.03 | 0.836 |
| | 6 | 23.6 | 7.0 | 150 mM Arg-HCl | 20 mM Tris | 22.028 | 23.005 | 0.836 |
| | 7 | 24.2 | 7.0 | 150 mM Arg-HCl | 20 mM Tris | 22.135 | 23.424 | 0.836 |
| | 8 | 23.0 | 7.0 | 150 mM Arg-HCl | 20 mM Tris | 21.907 | 22.628 | 0.835 |
| | 9 | 22.7 | 7.0 | 150 mM Arg-HCl | 20 mM Tris | 21.83 | 22.409 | 0.835 |
| | 10 | 25.0 | 7.0 | 150 mM Arg-HCl | 20 mM Phosphate | 24.567 | 31.129 | 0.723 |
| 2 | 1 | 15 | 7.0 | 150 mM Arg-HCl | 20 mM Tris | 18.6 | 17.2 | 0.786 |
| | 2 | 15 | 7.0 | 150 mM Arg-HCl | 20 mM Tris | 18.7 | 17.3 | 0.786 |
| | 3 | 16 | 7.0 | 150 mM Arg-HCl | 20 mM Tris | 19.0 | 17.7 | 0.784 |
| | 4 | 16 | 7.0 | 150 mM Arg-HCl | 20 mM Tris | 19.0 | 17.7 | 0.783 |
| | 5 | 16 | 7.0 | 150 mM Arg-HCl | 20 mM Tris | 19.2 | 18.0 | 0.782 |
| | 6 | 15 | 7.0 | 150 mM Arg-HCl | 20 mM Tris | 18.6 | 17.2 | 0.781 |
| | 7 | 17 | 7.0 | 150 mM Arg-HCl | 20 mM Tris | 19.5 | 18.3 | 0.78 |
| | 8 | 17 | 7.0 | 150 mM Arg-HCl | 20 mM Tris | 19.6 | 18.5 | 0.779 |
| | 9 | 17 | 7.0 | 150 mM Arg-HCl | 20 mM Tris | 19.7 | 18.6 | 0.778 |
| | 10 | 21 | 7.0 | 150 mM Arg-HCl | 20 mM Tris | 21.5 | 21.5 | 0.759 |

TABLE 2

| Formulation Code | Protein Concentration (mg/mL) | Buffer Type | Buffer Concentration (mM) | Excipient (mM) | Surfactant (%) | pH |
|---|---|---|---|---|---|---|
| 1 | 20 | Phosphate | 20 | Arg-HCl, 150 mM | 0.02% PS-80 | 7.5 |
| 2 | 20 | Tris | 20 | Arg-HCl, 150 mM | 0.02% PS-80 | 7.5 |
| 3 | 20 | Tris | 20 | Arg-HCl, 150 mM | N/A | 7.5 |

TABLE 3

Test Methods for the Stability Study

| Test | Method |
|---|---|
| Quality | Description |
|  | pH |
| Quantity | Protein Content |
| Charge Heterogeneity | icIEF |
| Purity | SEC |
|  | SDS (Reduced) |
|  | SDS (Non-Reduced) |
|  | RP-HPLC |
| Particle Count | MFI |
| Other | Osmolality |

TABLE 4

Appearance Results -- 12 M stability

| Formulation Code | Time Point | Condition | Appearance Results |
|---|---|---|---|
| 1 | Initial | N/A | Colorless, clear liquid. Free of visible particulates |
|  | 2 Weeks | 5 ± 3° C. | Colorless, clear liquid. Free of visible particulates |
|  |  | 25 ± 2° C./60 ± 5% RH | Colorless, clear liquid. Free of visible particulates |
|  |  | 40 ± 2° C./75 ± 5% RH | Colorless, clear liquid. Free of visible particulates |
|  | 1 Month | 5 ± 3° C. | Colorless, clear liquid. Free of visible particulates |
|  |  | 25 ± 2° C./60 ± 5% RH | Colorless, clear liquid. Free of visible particulates |
|  |  | 40 ± 2° C./75 ± 5% RH | Colorless, clear liquid. Free of visible particulates |
|  | 2 Month | 5 ± 3° C. | Colorless, clear liquid. Free of visible particulates |
|  |  | 25 ± 2° C./60 ± 5% RH | Colorless, clear liquid. Free of visible particulates |
|  |  | 40 ± 2° C./75 ± 5% RH | Colorless, clear liquid. Free of visible particulates |
|  | 3 Month | 5 ± 3° C. | Colorless, clear liquid. Free of visible particulates |
|  |  | 25 ± 2° C./60 ± 5% RH | Colorless, clear liquid. Free of visible particulates |
|  | 6 Month | 5 ± 3° C. | Colorless, clear liquid. Free of visible particulates |
|  |  | 25 ± 2° C./60 ± 5% RH | Colorless, clear liquid. Free of visible particulates |
|  | 9 Month | 5 ± 3° C. | Colorless, clear liquid. Free of visible particulates |
|  | 12 Month | 5 ± 3° C. | Colorless, clear liquid. Free of visible particulates |
| 2 | Initial | N/A | Colorless, clear liquid. Free of visible particulates |
|  | 2 Weeks | 5 ± 3° C. | Colorless, clear liquid. Free of visible particulates |
|  |  | 25 ± 2° C./60 ± 5% RH | Colorless, clear liquid. Free of visible particulates |
|  |  | 40 ± 2° C./75 ± 5% RH | Colorless, clear liquid. Free of visible particulates |
|  | 1 Month | 5 ± 3° C. | Colorless, clear liquid. Free of visible particulates |
|  |  | 25 ± 2° C./60 ± 5% RH | Colorless, clear liquid. Free of visible particulates |
|  |  | 40 ± 2° C./75 ± 5% RH | Colorless, clear liquid. Free of visible particulates |
|  | 2 Month | 5 ± 3° C. | Colorless, clear liquid. Free of visible particulates |
|  |  | 25 ± 2° C./60 ± 5% RH | Colorless, clear liquid. Free of visible particulates |
|  |  | 40 ± 2° C./75 ± 5% RH | Colorless, clear liquid. Free of visible particulates |
|  | 3 Month | 5 ± 3° C. | Colorless, clear liquid. Free of visible particulates |
|  |  | 25 ± 2° C./60 ± 5% RH | Colorless, clear liquid. Free of visible particulates |
|  | 6 Month | 5 ± 3° C. | Colorless, clear liquid. Free of visible particulates |
|  |  | 25 ± 2° C./60 ± 5% RH | Colorless, clear liquid. Free of visible particulates |
|  | 9 Month | 5 ± 3° C. | Colorless, clear liquid. Free of visible particulates |
|  | 12 Month | 5 ± 3° C. | Colorless, clear liquid. Free of visible particulates |
| 3 | Initial | N/A | Colorless, clear liquid. Free of visible particulates |
|  | 2 Weeks | 5 ± 3° C. | Colorless, clear liquid. Free of visible particulates |
|  |  | 25 ± 2° C./60 ± 5% RH | Colorless, clear liquid. Free of visible particulates |
|  |  | 40 ± 2° C./75 ± 5% RH | Colorless, clear liquid. Free of visible particulates |
|  | 1 Month | 5 ± 3° C. | Colorless, clear liquid. Free of visible particulates |
|  |  | 25 ± 2° C./60 ± 5% RH | Colorless, clear liquid. Free of visible particulates |
|  |  | 40 ± 2° C./75 ± 5% RH | Colorless, clear liquid. Free of visible particulates |
|  | 2 Month | 5 ± 3° C. | Colorless, clear liquid. Free of visible particulates |
|  |  | 25 ± 2° C./60 ± 5% RH | Colorless, clear liquid. Free of visible particulates |
|  |  | 40 ± 2° C./75 ± 5% RH | Colorless, clear liquid. Free of visible particulates |
|  | 3 Month | 5 ± 3° C. | Colorless, clear liquid. Free of visible particulates |
|  |  | 25 ± 2° C./60 ± 5% RH | Colorless, clear liquid. Free of visible particulates |
|  | 6 Month | 5 ± 3° C. | Colorless, clear liquid. Free of visible particulates |
|  |  | 25 ± 2° C./60 ± 5% RH | Colorless, clear liquid. Free of visible particulates |
|  | 9 Month | 5 ± 3° C. | Colorless, clear liquid. Free of visible particulates |
|  | 12 Month | 5 ± 3° C. | Colorless, clear liquid. Free of visible particulates |

TABLE 5 pH Results - 12 M stability

| Formulation Code | Time Point | Condition | pH Results |
|---|---|---|---|
| 1 | Initial | N/A | 7.4 |
|  | 2 weeks | 5 ± 3° C. | 7.4 |
|  |  | 25 ± 2° C./60 ± 5% RH | 7.4 |
|  |  | 40 ± 2° C./75 ± 5% RH | 7.4 |
|  | 1 Month | 5 ± 3° C. | 7.4 |
|  |  | 25 ± 2° C./60 ± 5% RH | 7.4 |
|  |  | 40 ± 2° C./75 ± 5% RH | 7.5 |
|  | 2 Month | 5 ± 3° C. | 7.4 |
|  |  | 25 ± 2° C./60 ± 5% RH | 7.4 |
|  |  | 40 ± 2° C./75 ± 5% RH | 7.4 |
|  | 3 Month | 5 ± 3° C. | 7.4 |
|  |  | 25 ± 2° C./60 ± 5% RH | 7.4 |
|  | 6 Month | 5 ± 3° C. | 7.4 |
|  |  | 25 ± 2° C./60 ± 5% RH | 7.4 |
|  | 9 Month | 5 ± 3° C. | 7.5 |
|  | 12 Month | 5 ± 3° C. | 7.4 |
| 2 | Initial | N/A | 7.4 |
|  | 2 weeks | 5 ± 3° C. | 7.3 |
|  |  | 25 ± 2° C./60 ± 5% RH | 7.4 |
|  |  | 40 ± 2° C./75 ± 5% RH | 7.4 |
|  | 1 Month | 5 ± 3° C. | 7.4 |
|  |  | 25 ± 2° C./60 ± 5% RH | 7.4 |
|  |  | 40 ± 2° C./75 ± 5% RH | 7.4 |
|  | 2 Month | 5 ± 3° C. | 7.3 |
|  |  | 25 ± 2° C./60 ± 5% RH | 7.4 |
|  |  | 40 ± 2° C./75 ± 5% RH | 7.4 |
|  | 3 Month | 5 ± 3° C. | 7.4 |
|  |  | 25 ± 2° C./60 ± 5% RH | 7.4 |
|  | 6 Month | 5 ± 3° C. | 7.4 |
|  |  | 25 ± 2° C./60 ± 5% RH | 7.5 |
|  | 9 Month | 5 ± 3° C. | 7.4 |
|  | 12 Month | 5 ± 3° C. | 7.3 |
| 3 | Initial | N/A | 7.5 |
|  | 2 weeks | 5 ± 3° C. | 7.3 |
|  |  | 25 ± 2° C./60 ± 5% RH | 7.4 |
|  |  | 40 ± 2° C./75 ± 5% RH | 7.4 |
|  | 1 Month | 5 ± 3° C. | 7.4 |
|  |  | 25 ± 2° C./60 ± 5% RH | 7.4 |
|  |  | 40 ± 2° C./75 ± 5% RH | 7.4 |
|  | 2 Month | 5 ± 3° C. | 7.3 |
|  |  | 25 ± 2° C./60 ± 5% RH | 7.4 |
|  |  | 40 ± 2° C./75 ± 5% RH | 7.4 |
|  | 3 Month | 5 ± 3° C. | 7.4 |
|  |  | 25 ± 2° C./60 ± 5% RH | 7.3 |
|  | 6 Month | 5 ± 3° C. | 7.4 |
|  |  | 25 ± 2° C./60 ± 5% RH | 7.4 |
|  | 9 Month | 5 ± 3° C. | 7.4 |
|  | 12 Month | 5 ± 3° C. | 7.4 |

TABLE 6

Protein Concentration Results - 12 M stability

| Formulation Code | Time Point | Condition | Concentration, mg/mL |
|---|---|---|---|
| 1 | Initial | N/A | 19.7 |
|  | 2 Weeks | 5 ± 3° C. | 19.7 |
|  |  | 25 ± 2° C./60 ± 5% RH | 19.8 |
|  |  | 40 ± 2° C./75 ± 5% RH | 19.4 |
|  | 1 Month | 5 ± 3° C. | 19.6 |
|  |  | 25 ± 2° C./60 ± 5% RH | 19.8 |
|  |  | 40 ± 2° C./75 ± 5% RH | 19.2 |
|  | 2 Month | 5 ± 3° C. | 19.7 |
|  |  | 25 ± 2° C./60 ± 5% RH | 19.7 |
|  |  | 40 ± 2° C./75 ± 5% RH | 19.4 |
|  | 3 Month | 5 ± 3° C. | 19.8 |
|  |  | 25 ± 2° C./60 ± 5% RH | 19.6 |
|  | 6 Month | 5 ± 3° C. | 19.8 |
|  |  | 25 ± 2° C./60 ± 5% RH | 19.6 |
|  | 9 Month | 5 ± 3° C. | 19.9 |
|  | 12 Month | 5 ± 3° C. | 19.9 |
| 2 | Initial | N/A | 19.2 |
|  | 2 Weeks | 5 ± 3° C. | 19.2 |
|  |  | 25 ± 2° C./60 ± 5% RH | 19.3 |
|  |  | 40 ± 2° C./75 ± 5% RH | 18.9 |
|  | 1 Month | 5 ± 3°C | 19.3 |
|  |  | 25 ± 2° C./60 ± 5% RH | 19.2 |
|  |  | 40 ± 2° C./75 ± 5% RH | 19.3 |
|  | 2 Month | 5 ± 3° C. | 19.2 |
|  |  | 25 ± 2° C./60 ± 5% RH | 19.1 |
|  |  | 40 ± 2° C./75 ± 5% RH | 18.4 |
|  | 3 Month | 5 ± 3° C. | 19.2 |
|  |  | 25 ± 2° C./60 ± 5% RH | 19.1 |
|  | 6 Month | 5 ± 3° C. | 19.2 |
|  |  | 25 ± 2° C./60 ± 5% RH | 19.2 |
|  | 9 Month | 5 ± 3° C. | 19.3 |
|  | 12 Month | 5 ± 3° C. | 19.4 |
| 3 | Initial | N/A | 19.4 |
|  | 2 Weeks | 5 ± 3° C. | 19.5 |
|  |  | 25 ± 2° C./60 ± 5% RH | 19.6 |
|  |  | 40 ± 2° C./75 ± 5% RH | 19.1 |
|  | 1 Month | 5 ± 3° C. | 19.5 |
|  |  | 25 ± 2° C./60 ± 5% RH | 19.5 |
|  |  | 40 ± 2° C./75 ± 5% RH | 20.9 |
|  | 2 Month | 5 ± 3° C. | 19.4 |
|  |  | 25 ± 2° C./60 ± 5% RH | 19.5 |
|  |  | 40 ± 2° C./75 ± 5% RH | 18.7 |
|  | 3 Month | 5 ± 3° C. | 19.4 |
|  |  | 25 ± 2° C./60 ± 5% RH | 19.4 |
|  | 6 Month | 5 ± 3° C. | 19.5 |
|  |  | 25 ± 2° C./60 ± 5% RH | 19.5 |
|  | 9 Month | 5 ± 3° C. | 19.5 |
|  | 12 Month | 5 ± 3° C. | 19.6 |

TABLE 7

Osmolality Results T0 data

| Formulation Code | mOsm/kg |
|---|---|
| 1 | 317 |
| 2 | 302 |
| 3 | 303 |

TABLE 8

SEC-HPLC Results - 12M stability

| Form. # | Time Point | Condition | % RRT-0.77 | % RRT-0.83 | % PEG-BTPH-034 dimer | % PEG-BTPH-034 | % Total Aggregates | % LMW |
|---|---|---|---|---|---|---|---|---|
| 1 | Initial | N/A | N.D | 0.3 | 14.1 | 85.6 | 14.4 | N.D. |
|  | 2 weeks | 5 ± 3° C. | N.D. | 0.4 | 17.5 | 82.1 | 17.9 | N.D. |
|  |  | 25 ± 2° C./60 ± 5% RH | N.D. | 0.6 | 26.6 | 72.4 | 27.2 | 0.4 |
|  |  | 40 ± 2° C./75 ± 5% RH | N.D. | 0.8 | 14.4 | 82.4 | 15.2 | 2.4 |
|  | 1 Month | 5 ± 3° C. | N.D. | 0.8 | 21.5 | 77.6 | 22.4 | 0.0 |
|  |  | 25 ± 2° C./60 ± 5% RH | N.D. | 0.9 | 25.7 | 72.7 | 26.6 | 0.7 |
|  |  | 40 ± 2° C./75 ± 5% RH | N.D. | 0.8 | 24.7 | 70.1 | 25.6 | 4.3 |
|  | 2 Month | 5 ± 3° C. | N.D. | 0.7 | 23.9 | 75.3 | 24.6 | 0.1 |
|  |  | 25 ± 2° C./60 ± 5% RH | N.D. | 0.6 | 24.4 | 73.7 | 25.0 | 1.3 |
|  |  | 40 ± 2° C./75 ± 5% RH | N.D. | 1.4 | 38.9 | 52.1 | 40.3 | 7.6 |
|  | 3 Month | 5 ± 3° C. | N.D. | 0.4 | 24.6 | 74.9 | 25.0 | 0.1 |
|  |  | 25 ± 2° C./60 ± 5% RH | N.D. | 0.4 | 24.1 | 73.4 | 24.5 | 2.1 |
|  | 6 Month | 5 ± 3° C. | N.D. | 0.9 | 25.3 | 73.5 | 26.2 | 0.3 |
|  |  | 25 ± 2° C./60 ± 5% RH | N.D. | 0.7 | 24.8 | 70.7 | 25.5 | 3.8 |
|  | 9 Month | 5 ± 3° C. | 0.3 | 0.4 | 24.8 | 74.1 | 25.4 | 0.4 |
|  | 12 Month | 5 ± 3° C. | 0.2 | 0.6 | 24.2 | 74.5 | 25.1 | 0.5 |
| 2 | Initial | N/A | N.D. | 0.3 | 14.0 | 85.7 | 14.3 | N.D. |
|  | 2 weeks | 5 ± 3° C. | N.D. | 0.3 | 16.3 | 83.4 | 16.6 | N.D. |
|  |  | 25 ± 2° C./60 ± 5% RH | N.D. | 0.5 | 22.9 | 76.5 | 23.4 | 0.1 |
|  |  | 40 ± 2° C./75 ± 5% RH | 0.02 | 0.8 | 14.1 | 83.2 | 14.9 | 1.9 |
|  | 1 Month | 5 ± 3° C. | N.D. | 0.7 | 19.4 | 80.0 | 20.0 | ND |
|  |  | 25 ± 2° C./60 ± 5% RH | N.D. | 0.8 | 22.5 | 76.4 | 23.2 | 0.4 |
|  |  | 40 ± 2° C./75 ± 5% RH | N.D. | 0.8 | 25.8 | 70.4 | 26.6 | 2.9 |
|  | 2 Month | 5 ± 3° C. | N.D. | 0.5 | 21.0 | 78.4 | 21.5 | 0.1 |
|  |  | 25 ± 2° C./60 ± 5% RH | N.D. | 0.6 | 21.7 | 76.8 | 22.3 | 0.9 |
|  |  | 40 ± 2° C./75 ± 5% RH | N.D. | 1.3 | 40.7 | 51.9 | 41.9 | 6.1 |
|  | 3 Month | 5 ± 3° C. | N.D. | 0.3 | 21.3 | 78.2 | 21.7 | 0.1 |
|  |  | 25 ± 2° C./60 ± 5% RH | N.D. | 0.4 | 21.4 | 76.9 | 21.8 | 1.3 |
|  | 6 Month | 5 ± 3° C. | N.D | 0.8 | 22.7 | 76.3 | 23.5 | 0.2 |
|  |  | 25 ± 2° C./60 ± 5% RH | N.D | 0.6 | 23.9 | 72.8 | 24.5 | 2.7 |
|  | 9 Month | 5 ± 3° C. | 0.2 | 0.4 | 21.1 | 78.1 | 21.6 | 0.3 |
|  | 12 Month | 5 ± 3° C. | 0.1 | 0.5 | 20.6 | 78.4 | 21.3 | 0.3 |
| 3 | Initial | N/A | N.D. | 0.3 | 14.1 | 85.6 | 14.4 | N.D. |
|  | 2 weeks | 5 ± 3° C. | N.D. | 0.3 | 16.4 | 83.3 | 16.7 | N.D. |
|  |  | 25 ± 2° C./60 ± 5% RH | N.D. | 0.5 | 23.1 | 76.2 | 23.6 | 0.1 |
|  |  | 40 ± 2° C./75 ± 5% RH | N.D. | 0.8 | 14.8 | 82.7 | 15.7 | 1.6 |
|  | 1 Month | 5 ± 3° C. | N.D. | 0.7 | 19.5 | 79.8 | 20.2 | N.D. |
|  |  | 25 ± 2° C./60 ± 5% RH | N.D. | 0.8 | 22.6 | 76.2 | 23.4 | 0.4 |
|  |  | 40 ± 2° C./75 ± 5% RH | N.D. | 0.8 | 25.8 | 70.4 | 26.6 | 2.9 |
|  | 2 Month | 5 ± 3° C. | N.D | 0.6 | 21.3 | 78.0 | 21.9 | 0.1 |
|  |  | 25 ± 2° C./60 ± 5% RH | N.D. | 0.6 | 21.9 | 76.6 | 22.5 | 0.8 |
|  |  | 40 ± 2° C./75 ± 5% RH | N.D. | 1.3 | 40.7 | 52.0 | 42.0 | 6.0 |
|  | 3 Month | 5 ± 3° C. | N.D. | 0.3 | 21.6 | 78.0 | 21.9 | 0.1 |
|  |  | 25 ± 2° C./60 ± 5% RH | N.D. | 0.4 | 21.6 | 76.7 | 22.0 | 1.3 |
|  | 6 Month | 5 ± 3° C. | N.D. | 0.8 | 22.0 | 77.0 | 22.8 | 0.2 |
|  |  | 25 ± 2° C./60 ± 5% RH | N.D. | 0.6 | 23.7 | 73.0 | 24.3 | 2.7 |
|  | 9 Month | 5 ± 3° C. | 0.2 | 0.4 | 21.3 | 77.9 | 21.8 | 0.3 |
|  | 12 Month | 5 ± 3° C. | 0.2 | 0.5 | 20.9 | 78.1 | 21.6 | 0.3 |

TABLE 9 icIEF Results - 12M stability

| Formulation # | Timepoint | Condition | Average % AV | Average % Main Peak | Average % BV | Average Main Peak pI |
|---|---|---|---|---|---|---|
| 1 | Initial | N/A | 12.5 | 87.5 | N/A | 5.4 |
|  | 2 Weeks | 5 ± 3° C. | 12.2 | 87.8 | N/A | 5.4 |
|  |  | 25 ± 2° C./60 ± 5% RH | 15.7 | 84.3 | N/A | 5.4 |
|  |  | 40 ± 2° C./75 ± 5% RH | 35.8 | 64.2 | N/A | 5.4 |
|  | 1 Month | 5 ± 3° C. | 13.6 | 86.4 | N/A | 5.6 |
|  |  | 25 ± 2° C./60 ± 5% RH | 20.1 | 79.9 | N/A | 5.6 |
|  |  | 40 ± 2° C./75 ± 5% RH | 50.9 | 49.1 | N/A | 5.6 |
|  | 2 Month | 5 ± 3° C. | 13.4 | 86.6 | N/A | 5.4 |
|  |  | 25 ± 2° C./60 ± 5% RH | 32.6 | 67.4 | N/A | 5.4 |
|  |  | 40 ± 2° C./75 ± 5% RH | 70.1 | 23.5 | 6.4 | 5.5 |
|  | 3 Month | 5 ± 3° C. | 13.4 | 86.6 | N/A | 5.4 |
|  |  | 25 ± 2° C./60 ± 5% RH | 41.8 | 58.2 | N/A | 5.4 |
|  | 6 Month | 5 ± 3° C. | 16.1 | 83.9 | N/A | 5.4 |
|  |  | 25 ± 2° C./60 ± 5% RH | 63.5 | 36.5 | N/A | 5.5 |

TABLE 9-continued icIEF Results - 12M stability

| Formulation # | Timepoint | Condition | Average % AV | Average % Main Peak | Average % BV | Average Main Peak pI |
|---|---|---|---|---|---|---|
| | 9 Month | 5 ± 3° C. | 21.6 | 78.4 | N/A | 5.5 |
| | 12 Month | 5 ± 3° C. | 21.6 | 78.4 | N/A | 5.5 |
| 2 | Initial | N/A | 12.1 | 87.9 | N/A | 5.4 |
| | 2 Weeks | 5 ± 3° C. | 12.2 | 87.8 | N/A | 5.3 |
| | | 25 ± 2° C./60 ± 5% RH | 13.6 | 86.4 | N/A | 5.4 |
| | | 40 ± 2° C./75 ± 5% RH | 22.8 | 77.2 | N/A | 5.4 |
| | 1 Month | 5 ± 3° C. | 13.3 | 86.7 | N/A | 5.6 |
| | | 25 ± 2° C./60 ± 5% RH | 15.8 | 84.2 | N/A | 5.5 |
| | | 40 ± 2° C./75 ± 5% RH | 34.8 | 65.2 | N/A | 5.5 |
| | 2 Month | 5 ± 3° C. | 12.8 | 87.2 | N/A | 5.4 |
| | | 25 ± 2° C./60 ± 5% RH | 23.4 | 76.6 | N/A | 5.4 |
| | | 40 ± 2° C./75 ± 5% RH | 53.9 | 39.5 | 6.7 | 5.5 |
| | 3 Month | 5 ± 3° C. | 12.8 | 87.2 | N/A | 5.4 |
| | | 25 ± 2° C./60 ± 5% RH | 29.2 | 70.8 | N/A | 5.4 |
| | 6 Month | 5 ± 3° C. | 13.5 | 86.5 | N/A | 5.4 |
| | | 25 ± 2° C./60 ± 5% RH | 43.9 | 56.1 | N/A | 5.4 |
| | 9 Month | 5 ± 3° C. | 14.6 | 85.4 | N/A | 5.4 |
| | 12 Month | 5 ± 3° C. | 15.9 | 84.1 | N/A | 5.5 |
| 3 | Initial | N/A | 12.2 | 87.8 | N/A | 5.4 |
| | 2 Weeks | 5 ± 3° C. | 12.2 | 87.8 | N/A | 5.3 |
| | | 25 ± 2° C./60 ± 5% RH | 13.8 | 86.2 | N/A | 5.4 |
| | | 40 ± 2° C./75 ± 5% RH | 22.3 | 77.7 | N/A | 5.4 |
| | 1 Month | 5 ± 3° C. | 12.1 | 87.9 | N/A | 5.5 |
| | | 25 ± 2° C./60 ± 5% RH | 15.3 | 84.7 | N/A | 5.5 |
| | | 40 ± 2° C./75 ± 5% RH | 33.1 | 66.9 | N/A | 5.5 |
| | 2 Month | 5 ± 3° C. | 13.7 | 86.3 | N/A | 5.4 |
| | | 25 ± 2° C./60 ± 5% RH | 23.9 | 76.1 | N/A | 5.4 |
| | | 40 ± 2° C./75 ± 5% RH | 56.2 | 38.2 | 5.7 | 5.5 |
| | 3 Month | 5 ± 3° C. | 12.8 | 87.2 | N/A | 5.4 |
| | | 25 ± 2° C./60 ± 5% RH | 26.9 | 73.1 | N/A | 5.4 |
| | 6 Month | 5 ± 3° C. | 14.7 | 85.3 | N/A | 5.4 |
| | | 25 ± 2° C./60 ± 5% RH | 43.9 | 56.1 | N/A | 5.4 |
| | 9 Month | 5 ± 3° C. | 13.9 | 86.1 | N/A | 5.4 |
| | 12 Month | 5 ± 3° C. | 17.3 | 82.7 | N/A | 5.4 |

TABLE 10

RP-HPLC Results- 12 M stability

| Formulation Code | Time Point | Condition | % Pegylated Area | % non-Pegylated Area |
|---|---|---|---|---|
| 1 | Initial | N/A | 100.0 | N/A |
| | 2 Weeks | 5 ± 3° C. | 100.0 | N/A |
| | | 25 ± 2° C./60 ± 5% RH | 100.0 | N/A |
| | | 40 ± 2° C./75 ± 5% RH | 96.4 | 1.3 |
| | 1 Month | 5 ± 3° C. | 99.6 | 0.4 |
| | | 25 ± 2° C./60 ± 5% RH | 99.2 | 0.4 |
| | | 40 ± 2° C./75 ± 5% RH | 92.5 | 2.3 |
| | 2 Month | 5 ± 3° C. | 99.5 | 0.1 |
| | | 25 ± 2° C./60 ± 5% RH | 97.6 | 0.9 |
| | | 40 ± 2° C./75 ± 5% RH | 84.6 | 4.6 |
| | 3 Month | 5 ± 3° C. | 98.9 | N/A |
| | | 25 ± 2° C./60 ± 5% RH | 95.1 | N/A |
| | 6 Month | 5 ± 3° C. | 99.3 | 0.4 |
| | | 25 ± 2° C./60 ± 5% RH | 92.0 | 2.3 |
| | 9 Month | 5 ± 3° C. | 95.5 | 0.5 |
| | 12 Month | 5 ± 3° C. | 98.3 | 0.52 |
| 2 | Initial | N/A | 100.0 | N/A |
| | 2 Weeks | 5 ± 3° C. | 100.0 | N/A |
| | | 25 ± 2° C./60 ± 5% RH | 100.0 | N/A |
| | | 40 ± 2° C./75 ± 5% RH | 98.5 | 0.8 |
| | 1 Month | 5 ± 3° C. | 100.0 | N/A |
| | | 25 ± 2° C./60 ± 5% RH | 99.3 | 0.3 |
| | | 40 ± 2° C./75 ± 5% RH | 96.5 | 1.6 |
| | 2 Month | 5 ± 3° C. | 99.2 | 0.2 |
| | | 25 ± 2° C./60 ± 5% RH | 97.5 | 0.6 |
| | | 40 ± 2° C./75 ± 5% RH | 89.3 | 3.6 |
| | 3 Month | 5 ± 3° C. | 99.0 | N/A |
| | | 25 ± 2° C./60 ± 5% RH | 96.9 | N/A |
| | 6 Month | 5 ± 3° C. | 97.8 | 0.5 |
| | | 25 ± 2° C./60 ± 5% RH | 92.8 | 1.6 |
| | 9 Month | 5 ± 3° C. | 95.3 | 0.3 |
| | 12 Month | 5 ± 3° C. | 99.1 | 0.4 |
| 3 | Initial | N/A | 100.0 | N/A |
| | 2 Weeks | 5 ± 3° C. | 100.0 | N/A |
| | | 25 ± 2° C./60 ± 5% RH | 100.0 | N/A |
| | | 40 ± 2° C./75 ± 5% RH | 97.9 | 0.8 |
| | 1 Month | 5 ± 3° C. | 100.0 | N/A |
| | | 25 ± 2° C./60 ± 5% RH | 99.8 | 0.2 |
| | | 40 ± 2° C./75 ± 5% RH | 97.2 | 1.4 |
| | 2 Month | 5 ± 3° C. | 99.5 | 0.1 |
| | | 25 ± 2° C./60 ± 5% RH | 98.7 | 0.5 |
| | | 40 ± 2° C./75 ± 5% RH | 88.8 | 3.2 |
| | 3 Month | 5 ± 3° C. | 99.0 | N/A |
| | | 25 ± 2° C./60 ± 5% RH | 94.3 | N/A |
| | 6 Month | 5 ± 3° C. | 99.3 | 0.4 |
| | | 25 ± 2° C./60 ± 5% RH | 92.8 | 1.7 |
| | 9 Month | 5 ± 3° C. | 96.3 | 0.4 |
| | 12 Month | 5 ± 3° C. | 98.90 | 0.5 |

TABLE 11

MFI Results - 12M stability

| Formulation | Time Point | Condition | Counts/mL ≥2 μm | ≥5 μm | ≥10 | ≥25 | Non-circ. frac. ≥5 μm |
|---|---|---|---|---|---|---|---|
| 1 | Initial | N/A | 1317 | 120 | 23 | 4 | 0.43 |
|   | 2 Week | 5 ± 3° C. | 2340 | 285 | 44 | 13 | 0.34 |
|   |   | 25 ± 2° C./60 ± 5% | 1588 | 138 | 4 | 4 | 0.31 |
|   |   | 40 ± 2° C./75 ± 5% | 2006 | 189 | 8 | 2 | 0.21 |
|   | 1 Month | 5 ± 3° C. | | | Not available | | |
|   |   | 25 ± 2° C./60 ± 5% | | | | | |
|   |   | 40 ± 2° C./75 ± 5% | | | | | |
|   | 2 Month | 5 ± 3° C. | 921 | 52 | 0 | 0 | 0.25 |
|   |   | 25 ± 2° C./60 ± 5% | 2450 | 182 | 6 | 2 | 0.40 |
|   |   | 40 ± 2° C./75 ± 5% | 2269 | 159 | 2 | 2 | 0.33 |
|   | 3 Month | 5 ± 3° C. | 2500 | 225 | 8 | 0 | 0.23 |
|   |   | 25 ± 2° C./60 ± 5% | 3090 | 414 | 36 | 0 | 0.26 |
|   | 6 Month | 5 ± 3° C. | | | Not available | | |
|   |   | 25 ± 2° C./60 ± 5% | 1919 | 88 | 13 | 8 | 0.65 |
|   | 9-Month | 5 ± 3° C. | 2210 | 237 | 31 | 2 | 0.52 |
|   | 12-Month | 5 ± 3° C. | 1112 | 71 | 10 | 0 | 0.46 |
| 2 | Initial | N/A | 1397 | 174 | 40 | 4 | 0.49 |
|   | 2 Week | 5 ± 3° C. | 1586 | 138 | 6 | 4 | 0.18 |
|   |   | 25 ± 2° C./60 ± 5% | 2375 | 268 | 34 | 2 | 0.34 |
|   |   | 40 ± 2° C./75 ± 5% | 2224 | 195 | 11 | 2 | 0.25 |
|   | 1 Month | 5 ± 3° C. | | | Not available | | |
|   |   | 25 ± 2° C./60 ± 5% | | | | | |
|   |   | 40 ± 2° C./75 ± 5% | | | | | |
|   | 2 Month | 5 ± 3° C. | 667 | 11 | 4 | 2 | 0.36 |
|   |   | 25 ± 2° C./60 ± 5% | 2247 | 166 | 0 | 0 | 0.27 |
|   |   | 40 ± 2° C./75 ± 5% | 2660 | 210 | 19 | 4 | 0.30 |
|   | 3 Month | 5 ± 3° C. | 2047 | 174 | 4 | 0 | 0.15 |
|   |   | 25 ± 2° C./60 ± 5% | 2109 | 214 | 4 | 2 | 0.21 |
|   | 6 Month | 5 ± 3° C. | 1278 | 32 | 4 | 0 | 0.34 |
|   |   | 25 ± 2° C./60 ± 5% | 1203 | 31 | 2 | 2 | 0.35 |
|   | 9-Month | 5 ± 3° C. | 1693 | 101 | 8 | 0 | 0.40 |
|   | 12-Month | 5 ± 3° C. | 766 | 34 | 0 | 0 | 0.44 |
| 3 | Initial | N/A | 570 | 61 | 11 | 2 | 0.25 |
|   | 2 Week | 5 ± 3° C. | 1503 | 117 | 13 | 4 | 0.20 |
|   |   | 25 ± 2° C./60 ± 5% | 1346 | 140 | 2 | 0 | 0.30 |
|   |   | 40 ± 2° C./75 ± 5% | 1137 | 63 | 4 | 0 | 0.30 |
|   | 1 Month | 5 ± 3° C. | | | Not available | | |
|   |   | 25 ± 2° C./60 ± 5% | | | | | |
|   |   | 40 ± 2° C./75 ± 5% | | | | | |
|   | 2 Month | 5 ± 3° C. | 1148 | 90 | 4 | 2 | 0.22 |
|   |   | 25 ± 2° C./60 ± 5% | 785 | 27 | 6 | 4 | 0.70 |
|   |   | 40 ± 2° C./75 ± 5% | 4351 | 1016 | 265 | 10 | 0.93 |
|   | 3 Month | 5 ± 3° C. | 2370 | 210 | 11 | 2 | 0.17 |
|   |   | 25 ± 2° C./60 ± 5% | 2513 | 227 | 29 | 0 | 0.16 |
|   | 6 Month | 5 ± 3° C. | | | Not available | | |
|   |   | 25 ± 2° C./60 ± 5% | 3008 | 139 | 0 | 0 | 0.48 |
|   | 9-Month | 5 ± 3° C. | 924 | 65 | 0 | 0 | 0.41 |
|   | 12-Month | 5 ± 3° C. | 798 | 40 | 2 | 2 | 0.57 |

Stability data for formulation 2 is presented in Tables 12 and 13.

TABLE 12

Long-Term Stability Data for Liquid formulation at 5 ± 3° C.

| Test | Acceptance Criteria | Time (Months) 0 | 0.5 | 1 | 2 | 3 | 6 | 9 | 12 |
|---|---|---|---|---|---|---|---|---|---|
| Appearance | Colorless, clear liquid. Free of visible particulates | Colorless, clear liquid. Free of visible particulates | Colorless, clear liquid. Free of visible particulates | Colorless, clear liquid. Free of visible particulates | Colorless, clear liquid. Free of visible particulates | Colorless, clear liquid. Free of visible particulates | Colorless, clear liquid. Free of visible particulates | Colorless, clear liquid. Free of visible particulates | Colorless, clear liquid. Free of visible particulates |

TABLE 12-continued

Long-Term Stability Data for Liquid formulation at 5 ± 3° C.

| Test | Acceptance Criteria | Time (Months) | | | | | | | |
|---|---|---|---|---|---|---|---|---|---|
| | | 0 | 0.5 | 1 | 2 | 3 | 6 | 9 | 12 |
| pH | 7.5 ± 0.3 | 7.4 | 7.3 | 7.4 | 7.3 | 7.4 | 7.4 | 7.4 | 7.3 |
| Osmolality | 250-380 mOsmol/kg | 302 | NT | NT | NT | NT | NT | NT | NT |
| Protein Concentration (UV280) SoloVPE | 20.0 ± 3.0 mg/mL | 19.2 | 19.2 | 19.3 | 19.2 | 19.2 | 19.2 | 19.3 | 19.4 |
| RP-HPLC (purity) | Report result (%) | 100.0 | 100.0 | 100.0 | 99.2 | 99.0 | 97.8 | 95.3 | 99.1 |
| SE-HPLC % Monomer | ≥70.0% | 85.7 | 83.4 | 80.0 | 78.4 | 78.2 | 76.3 | 78.1 | 78.4 |
| % Dimer | ≤25.0% | 14.0 | 16.3 | 19.4 | 21.0 | 21.3 | 22.7 | 21.1 | 20.6 |
| % HOA | ≤5.0% | 0.3 | 0.3 | 0.7 | 0.5 | 0.3 | 0.8 | 0.4 | 0.5 |
| SDS-PAGE: Non-Reduced | Comparable to reference standard | Conforms | Conforms | Conforms | Conforms | Conforms | Conforms | Conforms | Conforms |
| SDS-PAGE: Reduced | Comparable to reference standard | Conforms | Conforms | Conforms | Conforms | Conforms | Conforms | Conforms | Conforms |
| icIEF % Main Peak | ≥70.0% | 87.9 | 87.8 | 86.7 | 87.2 | 87.2 | 86.5 | 85.4 | 84.1 |
| % Acidic Peak | ≤30.0% | 12.1 | 12.2 | 13.3 | 12.8 | 12.8 | 13.5 | 14.6 | 15.9 |
| % Basic Peak | ≤10.0% | ND | ND | ND | ND | ND | ND | ND | ND |
| Cell Based Potency | 60-140% relative to reference standard | NT | NT | NT | NT | NT | NT | NT | 111[a] |

NT = Not tested or not planned to be tested;
ND = Not Detected.
HOA = Higher Order Aggregates.
[a] = Testing added.

TABLE 13

Accelerated Stability Data for Liquid Formulation at 25 ± 2° C.

| Test | Acceptance Criteria | Time (Months) | | | | | |
|---|---|---|---|---|---|---|---|
| | | 0 | 0.5 | 1 | 2 | 3 | 6 |
| Appearance | Colorless, clear liquid. Free of visible particulates | Colorless, clear liquid. Free of visible particulates | Colorless, clear liquid. Free of visible particulates | Colorless, clear liquid. Free of visible particulates | Colorless, clear liquid. Free of visible particulates | Colorless, clear liquid. Free of visible particulates | Colorless, clear liquid. Free of visible particulates |
| pH | 7.5 ± 0.3 | 7.4 | 7.4 | 7.4 | 7.4 | 7.4 | 7.5 |
| Osmolality | 250-380 mOsmol/kg | 302 | NT | NT | NT | NT | NT |
| Protein Concentration (UV280) SoloVPE | 20.0 ± 3.0 mg/mL | 19.2 | 19.3 | 19.2 | 19.1 | 19.1 | 19.2 |
| RP-HPLC (purity) | Report result (%) | 100.0 | 100.0 | 99.3 | 97.5 | 96.9 | 92.8 |
| SE-HPLC % Monomer | ≥70.0% | 85.7 | 76.5 | 76.4 | 76.8 | 76.9 | 72.8 |
| % Dimer | ≤25.0% | 14.0 | 22.9 | 22.5 | 21.7 | 21.4 | 23.9 |
| % HOA | ≤5.0% | 0.3 | 0.5 | 0.8 | 0.6 | 0.4 | 0.6 |
| SDS-PAGE: Non-Reduced | Comparable to reference standard | Conforms | Conforms | Conforms | Conforms | Conforms | Conforms |
| SDS-PAGE: Reduced | Comparable to reference standard | Conforms | Conforms | Conforms | Conforms | Conforms | Conforms |
| icIEF % Main Peak | ≥70.0% | 87.9 | 86.4 | 84.2 | 76.6 | 70.8 | 56.1 |
| % Acidic Peak | ≤30.0% | 12.1 | 13.6 | 15.8 | 23.4 | 29.2 | 43.9 |
| % Basic Peak | ≤10.0% | ND | ND | ND | ND | ND | ND |
| Cell Based Potency | 60-140% relative to reference standard | NT | NT | NT | NT | NT | NT |

NT = Not tested or not planned to be tested;
ND = Not Detected.
HOA = Higher Order Aggregates.

Table 14 shows the accelerated profile of formulation comprising comprises 28 mg/mL mutant FGF21 peptide conjugate, 260 mM Arginine HCl, 20 mM Tris, 0.2 mg/ml PS80, pH 7.1

TABLE 14

| Attributes | N/A T0 | 25° C. T2 W | 25° C. T1 M | 40° C. T1 M |
|---|---|---|---|---|
| SEC-HPLC % Monomer | 88.2% | 86.1% | 84.3% | 66.6% |
| SEC-HPLC % Dimer | 11.3% | 12.8% | 14.2% | 28.2% |
| Higher Order Aggregate | 0.5% | 0.8% | 0.7% | 1.4% |
| Low molecular weight | Not Detected | 0.4% | 0.8% | 3.9% |
| iCIEF main peak | 89.94% | 88.3% | 85.2% | 65% |
| iCIEF acid peak | 10.1% | 11.7% | 13.4% | 33% |
| Basic Variants | ND | ND | <LOD | <LOD |
| Potency | 116% | 104% | 98% | N/A |

Table 15 below provides a ranking of based on additional excipient screening for further optimization.

TABLE 15

| Formulation # | Base Formulation, 20 mg/mL unless otherwise noted | Excipient | Surfactant | % Total Aggregates |
|---|---|---|---|---|
| 9 | 20 mM Tris, pH 7.5 | 500 mM Arg•HCl | N/A | 4.9 |
| 8 | 20 mM Tris, pH 7.5 | 400 mM Arg•HCl | N/A | 5.5 |
| 7 | 20 mM Tris, pH 7.5 | 300 mM Arg•HCl | N/A | 8.9 |
| 3 | 10 mg/mL, 20 mM Tris, pH 7.5 | 150 mM Arg•HCl | N/A | 15.0 |
| 6 | 20 mM Tris, pH 7.5 | 200 mM Arg•HCl | N/A | 17.9 |
| 5 | 20 mM Tris, pH 8.0 | 150 mM Arg•HCl | N/A | 18.9 |
| 30 | 20 mM Tris, pH 7.5 | 150 mM Arg•HCl | 0.1% (w/v) Cetrimonium Bromide | 19.8 |
| 4 | 20 mM Tris, pH 7.0 | 150 mM Arg•HCl | N/A | 19.9 |
| 27 | 20 mM Tris, pH 7.5 | 150 mM Arg•HCl | 0.05% (w/v) Sodium Gluconate | 21.1 |
| 28 | 20 mM Tris, pH 7.5 | 150 mM Arg•HCl | 0.1% (w/v) Sodium Gluconate | 21.1 |
| 29 | 20 mM Tris, pH 7.5 | 150 mM Arg•HCl | 0.05% (w/v) Cetrimonium Bromide | 21.3 |
| 22 | 20 mM Tris, pH 7.5 | 250 mM Alanine | N/A | 31.7 |
| 26 | 20 mM Tris, pH 7.5 | 5% (v/v) PEG 400 | N/A | 32.2 |
| 24 | 20 mM Tris, pH 7.5 | 5% (v/v) Glycerol | N/A | 33.1 |
| 19 | 20 mM Tris, pH 7.5 | 250 mM Glycine | N/A | 35.4 |
| 12 | 20 mM Tris, pH 7.5 | 50 mM MgCl2 | N/A | 37.8 |
| 13 | 20 mM Tris, pH 7.5 | 100 mM MgCl2 | N/A | 37.8 |
| 10 | 20 mM Tris, pH 7.5 | 50 mM Arg•Sulfate | N/A | 37.8 |
| 17 | 20 mM Tris, pH 7.5 | 50 mM Glycine | N/A | 38.6 |
| 18 | 20 mM Tris, pH 7.5 | 100 mM Glycine | N/A | 39.2 |
| 21 | 20 mM Tris, pH 7.5 | 100 mM Alanine | N/A | 39.4 |
| 15 | 20 mM Tris, pH 7.5 | 100 mM Proline | N/A | 39.4 |
| 25 | 20 mM Tris, pH 7.5 | 1% (v/v) PEG 400 | N/A | 40.1 |
| 14 | 20 mM Tris, pH 7.5 | 50 mM Proline | N/A | 40.6 |
| 20 | 20 mM Tris, pH 7.5 | 50 mM Alanine | N/A | 41.4 |
| 11 | 20 mM Tris, pH 7.5 | 100 mM Arg•Sulfate | N/A | 42.9 |
| 23 | 20 mM Tris, pH 7.5 | 1% (v/v) Glycerol | N/A | 43.9 |
| 16 | 20 mM Tris, pH 7.5 | 250 mM Proline | N/A | 44.5 |

All publications mentioned herein are hereby incorporated by reference in their entireties. While the foregoing invention has been described in some detail for purposes of clarity and understanding, it will be appreciated by one skilled in the art from a reading of the disclosure that various changes in form and detail can be made without departing from the true scope of the invention in the appended claims.

Specific examples of methods and kits have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, ele ments and/or acts from different embodiments; combining features, elements and/or acts from embodiments as described herein with features, elements and/or acts of other technology; and/or omitting combining features, elements and/or acts from described embodiments.

The embodiments of the invention described above are intended to be exemplary only. Those skilled in this art will understand that various modifications of detail may be made to these embodiments, all of which come within the scope of the invention.

```
                         SEQUENCE LISTING

Sequence total quantity: 28
SEQ ID NO: 1            moltype = AA   length = 182
FEATURE                 Location/Qualifiers
source                  1..182
                        mol_type = protein
                        organism = Homo sapiens
SEQUENCE: 1
MHPIPDSSPL LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPLHLP   120
GNKSPHRDPA PRGPARFLPL PGLPPALPEP PGILAPQPPD VGSSDPLSMV GPSQGRSPSY   180
AS                                                                 182

SEQ ID NO: 2            moltype = AA   length = 182
FEATURE                 Location/Qualifiers
REGION                  1..182
                        note = mutant
source                  1..182
                        mol_type = protein
                        organism = synthetic construct
SEQUENCE: 2
MHPIPDSSPL LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPLHLP   120
GNKSPHRDPA PRGPARFLPL PGLPPALPEP PGILAPQPPD VGSSDPLSMV GPTQGASPSY   180
AS                                                                 182

SEQ ID NO: 3            moltype = AA   length = 182
FEATURE                 Location/Qualifiers
REGION                  1..182
                        note = mutant
source                  1..182
                        mol_type = protein
                        organism = synthetic construct
SEQUENCE: 3
MHPIPDSSPL LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPLHLP   120
GNKSPHRDPA PRGPARFLPL PGLPPALPEP PGILAPQPPD VGSSDPLSMV GPTQGAMPSY   180
AS                                                                 182

SEQ ID NO: 4            moltype = AA   length = 182
FEATURE                 Location/Qualifiers
REGION                  1..182
                        note = mutant
source                  1..182
                        mol_type = protein
                        organism = synthetic construct
SEQUENCE: 4
MHPIPDSSPL LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPLHLP   120
GNKSPHRDPA PRGPARFLPL PGLPPALPEP PGILAPTPPD VGSSDPLSMV GPSQGRSPSY   180
AS                                                                 182

SEQ ID NO: 5            moltype = AA   length = 182
FEATURE                 Location/Qualifiers
REGION                  1..182
                        note = mutant
source                  1..182
                        mol_type = protein
                        organism = synthetic construct
SEQUENCE: 5
MHPIPTSSPL LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPLHLP   120
GNKSPHRDPA PRGPARFLPL PGLPPALPEP PGILAPQPPD VGSSDPLSMV GPSQGRSPSY   180
AS                                                                 182

SEQ ID NO: 6            moltype = AA   length = 182
FEATURE                 Location/Qualifiers
REGION                  1..182
                        note = mutant
source                  1..182
                        mol_type = protein
                        organism = synthetic construct
```

```
SEQUENCE: 6
MHPTPDSSPL LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPLHLP   120
GNKSPHRDPA PRGPARFLPL PGLPPALPEP PGILAPQPPD VGSSDPLSMV GPSQGRSPSY   180
AS                                                                 182

SEQ ID NO: 7              moltype = AA  length = 182
FEATURE                   Location/Qualifiers
REGION                    1..182
                          note = mutant
source                    1..182
                          mol_type = protein
                          organism = synthetic construct
SEQUENCE: 7
MHPIPDSSPT LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPLHLP   120
GNKSPHRDPA PRGPARFLPL PGLPPALPEP PGILAPQPPD VGSSDPLSMV GPSQGRSPSY   180
AS                                                                 182

SEQ ID NO: 8              moltype = AA  length = 182
FEATURE                   Location/Qualifiers
REGION                    1..182
                          note = mutant
source                    1..182
                          mol_type = protein
                          organism = synthetic construct
SEQUENCE: 8
MHPIPDSSPL LQFGGQVRQR YLYTDDAQQT EAHLEIREDG TVGGAADQSP TSLLQLKALK    60
PGVIQILGVK TSRFLCQRPD GALYGSLHFD PEACSFRELL LEDGYNVYQS EAHGLPLHLP   120
GNKSPHRDPA PRGPARFLPL PGLPPALPEP PGILAPQPPD VGSSDPLSMV GPSQGRSPSY   180
AS                                                                 182

SEQ ID NO: 9              moltype = AA  length = 182
FEATURE                   Location/Qualifiers
REGION                    1..182
                          note = mutant
source                    1..182
                          mol_type = protein
                          organism = synthetic construct
SEQUENCE: 9
MHPIPDSSPL LQFGGQVRQR YLYTDDAQQT EAHLEIREDG TVGGAADQSP ESLLQLKALK    60
PTVIQILGVK TSRFLCQRPD GALYGSLHFD PEACSFRELL LEDGYNVYQS EAHGLPLHLP   120
GNKSPHRDPA PRGPARFLPL PGLPPALPEP PGILAPQPPD VGSSDPLSMV GPSQGRSPSY   180
AS                                                                 182

SEQ ID NO: 10             moltype = AA  length = 182
FEATURE                   Location/Qualifiers
REGION                    1..182
                          note = mutant
source                    1..182
                          mol_type = protein
                          organism = synthetic construct
SEQUENCE: 10
MHPIPDSSPL LQFGGQVRQR YLYTDDAQQT EAHLEIREDG TVGGAADQSP ESLLQLKALK    60
PGVIQILGVK TSRFLCQRPT GALYGSLHFD PEACSFRELL LEDGYNVYQS EAHGLPLHLP   120
GNKSPHRDPA PRGPARFLPL PGLPPALPEP PGILAPQPPD VGSSDPLSMV GPSQGRSPSY   180
AS                                                                 182

SEQ ID NO: 11             moltype = AA  length = 182
FEATURE                   Location/Qualifiers
REGION                    1..182
                          note = mutant
source                    1..182
                          mol_type = protein
                          organism = synthetic construct
SEQUENCE: 11
MHPIPDSSPL LQFGGQVRQR YLYTDDAQQT EAHLEIREDG TVGGAADQSP ESLLQLKALK    60
PGVIQILGVK TSRFLCQRPD GALYGSLHFD PTACSFRELL LEDGYNVYQS EAHGLPLHLP   120
GNKSPHRDPA PRGPARFLPL PGLPPALPEP PGILAPQPPD VGSSDPLSMV GPSQGRSPSY   180
AS                                                                 182

SEQ ID NO: 12             moltype = AA  length = 182
FEATURE                   Location/Qualifiers
REGION                    1..182
                          note = mutant
source                    1..182
                          mol_type = protein
                          organism = synthetic construct
SEQUENCE: 12
```

```
MHPIPDSSPL LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPTHLP   120
GNKSPHRDPA PRGPARFLPL PGLPPALPEP PGILAPQPPD VGSSDPLSMV GPSQGRSPSY   180
AS                                                                 182

SEQ ID NO: 13             moltype = AA   length = 182
FEATURE                   Location/Qualifiers
REGION                    1..182
                          note = mutant
source                    1..182
                          mol_type = protein
                          organism = synthetic construct
SEQUENCE: 13
MHPIPDSSPL LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPHLP   120
TNKSPHRDPA PRGPARFLPL PGLPPALPEP PGILAPQPPD VGSSDPLSMV GPSQGRSPSY   180
AS                                                                 182

SEQ ID NO: 14             moltype = AA   length = 182
FEATURE                   Location/Qualifiers
REGION                    1..182
                          note = mutant
source                    1..182
                          mol_type = protein
                          organism = synthetic construct
SEQUENCE: 14
MHPIPDSSPL LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPHLP   120
GNKSPTRDPA PRGPARFLPL PGLPPALPEP PGILAPQPPD VGSSDPLSMV GPSQGRSPSY   180
AS                                                                 182

SEQ ID NO: 15             moltype = AA   length = 182
FEATURE                   Location/Qualifiers
REGION                    1..182
                          note = mutant
source                    1..182
                          mol_type = protein
                          organism = synthetic construct
SEQUENCE: 15
MHPIPDSSPL LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPHLP   120
GNKSPHRDPT PRGPARFLPL PGLPPALPEP PGILAPQPPD VGSSDPLSMV GPSQGRSPSY   180
AS                                                                 182

SEQ ID NO: 16             moltype = AA   length = 182
FEATURE                   Location/Qualifiers
REGION                    1..182
                          note = mutant
source                    1..182
                          mol_type = protein
                          organism = synthetic construct
SEQUENCE: 16
MHPIPDSSPL LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPHLP   120
GNKSPHRDPA PTGPARFLPL PGLPPALPEP PGILAPQPPD VGSSDPLSMV GPSQGRSPSY   180
AS                                                                 182

SEQ ID NO: 17             moltype = AA   length = 182
FEATURE                   Location/Qualifiers
REGION                    1..182
                          note = mutant
source                    1..182
                          mol_type = protein
                          organism = synthetic construct
SEQUENCE: 17
MHPIPDSSPL LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPHLP   120
GNKSPHRDPA PRGPTRFLPL PGLPPALPEP PGILAPQPPD VGSSDPLSMV GPSQGRSPSY   180
AS                                                                 182

SEQ ID NO: 18             moltype = AA   length = 182
FEATURE                   Location/Qualifiers
REGION                    1..182
                          note = mutant
source                    1..182
                          mol_type = protein
                          organism = synthetic construct
SEQUENCE: 18
MHPIPDSSPL LQFGGQVRQR YLYTDDAQQT EAHLEIREDG TVGGAADQSP ESLLQLKALK    60
```

```
PGVIQILGVK  TSRFLCQRPD  GALYGSLHFD  PEACSFRELL  LEDGYNVYQS  EAHGLPLHLP     120
GNKSPHRDPA  PRGPARFLPT  PGLPPALPEP  PGILAPQPPD  VGSSDPLSMV  GPSQGRSPSY     180
AS                                                                          182

SEQ ID NO: 19            moltype = AA  length = 182
FEATURE                  Location/Qualifiers
REGION                   1..182
                         note = mutant
source                   1..182
                         mol_type = protein
                         organism = synthetic construct
SEQUENCE: 19
MHPIPDSSPL  LQFGGQVRQR  YLYTDDAQQT  EAHLEIREDG  TVGGAADQSP  ESLLQLKALK      60
PGVIQILGVK  TSRFLCQRPD  GALYGSLHFD  PEACSFRELL  LEDGYNVYQS  EAHGLPLHLP     120
GNKSPHRDPA  PRGPARFLPL  PTLPPALPEP  PGILAPQPPD  VGSSDPLSMV  GPSQGRSPSY     180
AS                                                                          182

SEQ ID NO: 20            moltype = AA  length = 183
FEATURE                  Location/Qualifiers
REGION                   1..183
                         note = mutant
source                   1..183
                         mol_type = protein
                         organism = synthetic construct
SEQUENCE: 20
MHPIPDSSPL  LQFGGQVRQR  YLYTDDAQQT  EAHLEIREDG  TVGGAADQSP  ESLLQLKALK      60
PGVIQILGVK  TSRFLCQRPD  GALYGSLHFD  PEACSFRELL  LEDGYNVYQS  EAHGLPLHLP     120
GNKSPHRDPA  PRGPARFLPL  PGLPTPALPE  PPGILAPQPP  DVGSSDPLSM  VGPSQGRSPS     180
YAS                                                                         183

SEQ ID NO: 21            moltype = AA  length = 182
FEATURE                  Location/Qualifiers
REGION                   1..182
                         note = mutant
source                   1..182
                         mol_type = protein
                         organism = synthetic construct
SEQUENCE: 21
MHPIPDSSPL  LQFGGQVRQR  YLYTDDAQQT  EAHLEIREDG  TVGGAADQSP  ESLLQLKALK      60
PGVIQILGVK  TSRFLCQRPD  GALYGSLHFD  PEACSFRELL  LEDGYNVYQS  EAHGLPLHLP     120
GNKSPHRDPA  PRGPARFLPL  PGLPPTLPEP  PGILAPQPPD  VGSSDPLSMV  GPSQGRSPSY     180
AS                                                                          182

SEQ ID NO: 22            moltype = AA  length = 182
FEATURE                  Location/Qualifiers
REGION                   1..182
                         note = mutant
source                   1..182
                         mol_type = protein
                         organism = synthetic construct
SEQUENCE: 22
MHPIPDSSPL  LQFGGQVRQR  YLYTDDAQQT  EAHLEIREDG  TVGGAADQSP  ESLLQLKALK      60
PGVIQILGVK  TSRFLCQRPD  GALYGSLHFD  PEACSFRELL  LEDGYNVYQS  EAHGLPLHLP     120
GNKSPHRDPA  PRGPARFLPL  PGLPPALPTP  PGILAPQPPD  VGSSDPLSMV  GPSQGRSPSY     180
AS                                                                          182

SEQ ID NO: 23            moltype = AA  length = 183
FEATURE                  Location/Qualifiers
REGION                   1..183
                         note = mutant
source                   1..183
                         mol_type = protein
                         organism = synthetic construct
SEQUENCE: 23
MHPIPDSSPL  LQFGGQVRQR  YLYTDDAQQT  EAHLEIREDG  TVGGAADQSP  ESLLQLKALK      60
PGVIQILGVK  TSRFLCQRPD  GALYGSLHFD  PEACSFRELL  LEDGYNVYQS  EAHGLPLHLP     120
GNKSPHRDPA  PRGPARFLPL  PGLPPALPEP  TPGILAPQPP  DVGSSDPLSM  VGPSQGRSPS     180
YAS                                                                         183

SEQ ID NO: 24            moltype = AA  length = 182
FEATURE                  Location/Qualifiers
REGION                   1..182
                         note = mutant
source                   1..182
                         mol_type = protein
                         organism = synthetic construct
SEQUENCE: 24
MHPIPDSSPL  LQFGGQVRQR  YLYTDDAQQT  EAHLEIREDG  TVGGAADQSP  ESLLQLKALK      60
PGVIQILGVK  TSRFLCQRPD  GALYGSLHFD  PEACSFRELL  LEDGYNVYQS  EAHGLPLHLP     120
```

```
GNKSPHRDPA PRGPARFLPL PGLPPALPEP PTILAPQPPD VGSSDPLSMV GPSQGRSPSY    180
AS                                                                  182

SEQ ID NO: 25           moltype = AA  length = 183
FEATURE                 Location/Qualifiers
REGION                  1..183
                        note = mutant
source                  1..183
                        mol_type = protein
                        organism = synthetic construct
SEQUENCE: 25
MHPIPDSSPL LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPLHLP    120
GNKSPHRDPA PRGPARFLPL PGLPPALPEP PGILAPQPTP DVGSSDPLSM VGPSQGRSPS    180
YAS                                                                 183

SEQ ID NO: 26           moltype = AA  length = 182
FEATURE                 Location/Qualifiers
REGION                  1..182
                        note = mutant
source                  1..182
                        mol_type = protein
                        organism = synthetic construct
SEQUENCE: 26
MHPIPDSSPL LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPLHLP    120
GNKSPHRDPA PRGPARFLPL PGLPPALPEP PGILAPQPPT VGSSDPLSMV GPSQGRSPSY    180
AS                                                                  182

SEQ ID NO: 27           moltype = AA  length = 182
FEATURE                 Location/Qualifiers
REGION                  1..182
                        note = mutant
source                  1..182
                        mol_type = protein
                        organism = synthetic construct
SEQUENCE: 27
MHPIPDSSPL LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPLHLP    120
GNKSPHRDPA PRGPARFLPL PGLPPALPEP PGILAPQPPD VGSSDPTSMV GPSQGRSPSY    180
AS                                                                  182

SEQ ID NO: 28           moltype = AA  length = 182
FEATURE                 Location/Qualifiers
REGION                  1..182
                        note = mutant
source                  1..182
                        mol_type = protein
                        organism = synthetic construct
SEQUENCE: 28
MHPIPDSSPL LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPLHLP    120
GNKSPHRDPA PRGPARFLPL PGLPPALPEP PGILAPQPPD VGSSDPLSMV GPSQGRSPTY    180
AS                                                                  182
```

The invention claimed is:

1. A prefilled syringe or autoinjector comprising a liquid pharmaceutical composition, the liquid pharmaceutical composition comprising:
   (a) 28 mg/ml of a mutant Fibroblast Growth Factor-21 (FGF-21) peptide conjugate comprising:
      i) a mutant FGF-21 peptide comprising the amino acid sequence of SEQ ID NO: 2,
      ii) a glycosyl moiety, and
      iii) a 20 kDa polyethylene glycol (PEG),
      wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG;
   (b) 260 mM arginine;
   (c) 0.02% Polysorbate 80 (PS-80);
   (d) 20 mM buffer, wherein pH is 7.1; and
   (e) a pharmaceutically acceptable carrier.

2. The prefilled syringe or autoinjector of claim 1, wherein the liquid pharmaceutical composition is stable at a temperature of 2° C. to 8° C. for 12 months or more.

3. The prefilled syringe or autoinjector of claim 1, wherein the arginine is arginine HCl or arginine sulfate.

4. A prefilled syringe or autoinjector comprising a liquid pharmaceutical composition, the liquid pharmaceutical composition comprising:
   (a) 36 mg/ml of a mutant Fibroblast Growth Factor-21 (FGF-21) peptide conjugate comprising:
      i) a mutant FGF-21 peptide comprising the amino acid sequence of SEQ ID NO: 2,
      ii) a glycosyl moiety, and
      iii) a 20 kDa polyethylene glycol (PEG),
      wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG;
- (b) 270 mM arginine;
- (c) 0.02% Polysorbate 80 (PS-80);
- (d) 20 mM buffer, wherein pH is 7.1; and
- (e) a pharmaceutically acceptable carrier.

5. The prefilled syringe or autoinjector of claim 4, wherein the liquid pharmaceutical composition is stable at a temperature of 2° C. to 8° C. for 12 months or more.

6. The prefilled syringe or autoinjector of claim 4, wherein the arginine is arginine HCl or arginine sulfate.

7. A prefilled syringe or autoinjector comprising a liquid pharmaceutical composition, the liquid pharmaceutical composition comprising:
- (a) 42 mg/ml of a mutant Fibroblast Growth Factor-21 (FGF-21) peptide conjugate comprising:
  - i) a mutant FGF-21 peptide comprising the amino acid sequence of SEQ ID NO: 2,
  - ii) a glycosyl moiety, and
  - iii) a 20 kDa polyethylene glycol (PEG),
  - wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG;
- (b) 270 mM arginine;
- (c) 0.02% Polysorbate 80 (PS-80);
- (d) 20 mM buffer, wherein pH is 7.1; and
- (e) a pharmaceutically acceptable carrier.

8. The prefilled syringe or autoinjector of claim 7, wherein the liquid pharmaceutical composition is stable at a temperature of 2° C. to 8° C. for 12 months or more.

9. The prefilled syringe or autoinjector of claim 7, wherein the arginine is arginine HCl or arginine sulfate.

* * * * *